US007001718B2

(12) United States Patent
Jacobs et al.

(10) Patent No.: US 7,001,718 B2
(45) Date of Patent: Feb. 21, 2006

(54) METHOD OF INHIBITING PATHOGENICITY OF INFECTIOUS AGENTS

(75) Inventors: Bertram L. Jacobs, Tempe, AZ (US); Alexander Rich, Cambridge, MA (US)

(73) Assignees: Massachusetts Institute of Technology, Cambridge, MA (US); Arizona Board of Regents, Tempe, AZ (US)

( * ) Notice: Subject to any disclaimer, the term of this patent is extended or adjusted under 35 U.S.C. 154(b) by 0 days.

(21) Appl. No.: 10/321,785

(22) Filed: Dec. 16, 2002

(65) Prior Publication Data

US 2003/0211964 A1   Nov. 13, 2003

Related U.S. Application Data

(60) Provisional application No. 60/343,028, filed on Dec. 20, 2001.

(51) Int. Cl.
*C12Q 1/70*   (2006.01)
*C12Q 1/18*   (2006.01)
*G01N 33/556*  (2006.01)
*G01N 33/53*   (2006.01)

(52) U.S. Cl. .............................. 435/5; 435/7.1; 435/32; 436/501

(58) Field of Classification Search .................... 435/5, 435/32, 7.1; 436/501
See application file for complete search history.

(56) References Cited

U.S. PATENT DOCUMENTS 5,726,050 A    3/1998   Rich et al.

FOREIGN PATENT DOCUMENTS

| WO | WO 97/00949 | 1/1997 |
| WO | WO 00/73487 A1 | 12/2000 |

OTHER PUBLICATIONS

Herbert et al (Genetica 106:37-47, 1999, abstract only cited).*
Inoue et al, BBRC 266:147-151, 1999.*
Blaho et al, Journal of Biological Chemistry 262:6062-6068, 1987.*
Kim, Y.G. et al., "A Role for Z-DNA Binding in Vaccinia Virus Pathogenesis," *Proc. Natl. Acad. Sci. USA*, 100(12): 6974-6979 (2003).
Rich, A. et al., "Z-DNA: The Long Road to Biological Function," *Nature Reviews*, 4(7):566-572 (2003).
Oh, D.-B., et al., "Z-DNA-Binding Proteins Can Act as Potent Effectors of Gene Expression *In Vivo,*" *Proceedings of the National Academy of Sciences U.S.A.*, 99(26):16666-16671 (2002).

Kim, Y.-G., et al., "A Role for Z-DNA Binding in Vaccinia Virus Pathogenesis," *Proceedings of the National Academy of Sciences U.S.A.*, 100(12):6974-6979 (2003).
Behe, M. and Felsenfeld, G., "Effects of Methylation on a Synthetic Polynucleotide: The B-Z Transition in Poly(dG-m$^5$dC) • Poly(dG-m$^5$dC)," *Proceedings of the National Academy of Sciences U.S.A.*, 78:1619-1623 (1981).
Berger, I., et al., "Spectroscopic Characterization of a DNA-Binding Domain, Zα, from the Editing Enzyme, dsRNA Adenosine Deaminase: Evidence for Left-Handed Z-DNA in the Zα-DNA Complex," *Biochemistry*, 37:13313-13321 (1998).
Bloom, D.C., et al., "Identification and Characterization of Two Nonessential Regions of the Rabbitpox Virus Genome Involved in Virulence," *Journal of Virology*, 65:1530-1542 (1991).
Brandt, T.A. and Jacobs, B.L., "Both Carboxy- and Amino-Terminal Domains of the Vaccinia Virus Interferon Resistance Gene, E3L, Are Required for Pathogenesis in a Mouse Model," *Journal of Virology*, 75:850-856 (2001).
Brigido, M.M. and Stollar, B.D., "Two Induced Anti-Z-DNA Monoclonal Antibodies Use VH Gene Segments Related to Those of Anti-DNA Autoantibodies," *The Journal of Immunology*, 146:2005-2009 (1991).
Brown, B.A., et al., "The Zα Domain of the Editing Enzyme dsRNA Adenosine Deaminase Binds Left-Handed Z-RNA as Well as Z-DNA," *Proceedings of the National Academy of Sciences U.S.A.*, 97:13532-13536 (2000).
Enserink, M. And Stone, R., "Dead Virus Walking," *Science*, 295:2001-2003 and 2005 (Mar., 2002).
Fu, Y., et al., "Cloning of DLM-1, A Novel Gene that is Up-Regulated in Activated Macrophages, Using RNA Differential Display," *Gene*, 240:157-163 (1999).
Herbert, A. and Rich, A., "The Biology of Left-Handed Z-DNA," *The Journal of Biological Chemistry*, 271:11595-11598 (1996).
Herbert, A.G. and Rich, A., "A Method to Identify and Characterize Z-DNA Binding Proteins Using a Linear Oligodeoxynucleotide," *Nucleic Acids Research*, 21:2669-2672 (1993).
Herbert, A., et al., "A Z-DNA Binding Domain Present in the Human Editing Enzyme, Double-Stranded RNA Adenosine Deaminase," *Proceedings of the National Academy of Sciences U.S.A.*, 94:8421-8426 (1997).
Herbert, A., et al., "The Zα Domain from Human ADAR1 Binds to the Z-DNA Conformer of Many Different Sequences," *Nucleic Acids Research*, 26:3486-3493 (1998).

(Continued)

*Primary Examiner*—Mary E. Mosher
(74) *Attorney, Agent, or Firm*—Hamilton, Brook, Smith & Reynolds, P.C.

(57)   ABSTRACT

The present invention relates to methods of detecting or identifying inhibitors of a Z-DNA binding ligand to Z-DNA, methods of inhibiting the pathogenicity of an infectious agent, antiviral therapies, and compounds that inhibit complex formation between a Z-DNA binding ligand and Z-DNA.

51 Claims, 20 Drawing Sheets

OTHER PUBLICATIONS

Jiang, H., et al., "Potassium Permanganate as an *In Situ* Probe for B-Z and Z-Z Junctions," *Nucleic Acids Research*, 19:6943-6948 (1991).

Kibler, K.V., et al., "Double-Stranded RNA Is a Trigger for Apoptosis in Vaccinia Virus-Infected Cells," *Journal of Virology*, 71:1992-2003 (1997).

Kim, J-M., et al., "Analysis of Left-Handed Z-DNA Formation in Short d(CG)$_n$ Sequences in *Escherichia coli* and *Halobacterium halobium* Plasmids," *The Journal of Biological Chemistry*, 271:9340-9346 (1996).

Kim, Y-G., et al., "Construction of a Z-DNA-Specific Restriction Endonuclease," *Proceedings of the National Academy of Sciences USA*, 94:12875-12879 (1997).

Kim, Y-G., et al., "The Interaction Between Z-DNA and the Zab Domain of Double-Stranded RNA Adenosine Deaminase Characterized Using Fusion Nucleases," *The Journal of Biological Chemistry*, 274:19081-19086 (1999).

Kim, Y-G., et al., "The Zab Domain of the Human RNA Editing Enzyme ADAR1 Recognizes Z-DNA When Surrounded by B-DNA," *The Journal of Biological Chemistry*, 275:26828-26833 (2000).

Liu, J., et al., "Identifying DNA-Binding Sites and Analyzing DNA-Binding Domains Using a Yeast Selection System," *Methods: A Companion to Methods in Enzymology*, 5:125-137 (1993).

Qu, X, et al., "Allosteric, Chiral-Selective Drug Binding to DNA," *Proceedings of the National Academy of Sciences U.S.A.*, 97:12032-12037 (Oct., 2000).

Rich, A., "A Therapy for Smallpox," *CRISP—Computer Retrieval of Informational on Scientific Projects, National Institutes of Health*, http://commons.cit.nih.gov (2002) Abstract.

Schade, M., et al., "Structure-Function Analysis of the Z-DNA-Binding Domain Zα of dsRNA Adenosine Deaminase Type I Reveals Similarity to the (α+β) Family of Helix-Turn-Helix Proteins," *The EMBO Journal*, 18:470-479 (1999).

Schade, M., et al., "The Solution Structure of the Zα Domain of the Human RNA Editing Enzyme ADAR1 Reveals a Prepositioned Binding Surface for Z-DNA," *Proceedings of the National Academy of Sciences U.S.A.*, 96:12465-12470 (1999).

Schwartz, T., et al., "Crystal Structure of the Zα Domain of the Human Editing Enzyme ADAR1 Bound to Left-Handed Z-DNA," *Science*, 284:1841-1845 (1999).

Schwartz, T., et al., "Proteolytic Dissection of Zab, the Z-DNA-Binding Domain of Human ADAR1," *The Journal of Biological Chemistry*, 274:2899-2906 (1999).

Schwartz, T., et al., "Structure of the DLM-1-Z-DNA Complex Reveals a Conserved Family of Z-DNA-Binding Proteins," *Nature Structural Biology*, 8:761-765 (2001).

Schors, S.T., et al., "Role of the Vaccinia Virus E3L and K3L Gene Products in Rescue of VSV and EMCV from the Effects of IFN-α, " *Journal of Interferon and Cytokine Research*, 18:721-729 (1998).

Uvarova, E.A. and Shchelkunov, S.N., "Species-Specific Differences in the Structure of Orthopoxvirus Complement-Binding Protein," *Virus Research*, 81:39-45 (2001).

\* cited by examiner

FIG. 1A (SEQ ID NO: 1)
mskiyiders naeivceaik tigiegataa qltrqlnmek revnkalydl
qrsamvyssd dipprwfmtt eadeadadam sdviiddvsr eksmredhks
fddvipakki idwkganpvt vineycqitr rdwsfriesv gpsnsptfya
cvdidgrvfd kadgkskrda knnaaklavd kllgyviirf FIG. 1B (SEQ ID NO: 2)
mskiyiders daeivceaik niglegvtav qltrqlnmek revnkalydl
qrsamvyssd dipprwfmtt eadkpdamtm adviiddvsr eksmredhks
fddvipakki idwknanpvt iineycqitk rdwsfriesv gpsnsptfya
cvdidgrvfd kadgkskrda knnaaklavd kllgyviirf FIG. 1C (SEQ ID NO: 3)
macecaslil ellrksddkl pakqiakelg iskheanrql yrlldsdevc
cedgnpprwf vecapsapte edensdtepm eteagcdtlf ggdidimtqs
avirlkslnp vsavnefcmm trrslefcet rsggedhcpr ftctitisgk
vvaaadgask klarhtacss altilinncg isf FIG. 1D (SEQ ID NO: 4)
mdllsctvnd aeifslvkke vlslntndyt taislsnrlk inkkkinqql
yklqkedtvk mvpsnppkwf knyncdngek hdskleqknh ipnhifsdtv
pykkiinwkd knpcivlney cqftcrdwsi dittsgkshc pmftatviis
gikfkpaign tkreakynas kitmdeilds viikf

FIG. 9A pLacZcOp-(dC-dG)$_n$
n = 0, 4, 5, 9, 12 pLacZcSm-(dC-dG)$_n$
n = 0, 4, 5, 9, 12

AD: Gal4 activation domain
Min. P. CYC1: minimal promoter from *CYC1* gene

METHOD OF INHIBITING PATHOGENICITY OF INFECTIOUS AGENTS

RELATED APPLICATION

This application claims the benefit of U.S. Provisional Application No. 60/343,028 filed on Dec. 20, 2001. The entire teachings of the above application are incorporated herein by reference.

GOVERNMENT SUPPORT

The work described herein was supported, in whole or in part, by Grant No. 5R37-CA04186-43 and Grant No. 1-R21-AI053320-01 from the National Institutes of Health. The Government has certain rights in the invention.

BACKGROUND OF THE INVENTION

Infectious diseases are responsible for the deaths of million of people every year. Although the use of vaccines and drug therapies has decreased mortality due to infectious diseases in developed countries, infectious diseases continue to be the leading cause of death in third world countries. In addition, many infectious diseases emerge or re-emerge in developed countries every year.

Recently, the public has become concerned about infectious agents for a number of additional reasons. The risk of bioterrorism, in which the public is exposed to biological agents, such as pathogenic organisms or agricultural pests for terrorist purposes increases in times of violence and war around the world. In addition, with the ever increasing number of people traveling to diverse regions of the world, infectious diseases once confined to distinct geographic areas can be spread to distant locations. In short, infectious diseases are a constant potential source for deterioration of the health of the population at large.

A number of treatments currently exist for some, but not all infectious agents. For some infectious diseases, for example, viruses including chickenpox, approaches to control focus on prevention of viral diseases, for example, by vaccination. Unfortunately, people or populations may not have been vaccinated and vaccines may not have been developed or may not be readily available (e.g., have not been stockpiled) for many viruses and infectious agents. Therefore there is a need for agents that can be used to treat infections. In addition, it is advantageous to develop therapeutics against new targets, in order to treat the deleterious effects of forms of infectious agents that have become resistant to presently available therapeutics, as well as those infectious agents that have been mutated or biologically altered.

SUMMARY OF THE INVENTION

The present invention relates to a method of detecting and/or identifying an inhibitor of binding of a Z-DNA binding ligand to Z-DNA. The method involves combining an agent to be tested, Z-DNA and a composition comprising a Z-DNA binding ligand or Z-DNA binding variant thereof under conditions suitable for binding of the Z-DNA binding ligand or variant thereof to the Z-DNA, and detecting the formation of a complex between the Z-DNA binding ligand or variant thereof and the Z-DNA. Inhibition of formation of the complex by the agent relative to a suitable control is indicative that the agent is an inhibitor.

In another aspect, the present invention features a method of detecting and/or identifying an inhibitor of binding of a Z-DNA binding ligand to Z-DNA. The method involves contacting a cell comprising a Z-DNA binding ligand or Z-DNA binding variant thereof and Z-DNA with an agent to be tested, under conditions suitable for binding of the Z-DNA binding ligand or variant thereof to the Z-DNA, and detecting the formation of a complex between the Z-DNA binding ligand or variant thereof and the Z-DNA. Inhibition of formation of the complex by the agent relative to a suitable control is indicative that the agent is an inhibitor.

In another aspect, the invention features a pharmaceutical composition comprising an inhibitor identified according to the above methods and a physiologically acceptable carrier.

In still another aspect, the invention features a method of detecting and/or identifying an anti-infective agent. The method involves combining an agent to be tested, Z-DNA and a composition comprising a Z-DNA binding ligand or Z-DNA binding variant thereof under conditions suitable for binding of the Z-DNA binding ligand or variant thereof to the Z-DNA, and detecting the formation of a complex between the Z-DNA binding ligand or variant thereof and the Z-DNA. Inhibition of formation of the complex by the agent relative to a suitable control is indicative that the agent is an anti-infective agent. Pharmaceutical compositions comprising an anti-infective agent identified according to the method and a physiologically acceptable carrier are also provided.

In still another aspect, the invention features a method of detecting and/or identifying an anti-infective agent. The method involves contacting a cell comprising a Z-DNA binding ligand or Z-DNA binding variant thereof and Z-DNA with an agent to be tested, under conditions suitable for binding of the Z-DNA binding ligand or variant thereof to the Z-DNA, and detecting the formation of a complex between the Z-DNA binding ligand or variant thereof and the Z-DNA. Inhibition of formation of the complex by the agent relative to a suitable control is indicative that the agent is an anti-infective agent. Pharmaceutical compositions comprising an anti-infective agent identified according to the method and a physiologically acceptable carrier are also provided.

In another aspect, the invention features a method of detecting and/or identifying an anti-infective agent, comprising from a database of candidate compounds containing docking information, sampling one or more candidate compounds and assessing whether the candidate compounds are capable of forming a complex with a target Z-DNA binding ligand or functional variant thereof, and identifying a conformation of a candidate compound suitable for docking to the target Z-DNA binding ligand, wherein identification of the conformation of the candidate compound is indicative that the candidate compound is an anti-infective agent. In one embodiment, the compound database comprises information for calculating interaction energy between the candidate compounds and the target Z-DNA binding ligand. In another embodiment, the compound database comprises information for generating one or more conformations of the candidate compounds in the database. In another embodiment, identifying a conformation of a candidate compound suitable for docking to the target Z-DNA binding ligand comprises consideration of all possible binding modes and conformations of the candidate compound to identify a compound that optimally docks to the target Z-DNA binding ligand.

In another aspect, the invention features a kit for detecting and/or identifying an anti-infective agent comprising a Z-DNA binding ligand or Z-DNA binding variant thereof, a nucleic acid and a suitable Z-DNA formation buffer.

The invention further relates to a method of inhibiting the pathogenicity of an infectious agent in a subject, involving administering to the subject an effective amount of a therapeutic agent that inhibits binding of a Z-DNA binding ligand or Z-DNA binding variant thereof to Z-DNA. Such methods can be used to treat infection by a number of agents, including viruses, such as vaccinia virus and variola virus, as well as bacteria, fungi, and parasites.

In addition, the present invention relates to methods of treating a subject having an infectious disease, comprising administering to the subject an effective amount of an agent that inhibits binding of a Z-DNA binding ligand or Z-DNA binding variant thereof to Z-DNA. Infectious diseases that can be treated according to the present invention include viral infections, such as poxvirus infection, bacterial infections, fungal infections, and parasitic infections.

The present invention further relates to methods of antiviral therapy, comprising administering to a subject in need thereof a therapeutically effective amount of an agent that inhibits binding of a Z-DNA binding ligand or Z-DNA binding variant thereof to Z-DNA.

BRIEF DESCRIPTION OF THE DRAWINGS

FIG. 1A shows the amino acid sequence of E3L from an isolate of Vaccinia virus (SEQ ID NO:1)(GenBank Accession Number: S64006 Yuwen, et al. J. Virol., 195(2): 732–744, 1993), the teachings of which are incorporated herein by reference).

FIG. 1B shows the amino acid sequence of E3L from an isolate of Variola virus (SEQ ID NO:2)(GenBank Accession Number: X69198.1, the teachings of which are incorporated herein by reference).

FIG. 1C shows the amino acid sequence of E3L from an isolate of Orf virus (SEQ ID NO:3)(GenBank Accession Number: CAA10952, the teachings of which are incorporated herein by reference).

FIG. 1D shows the amino acid sequence of E3L from an isolate of Yaba-like disease virus (SEQ ID NO:4)(GenBank Accession Number: AJ293568, see also GenBank Accession Number: NC002642.1, the teachings of which are incorporated herein by reference).

FIG. 9A is a graph of the lethality of vaccinia virus or variants in mice (percent survival). Experiments analogous to those described in FIG. 4A were carried out on the E3L gene of wild type vaccinia virus. Dose response curves are shown of the lethality following intra-cranial inoculation monitored for two weeks for different doses of the virus. Results are shown for both the virus containing wild type E3L and for virus containing Y48F and Y48A mutations.

B-DNA (open circles) and salt-induced (4 M NaCl) Z-DNA (solid circles) spectra of poly (dC-dG) were shown for comparison.

Figure 15:
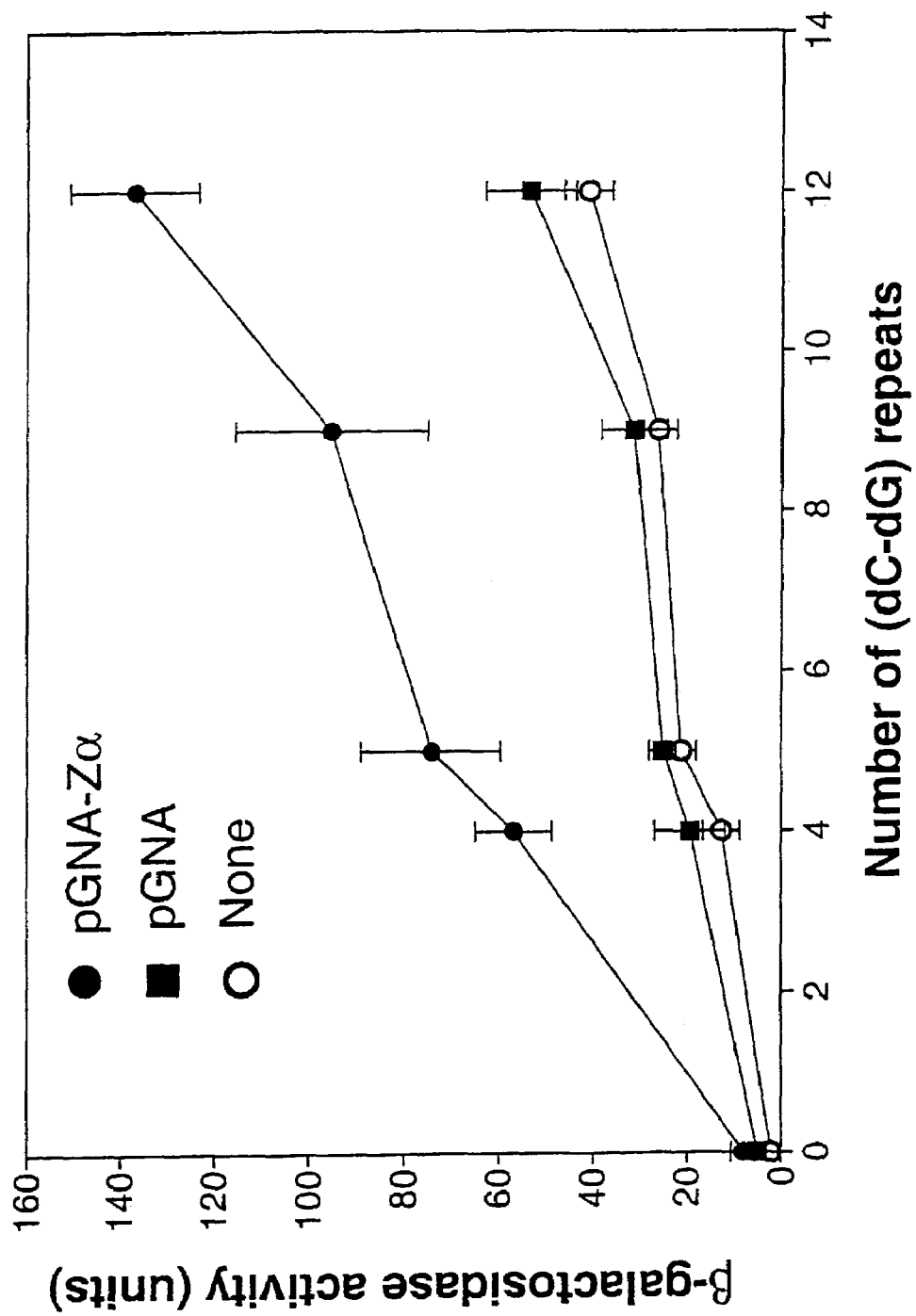

FIG. 15 shows a graph of the activation of transcription of the reporter gene LacZ, by Zα as assessed by measuring β-galactosidase activity. Expression of Zα alone without the Gal4 activation domain was examined. pGNA-Zα expressed Zα with the SV40 T-antigen nuclear localization signal at the N-terminus (described herein). Experiments were performed with different pLacZcOp-(dC-dG)$_n$ reporters. hZαADAR expression increased β-galctosidase activity significantly as stretches of dC-dG became longer.

DETAILED DESCRIPTION OF THE INVENTION

Viruses are obligate intracellular parasites of a living, but noncellular nature, typically comprising DNA or RNA and a proteinaceous coat. The majority of viruses are recognized by the diseases they cause in infected animals or plants. One type of virus that can be particularly detrimental to populations are the poxviruses. Pox viruses are very large, brick-shaped viruses about 300×200 nm (the size of small bacteria). They have a complex internal structure of a large double-stranded DNA genome (about 200 kbp in size) enclosed within a core that is flanked by 2 lateral bodies. The surface of the virus particle is covered with filamentous protein components. The entire particle is enclosed in an envelope derived from the host cell membranes. Laboratory diagnosis of poxviruses may be undertaken by electron microscopy of negatively stained vesicle fluid or lesion material. Some poxviruses can be cultured on the chorioallantoic membrane of chick embryos, where they form pocks, and some can be isolated by cellculture.

Most poxviruses are host-species specific, but vaccinia is an exception. Vaccinia virus is the prototypical large double-stranded DNA virus, encoding approximately 190 genes. E3L is one of the key interferon (IFN) resistance genes in vaccinia virus, and E3L is required for vaccinia virus replication in a wide range of host cells. The E3L gene encodes a 190 amino acid protein with a highly conserved carboxy terminal double-stranded RNA-binding domain (FIG. 1A). This double-stranded RNA-binding domain is required for both the interferon-resistance and the broad host range phenotype of vaccinia virus.

One type of poxvirus that can be particularly harmful to humans is smallpox. Smallpox is caused by variola virus. Smallpox is easily spread from one person to another by infected saliva droplets that expose a susceptible person having face-to-face contact with the ill person. Smallpox can also spread through infected bedding and clothing. The incubation period is about 12 days (range: 7 to 17 days) following exposure to variola virus. Initial symptoms of smallpox include high fever, fatigue, and head and back aches. A characteristic rash, most prominent on the face, arms, and legs, follows in 2–3 days. The rash starts with flat red lesions that evolve at the same rate. Lesions become pus-filled and begin to crust early in the second week. Scabs develop and then separate and fall off after about 3–4 weeks. The majority of patients with smallpox recover, but death occurs in up to 30% of cases.

Once a person is infected with smallpox, there is no cure. Patients with smallpox can benefit from supportive therapy (intravenous fluids, medicine to control fever or pain, etc.) and antibiotics for any secondary bacterial infections that occur. Vaccination against smallpox used to be routine, but ended in 1972. The level of immunity, if any, among persons who were vaccinated before 1972 is uncertain; therefore, these persons are assumed to be susceptible. Clearly, it would be advantageous to have an effective therapy for treating not only those diagnosed with a poxvirus infection, but also those who may have come into contact with someone who has small pox (shares the same air or belongings as person infected with a poxvirus, for example, in an office, home, store, airplane, classroom, or public transportation).

The present invention solves the long felt need to identify and provide the public with therapeutics to treat infectious diseases, for example, poxvirus infection. As described herein, one mechanism for infectious agent pathogenicity is complex formation between Z-DNA and Z-DNA binding ligands, for example, E3L of vaccinia and variola virus. Accordingly, inhibition of such interactions can be used to prevent this complex formation to inhibit the pathogenicity of an infectious agent and to treat an infectious disease.

By "Z-DNA" is meant a DNA molecule with a left-handed double helical conformation of nucleotides that is conformationally distinct from right-handed B-DNA. A Z-DNA helix can be built from a dinucleotide repeat with deoxycytidines in the anti conformation and deoxyguanosines in the unusual syn form. Z-DNA molecules have a single narrow groove that corresponds to the minor groove of B-DNA, and does not have a major groove. Z-DNA is a higher energy conformer of DNA and can be stabilized in vitro by isomerization from B-DNA under conditions including negative supercoiling, high salt, divalent cations, and polyanions. In one embodiment, Z-DNA can be formed in vitro by the isomerization of B-DNA into Z-DNA under physiological salt conditions and 5-methylation of deoxycytidine, as described by Behe et al. (Proc. Natl. Acad. Sci. USA, 78:1619–1623, 1981; the teachings of which are incorporated herein reference). In another embodiment, Z-DNA, for example, in the form of an oligonucleotide in vitro, is stabilized by bromination (Herbert and Rich, Nucleic Acids Research, 21:2669–2672, 1996; the teachings of which are incorporated herein by reference).

Nucleic acid molecules containing (dC-dG) sequences form Z-DNA more readily than other alternating sequences. Z-DNA sequences can be formed in vitro, for example, by generating a plasmid that contains a $(dC\text{-}dG)_n$ insert, where n is approximately 2 or more, for example 2–12, as described by Kim et al. (Proc. Natl. Acad. Sci. USA, 94:12875–12879, 1997; the teachings of which are incorporated herein by reference). The $(dC\text{-}dG)_n$ insert in such plasmids forms Z-DNA in negatively supercoiled plasmids at bacterial superhelical density ($\sigma \approx -0.055$), but is in the B-DNA conformation when the plasmid is linearized or relaxed with topoisomerases. The presence of Z-DNA in a nucleic acid sample in a plasmid can be detected, for example, by measuring the plasmid superhelical density using standard techniques.

In prokaryotic systems, for example, growing *E. coli* cells, the presence of Z-DNA can be detected through a method involving the use of potassium permanganate, as described by Jiang et al. (Nucleic Acids Research, 19:6943–6948, 1991; the teachings of which are incorporated herein by reference). Briefly, potassium permanganate selectively reacts with B-DNA/Z-DNA or Z-DNA/Z-DNA junction regions in supercoiled plasmids harbored in the cells. Restriction enzyme recognition sites located at these junctions are not cleaved by the corresponding endonuclease after modification with potassium permanganate. This inhibition of cleavage allows the determination of the relative amounts of B- and Z-forms of the cloned inserts inside the cell.

As used herein, an "infectious agent" or "infective agent" is an agent or pathogen that multiplies and produces an injurious effect, for example, pathogenicity to the infected host. Examples of infectious agents include bacteria, fungi, viruses, and parasites.

As used herein, "pathogenesis" or "pathogenicity" is any symptom or condition caused by an infectious agent, for example, a virus. Examples of symptoms or conditions caused by infections agents include fever, fatigue, aches (e.g., head, back, muscle ache or pain), rash, lesions, and death.

As used herein, an "anti-infective agent" is a naturally-occurring or artificially-derived agent, and includes, for example, peptides, proteins, synthetic molecules, for example, synthetic organic molecules, naturally-occurring molecules, for example, naturally occurring organic molecules, nucleic acid molecules, and components thereof that inhibits (reduces or prevents) infection and/or pathogenicity, by an infectious agent. Examples of anti-infective agents include antibacterial agents, antifungal agents, agents, antiviral agents, and antiparasitic agents. Anti-infective agents can be isolated or purified.

Identification of Inhibitors of Z-DNA Binding Ligands to Z-DNA

As used herein, a "Z-DNA binding ligand" is a substance that binds to Z-DNA, thereby forming a Z-DNA binding ligand-Z-DNA complex. In a preferred embodiment, binding of a Z-DNA binding ligand to Z-DNA occurs with high affinity. The term Z-DNA binding ligand refers to substances including, but not limited to, a natural ligand, whether isolated, purified, synthetic, and/or recombinant, a homolog of a natural ligand (e.g., from another mammal), nucleic acids, antibodies, portions of such molecules, and other substances which bind Z-DNA. A natural ligand of Z-DNA can bind to Z-DNA under physiological conditions.

In one embodiment, a Z-DNA binding ligand is a protein comprising a Z-DNA binding domain. As used herein, a "protein comprising a Z-DNA binding domain" refers to a naturally occurring protein comprising a Z-DNA binding domain (e.g., Zα domain), polymorphic or allelic variants thereof, other isoforms (e.g., produced by alternative splicing or other cellular processes), and modified (e.g., lipidated, glycosylated, unglycosylated) or unmodified forms of the foregoing. Also included are forms of such proteins having the same amino acid sequence (e.g., recombinant proteins, synthetic proteins (produced using the methods of synthetic organic chemistry)).

"Functional variants" of a protein comprising a Z-DNA binding domain include fragments, mutant proteins and/or chimeric (fusion) proteins which bind Z-DNA (retain Z-DNA binding activity of the protein in whole or in part). Such variants can be produced using suitable methods (e.g., mutagenesis (for example, chemical mutagenesis, radiation mutagenesis), recombinant DNA techniques). Generally, fragments or portions of a protein comprising a Z-DNA binding domain include those having a deletion (i.e., one or more deletions) of an amino acid (i.e., one or more amino acids) relative to the protein (such as N-terminal, C-terminal or internal deletions). Fragments or portions in which contiguous amino acids have been deleted and/or in which non-contiguous amino acids have been deleted relative to a selected protein comprising a Z-DNA binding domain are envisioned.

Mutant proteins comprising a Z-DNA binding domain include natural or artificial variants differing from the protein by insertion (e.g., fusion), substitution, inversion, deletion and/or truncation of one or more contiguous and/or non-contiguous amino acid residues. Such mutations can occur at one or more sites on a protein, for example, in conserved or nonconserved regions (compared to other proteins comprising a Z-DNA binding domain).

Chimeric or fusion proteins are also envisioned. In one embodiment, a first moiety (e.g., a protein comprising a Z-DNA binding domain or a variant thereof) is linked via a covalent bond (e.g., a peptide bond) to a second moiety, such as an amino acid, oligopeptide or polypeptide. The second moiety can be linked to the first moiety at a suitable position, for example, the N-terminus, the C-terminus or internally. In one embodiment, the fusion protein comprises a detectable label (e.g., an enzyme label (glutathione-S-transferase (GST)), fluorescent protein (e.g., Green Fluorescent Protein (GFP)), an antigen or epitope tag (e.g., hemagglutinin (HA), FLAG peptide), a binding domain) as the second moiety, optionally joined to the first moiety via a (one or more) linker sequence. Additional (e.g., third, fourth) moieties can be present as appropriate.

In one embodiment, a functional variant of a protein comprising a Z-DNA binding domain binds Z-DNA and shares at least about 85% amino acid sequence identity with said protein, preferably at least about 90% amino acid sequence identity, and more preferably at least about 95% amino acid sequence identity with said protein. In another embodiment, a functional fusion protein binds Z-DNA and comprises a first moiety which shares at least about 85% amino acid sequence identity, preferably at least about 90% sequence identity, and more preferably at least about 95% sequence identity, with a protein comprising a Z-DNA binding domain (e.g., vaccinia or variola E3L, as shown in FIGS. 1A and 1B, respectively). In a further embodiment, a protein comprising a Z-DNA binding domain or functional variant thereof shares at least about 85% amino acid sequence identity, preferably at least about 90% amino acid sequence identity, and more preferably at least about 95% amino acid sequence identity, with vaccinia virus E3L or with the Z-DNA binding domain of E3L (GenBank Accession Number: S64006) or variola virus E3L (GenBank Accession Number: X69198.1).

For comparison of polypeptides, the length of sequences for comparison will generally be at least 10 amino acids, preferably, at least 15 amino acids, more preferably, at least 20 amino acids, and most preferably, the full length of the Z-DNA binding domain of the polypeptide or the full length of the entire polypeptide.

By a "Z-DNA binding domain" is meant a polypeptide, having a primary, secondary, and/or tertiary structure that allows binding of the polypeptide to Z-DNA. In one embodiment, a Z-DNA binding domain comprises an amino acid sequence that is at least about 50%, 60%, 70%, 80%, 85%, 90% or 95% identical to the consensus amino sequence K[K/R]XXN[R/K]XXY[X]$_{13}$[T/I]PPXW (SEQ ID NO:5), where X (Xaa) is any amino acid.

Comparison of two protein sequences or two nucleic acid sequences can be accomplished by well-known methods, for example, using a mathematical algorithm. A preferred, non-limiting example of such a mathematical algorithm is described in Karlin et al. (Proc. Natl. Acad. Sci. USA, 90:5873–5877, 1993; the teachings of which are incorporated herein by reference). Such an algorithm is incorporated into the BLASTN and BLASTX programs (version 2.2) as described in Schaffer et al. (Nucleic Acids Res., 29:2994–3005, 2001; the teachings of which are incorporated herein by reference). When utilizing BLAST and Gapped BLAST programs, the default parameters of the respective programs (e.g., BLASTN) can be used. See, for example the BLAST program which can be accessed through the Internet site for the National Center for Biotechnology Information, as available on Dec. 17, 2001. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Another preferred, non-limiting example of a mathematical algorithm utilized for the comparison of sequences is the algorithm of Myers and Miller, CABIOS (1989). Such an algorithm is incorporated into the ALIGN program (version 2.0), which is part of the GCG (Accelrys) sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (Comput. Appl. Biosci., 10:3–5, 1994; the teachings of which are incorporated by reference); and FASTA described in Pearson and Lipman (Proc. Natl. Acad. Sci USA, 85:2444–8, 1988; the teachings of which are incorporated by reference).

The invention also encompasses variants of Z-DNA binding ligands having a Z-DNA binding domain having a lower degree of identity but having sufficient similarity so as to be a functional variant of a Z-DNA binding domain (i.e., capable of performing one or more of the same functions performed by an Z-DNA binding ligand, for example, forming a complex with Z-DNA). Similarity can be determined, for example, by conservative amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent can be found in Bowie et al. (Science, 247:1306–1310, 1990).

Examples of Z-DNA binding ligands include E3L, DLM-1, and ADAR1, as well as portions of these proteins that bind Z-DNA (for example, Zα and Zαβ, as described by Kim et al., J. Biol. Chem., 274:19081–19086, 1999). In addition, polypeptides which bind Z-DNA and have at least about 50%, 60%, 70%, 80%, 85%, 90% or 95% amino acid sequence identity to any one of E3L, DLM-1 (GenBank Accession Number: AJ300575), hADAR1 (GenBank Accession Number: U18121), Zα of hADAR1 (amino acids from about 129 to about 196 of hADAR1), or Zap of hADAR1 (amino acids from about 129 to about 368 of hADAR1) are also Z-DNA binding ligands. Other proteins, for example, the Zβ domain of ADAR1 can be mutated (e.g., as described herein) such that the protein binds to Z-DNA.

Methods for identifying Z-DNA binding ligands are known in the art, and are described for example by Kim et al., J. Biol. Chem., supra; Kim et al., Proc. Natl. Acad. Sci. USA, supra; and Herbert et al., Nucleic Acids Research, 26:3486–3493, 1998; the teachings of which are each incorporated herein by reference. These methods, which involve gel shift assays, Z-DNA specific nuclease assays, and circular dichroism assays, or other suitable assays can be used to assess the Z-DNA binding activity of a Z-DNA binding ligand or variant. Other assays include yeast one-hybrid assays and B-Z midpoint assays, as described herein.

As used herein, an "inhibitor" is an agent that acts by inhibiting (preventing or decreasing) at least one function characteristic of the interaction between a Z-DNA binding ligand and Z-DNA, such as a binding activity (complex formation), cellular signaling triggered by the interaction and/or cellular response function (e.g., pathogenicity) mediated by the interaction. The term inhibitor includes agents that bind either Z-DNA (Z-DNA antagonists) or a Z-DNA binding ligand (Z-DNA binding ligand antagonist) (e.g., an antibody, a mutant of a natural ligand, a peptidomimetic, and other competitive inhibitors of ligand binding), and to substances that inhibit a function mediated by complex formation between a Z-DNA binding ligand or Z-DNA binding ligand variant thereof and Z-DNA without binding thereto (e.g., an anti-idiotypic antibody). In one embodiment, the inhibitor is not an antibody or an antigen-binding fragment. In another embodiment, the inhibitor is an agent other than an antibody or antigen-binding fragment thereof that binds Z-DNA. In a particular embodiment, the inhibitor is an agent other than antibody Z22, Z44 or antigen-binding fragments thereof (Brigido et al., J. Immunol., 146:2005–2009, 1991). Preferably, the inhibitor inhibits complex formation between a Z-DNA binding ligand and Z-DNA by at least about 10% 25%, 50%, 60%, 70%, 80% 90% or 100% compared to a suitable control (e.g., a sample receiving no inhibitor or receiving the inhibitor vehicle only).

In one embodiment, the invention provides assays for screening candidate inhibitors or test agents (e.g., a candidate compound) to detect and/or identify those that inhibit at least one function characteristic of the interaction between a Z-DNA binding ligand and Z-DNA, as described herein, as well as agents identifiable by the assays. As used herein, a "candidate inhibitor" or "test agent" is a molecule, be it naturally-occurring or artificially-derived, and includes, for example, peptides, proteins, peptidomimetics, synthetic molecules, for example, synthetic organic molecules, naturally-occurring molecules, for example, naturally occurring organic molecules, nucleic acid molecules, and components thereof.

In general, test agents for use in the present invention may be identified from libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic small molecule libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.).

In addition, natural and synthetically produced molecules or libraries can be generated by any suitable method (e.g., by standard extraction and fractionation methods). For example, candidate compounds can be obtained using any of the numerous approaches in combinatorial library methods, including biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide libraries, while the other four approaches are applicable to polypeptide, non-peptide oligomer or small molecule libraries of compounds (Lam, Anticancer Drug Des., 12:145, 1997). Furthermore, if desired, any library or compound can be readily modified using standard chemical, physical, or biochemical methods.

It is understood that an inhibitor can inhibit a function characteristic of the interaction between a Z-DNA binding ligand and Z-DNA in varying degrees. For example, the inhibitor can decrease the function characteristic of the interaction between a Z-DNA binding ligand and Z-DNA by at least about 10%, 40%, 50%, or 75%, or by at least about 90%, relative to an appropriate control.

When a crude extract is found to inhibit a function characteristic of the interaction between a Z-DNA binding ligand and Z-DNA, further fractionation of the positive lead extract can be performed to isolate chemical constituents responsible for the observed effect. The assays described herein for the detection and/or identification of activities in mixtures of compounds can be used to purify the active component or to test derivatives thereof. If desired, compounds shown to be useful agents for treatment can be chemically modified according to methods known in the art. Compounds identified as being of therapeutic value may be subsequently analyzed using animal models for diseases in which it is desirable to alter a function characteristic of the interaction between a Z-DNA binding ligand and Z-DNA.

Binding Inhibition Assays

Binding inhibition assays can be carried out using any suitable method. Such assays can be used, alone or in combination with each other or other suitable methods, to identify inhibitors of a function characteristic of the interaction between a Z-DNA binding ligand and Z-DNA (e.g., an anti-infective agent). The methods of the present invention can be adapted for high-throughput screening in which large numbers of samples are processed (e.g., a 96 well format).

Binding inhibition assays can be used to identify inhibitors that bind to a Z-DNA binding ligand, variant thereof or Z-DNA and inhibit binding of a Z-DNA binding ligand to Z-DNA. For example, a binding assay can be conducted in which the binding of a Z-DNA binding ligand to Z-DNA in the absence of a candidate inhibitor, is compared with the binding of the Z-DNA binding ligand to Z-DNA in the presence of the candidate inhibitor. Z-DNA can be contacted with a Z-DNA binding ligand and the candidate inhibitor simultaneously, or one after the other, in either order. A reduction in the extent of binding of the Z-DNA binding ligand to the Z-DNA in the presence of the candidate inhibitor is indicative that the candidate is an inhibitor.

In one method for detection and/or identification of inhibitors, an agent (e.g., a composition comprising one or more candidate inhibitors) to be tested, Z-DNA and a composition comprising a Z-DNA binding ligand or variant thereof can be maintained under conditions suitable for binding and formation of a complex between the Z-DNA binding ligand or variant and Z-DNA is detected or measured. For example, the extent of complex formation can be determined relative to a suitable control (e.g., compared with background determined in the absence of the candidate inhibitor, or compared with complex formation with a second agent (i.e., a standard)).

Complex formation between a Z-DNA binding ligand or variant thereof and Z-DNA can be detected directly or indirectly. In one embodiment, the Z-DNA, candidate inhibitor, or the Z-DNA binding ligand or variant thereof can be labeled with a suitable label (e.g., fluorescent moiety, chemiluminescent group, epitope tag, radioisotope, enzyme label, or affinity tag), and complex formation can be determined by detection of the label (directly or indirectly). Specificity of binding can be assessed by competition or displacement, for example, using unlabeled agent or a ligand (e.g., E3L, ADAR1, DLM-1, or portions thereof) as competitor.

For example, a fusion protein comprising a Z-DNA binding ligand or variant thereof and a detectable label, for example, a fluorescent protein, such as green fluorescent protein, or a hapten that can be detected with an antibody (e.g., labeled antibody), such as glutathione S-transferase or biotin is contacted with Z-DNA. The Z-DNA can be immobilized on a solid support, for example, a microtiter well. Preferably, the Z-DNA and fusion protein are in a solution suitable for complex formation between Z-DNA and a Z-DNA binding ligand or variant, as described herein. The fusion protein binds to Z-DNA. Unbound fusion protein can be removed, for example, by washing the solid support or by other means suitable for separation of unbound fusion protein from bound fusion protein complexed with Z-DNA. The complex formed between the fusion protein and Z-DNA is then detected, for example, by detecting bound fluorescent protein, or by contacting the complex with an antibody that binds the hapten portion of the fusion protein, using, for example, an ELISA assay or a radioimmunoassay. The assay can be repeated in the presence of a candidate inhibitor. If the candidate inhibitor disrupts complex formation between the Z-DNA binding fusion protein and Z-DNA, then a decrease in the signal can be detected due to decreased complex formation between the fusion protein and Z-DNA. Such a decrease indicates that the candidate inhibitor is an inhibitor of Z-DNA binding. Alternatively, the DNA binding ligand can be immobilized on a solid support, and the Z-DNA and candidate inhibitor is added and assessed for complex formation.

In another example, a fusion protein comprising a Z-DNA binding ligand (or variant thereof) and an enzyme, for example, β-galactosidase, luciferase, chloramphenicol acetyl transferase, or alkaline phosphatase, is contacted with Z-DNA. The Z-DNA can be immobilized on a solid support, for example, a microtiter well. Preferably, the Z-DNA and fusion protein are in a solution suitable for complex formation between Z-DNA and a Z-DNA binding ligand or variant, as described herein. The fusion protein will bind to Z-DNA. Unbound fusion protein can be removed, for example, by washing the solid support or by other means suitable for separation of unbound fusion protein from bound fusion protein complexed with Z-DNA. The complex formed between the fusion protein and Z-DNA can be detected, for example, by adding the appropriate substrate for the enzyme present in the fusion protein, and detecting enzyme activity using, for example, using a microplate reader or a luminometer. The assay can be repeated in the presence of a candidate inhibitor. If the candidate inhibitor disrupts complex formation between the fusion protein and Z-DNA, then a decrease in enzyme activity due to decreased complex formation between the fusion protein and Z-DNA can be detected. Such a decrease indicates that the candidate inhibitor is an inhibitor of Z-DNA binding.

Another method for identifying an inhibitor of complex formation between a Z-DNA binding ligand or variant thereof and Z-DNA is through phage display techniques. For example, a Z-DNA binding ligand or variant can be expressed on the surface of phage (e.g., as a fusion protein with a phage coat protein). The phage is then contacted with Z-DNA (immobilized, for example, on a solid support, such as a microtiter well) and the phage binds to the Z-DNA. The complex can be detected using any suitable method. For example, the complex can be contacted with an antibody that recognizes the phage, and binding of the antibody can be detected using, for example, an ELISA assay or a radioimmunoassay. The assay can be repeated in the presence of a candidate inhibitor. If the candidate inhibitor disrupts complex formation between the Z-DNA binding ligand displayed on the phage, then a decrease in signal (e.g., the amount of antibody binding) can be detected due to decreased complex formation between the fusion and Z-DNA. Such a decrease indicates that the candidate inhibitor is an inhibitor of Z-DNA binding.

In addition, the methods described above, for detection of a Z-DNA binding ligand or Z-DNA binding variant thereof, can be adapted for detection of inhibitors of complex formation by adding a candidate inhibitor to the binding reaction and detecting formation of a complex between Z-DNA and a Z-DNA binding ligand or variant.

Cell based assays can also be used to detect and/or identify inhibitors of binding of a Z-DNA binding ligand to Z-DNA. Reporter-based assays, for example, yeast one-hybrid assays (as described, for example, herein) can be used to detect such inhibitors (Li and Herskowitz, Science, 262:1870–1874, 1993). In one example, a promoter region of a gene, containing DNA that forms a "Z" conformation under the reaction conditions (for example, a $(dC-dG)_n$ sequence in a Z-DNA formation buffer) is operably linked to a reporter gene, for example, LacZ. The Z-DNA can be contacted with a fusion protein comprising a Z-DNA binding ligand or variant thereof and a transcriptional transactivation protein or transactivation domain thereof, for example, Ga14 or VP16. Binding between the fusion protein and Z-DNA induces or enhances expression of the reporter gene. A candidate inhibitor can be added. If the candidate inhibitor inhibits binding of the fusion protein to Z-DNA, then expression of the reporter gene will be inhibited as well, which indicates that the candidate inhibitor is an inhibitor of Z-DNA binding. This assay can be carried out in any suitable cell, for example, fungal or yeast cells, including *Pichia pastoris, Aspergillus* species, *Saccharomyces cerevisiae, Schizosacccharomyces pombe, Neurospora crassa*), or other lower eukaryotic cells, and cell of higher eukaryotes, such as those from insects (e.g., Sf9 insect cells) or mammals (e.g., Chinese hamster ovary cells, COS cells, 293 cells) or any other cell comprising the appropriate components of this reporter-based assay.

Another cell based-assay involves detection of a secreted viral protein in cells infected with an infectious agent. Cells infected with variola or vaccinia virus normally secrete a protein called complement-binding protein (Uvarova and Shchelkunov, Virus Research, 81:39–45, 2001). In cells infected with variola or vaccinia virus in which the amino-terminus of the E3L protein is deleted, secretion of complement binding protein is decreased. An inhibitor of binding of a Z-DNA binding ligand or variant thereof to Z-DNA can be detected by administering to a cell infected with vaccinia or variola virus a candidate inhibitor, and measuring the level of complement-binding factor secreted into the cell culture media, for example, using standard protein detection techniques, such as ELISA or radioimmunoassay. A decrease in secretion of complement-binding factor compared to a suitable control (e.g., a cell sample receiving no candidate inhibitor or receiving candidate inhibitor vehicle only) is indicative that the candidate inhibitor is an inhibitor of binding of a Z-DNA binding ligand to Z-DNA. Any suitable cell can be used to carry out this screening method. Preferably, the cells are mammalian cells, for example human cells. In one example, HeLa cells are used.

In certain embodiments it may be desirable to immobilize (directly or indirectly) a component of the assay on a matrix or other solid support, in order to facilitate separation of bound from unbound components of the assay, as well as to accommodate automation of the assay. The above-described assays can be carried out in any suitable manner for combining the reactants. For example, the components may be combined in a suitable vessel such as a microtiter plate, test tube, or micro-centrifuge tube. In one embodiment, a fusion protein (e.g., a glutathione-S-transferase fusion protein) can be provided that adds a domain that allows a component of the assay to be bound to a matrix or other solid support.

Detection and/or identification of an inhibitor of complex formation between a Z-DNA binding ligand or variant thereof and Z-DNA can also occur through the use of "in silico" screening methods, which involve the use of computer programs to test the docking of candidate inhibitors. Such methods comprise determining functional residues of a Z-DNA binding ligand or variant thereof involved in forming a complex with Z-DNA; developing one or more three-dimensional structures based on the functional residues identified in the previous step using any suitable method; comparing the one or more three-dimensional structures with one or more test agents having calculatable tertiary structures; and identifying agents having a spatial orientation consistent with forming a complex with a Z-DNA binding ligand and inhibition of complex formation between Z-DNA and the Z-DNA binding ligand or variant. Agents identified in this manner can be further assessed for activity and used as anti-infective agents.

Functional residues of Z-DNA binding proteins involved in binding to Z-DNA and in mediating viral pathogenicity have been identified as described herein. Such residues contribute to complex formation with a successful test agent. These functional residues can be used to develop one or more three-dimensional structures with which a successful test agent comes into contact. The three-dimensional structures are compared with or tested against one or more test agents that have calculatable tertiary structures. For example, computer programs in which one or more test agents are individually docked and examined for suitable spatial orientation with respect to the Z-DNA binding ligand can be used to test for an appropriate test agent. A test agent has suitable spatial orientation if the test agent binds to the Z-DNA binding ligand or variant with favorable energy, as determined using the parameters of the computer software used to detect docking of test agents and associated binding energies. Methods for testing the docking of candidate compounds are described in greater detail herein. Successful compounds, or derivatives thereof can then be tested using in vitro or in vivo assays, for example, as described herein.

This invention further pertains to novel compounds identified by the above-described screening assays. Accordingly, it is within the scope of this invention to further use an agent identified as described herein in an appropriate animal model. For example, a compound identified as described herein (e.g., a candidate compound that is an inhibitor of complex formation between a Z-DNA binding ligand and Z-DNA, such as an antibody, a polypeptide, or a small molecule inhibitor) can be used in an animal model to determine the efficacy, toxicity, or side effects of treatment with such a compound, for example, as described below.

Antibodies

Antibodies or an antigen-binding fragment of an antibody can be used to inhibit complex formation between Z-DNA and a Z-DNA binding ligand or variant. The term "antibody" as used herein refers to immunoglobulin molecules and immunologically active portions of immunoglobulin molecules, i.e., molecules that contain an antigen binding site that selectively binds an antigen (e.g., an antigen-binding fragment of an antibody). The antibodies of the present invention are molecules that selectively bind to a Z-DNA binding ligand or variant thereof (e.g., a fragment thereof) or to Z-DNA. In a preferred embodiment, the antibodies do not substantially bind other molecules in a sample. Preferably, the antibody is at least 60%, by weight, free from proteins and naturally occurring organic molecules with which it naturally associated. More preferably, the antibody preparation is at least 75% or 90%, and most preferably, 99%, by weight, antibody.

The invention further relates to antibodies reactive with a Z-DNA binding ligand or variant thereof, or with Z-DNA itself. In one embodiment, antibodies are raised against an isolated and/or recombinant Z-DNA binding ligand or variant thereof (e.g., a protein or a peptide). In a preferred embodiment, the antibodies specifically bind a Z-DNA binding ligand or a variant thereof, and in a particularly preferred embodiment, the antibodies can inhibit (reduce or prevent) the interaction of Z-DNA with a natural ligand, such as E3L, DLM-1, ADAR1 or a Z-DNA binding domain such as $Z\alpha$, or $Z\alpha\beta$.

The antibodies of the present invention can be polyclonal or monoclonal, and the term antibody is intended to encompass both polyclonal and monoclonal antibodies. The terms polyclonal and monoclonal refer to the degree of homogeneity of an antibody preparation, and are not intended to be limited to particular methods of production.

Antibodies of the present invention can be raised against an appropriate immunogen, including proteins or polypeptides of the Z-DNA binding ligands described herein (including synthetic molecules, such as synthetic peptides).

Preparation of immunizing antigen, and polyclonal and monoclonal antibody production can be performed using any suitable technique. A variety of methods have been described (see e.g., Kohler et al., Nature, 256:495–497, 1975 and Eur. J. Immunol. 6:511–519, 1976; Milstein et al., Nature 266:550–552, 1977; Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); and Current Protocols In Molecular Biology, Vol. 2 (Supplement 27, Summer '94), Ausubel, F. M. et al., Eds., (John Wiley & Sons: New York, N.Y., Chapter 11, 1991; the teachings of each of which are incorporated herein by reference). Generally, a hybridoma is produced by fusing a suitable immortal cell line (e.g., a myeloma cell line such as SP2/0) with antibody producing cells. The antibody producing cell, preferably those of the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies (see e.g., Jakobovits et al., Proc. Natl. Acad. Sci. USA, 90:2551–2555, 1993; Jakobovits et al., Nature, 362:255–258, 1993; Lonberg et al., U.S. Pat. No. 5,545,806; and Surani et al., U.S. Pat. No. 5,545,807; the teachings of which are each incorporated herein by reference).

Single-chain antibodies, and chimeric, humanized or primatized (CDR-grafted), or veneered antibodies, as well as chimeric, CDR-grafted or veneered single-chain antibodies, comprising portions derived from different species, and the like are also encompassed by the present invention and the term "antibody." The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B 1; Queen et al., European Patent No. 0 451 216 B1; and Padlan, E. A. et al., EP 0 519 596 A1. See also, Newman, R. et al., BioTechnology, 10:1455–1460, 1992, regarding primatized antibody, and Ladner et al., U.S. Pat. No. 4,946,778 and Bird, R. E. et al., Science, 242:423–426, 1988 regarding single-chain antibodies.

In addition, antigen-binding fragments of antibodies, including fragments of chimeric, humanized, primatized, veneered or single-chain antibodies, can also be produced. Antigen-binding fragments of foregoing antibodies retain at least one binding function and/or modulation function of the full-length antibody from which they are derived. For example, antigen-binding fragments capable of binding to a Z-DNA binding ligand or variant thereof, or to Z-DNA itself, including, but not limited to, Fv, Fab, Fab' and F(ab')$_2$ fragments are encompassed by the invention. Such fragments can be produced by enzymatic cleavage or by recombinant techniques. For instance, papain or pepsin cleavage can generate Fab or F(ab')$_2$ fragments, respectively. Reduction of the disulfide bond between the heavy chains of F(ab')$_2$ fragments can yield F(ab') fragments. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

The antibodies of the present invention can also be used to modulate binding of a Z-DNA binding ligand to Z-DNA, in research and therapeutic applications. In one embodiment, anti-Z-DNA antibody or antigen-binding fragment thereof has the epitopic specificity of antibody Z22 or Z44.

Anti-idiotypic antibodies are also provided. Anti-idiotypic antibodies recognize antigenic determinants associated with the antigen-binding site of another antibody. Anti-idiotypic antibodies can be prepared against a first antibody by immunizing an animal of the same species, and preferably of the same strain as the animal used to produce the first antibody, with said first antibody. See e.g., U.S. Pat. No. 4,699,880.

In one embodiment, antibodies are raised against a Z-DNA binding ligand or a variant thereof or Z-DNA, and these antibodies are used in turn as immunogen to produce an anti-idiotypic antibody (anti-Id). The anti-Id produced thereby can mimic the Z-DNA binding ligand or variant or Z-DNA and bind compounds which bind them, and can be used in an immunoassay to detect, identify or quantitate such compounds. Such an anti-idiotypic antibody can also be an inhibitor of Z-DNA binding ligand/Z-DNA function, although it does not bind a Z-DNA binding ligand or Z-DNA itself.

An anti-idiotypic (i.e., anti-Id) antibody can itself be used to raise an anti-idiotypic antibody (i.e., anti-anti-Id). Such an antibody can be similar or identical in specificity to the original immunizing antibody. In one embodiment, antibody antagonists which block binding of a Z-DNA binding ligand to Z-DNA can be used to raise anti-Id, and the anti-Id can be used to raise anti-anti-Id, which can have a specificity which is similar or identical to that of the antibody antagonist. These anti-anti-Id antibodies can be assessed for inhibitory effect on Z-DNA binding ligand/Z-DNA function to determine if they are antagonists.

Single-chain, and chimeric, humanized, primatized (CDR-grafted), veneered, as well as chimeric, CDR-grafted, or veneered single-chain anti-idiotypic antibodies can be prepared, and are encompassed by the term anti-idiotypic antibody. Antibody fragments of such antibodies can also be prepared.

The antibodies and fragments of the present invention can be modified, for example, by incorporation of or attachment (directly or indirectly) of a detectable label. Examples of detectable labels include various spin labels, antigen or epitope tags, haptens, enzyme labels, prosthetic groups, fluorescent materials, chemiluminescent materials, bioluminescent materials, and radioactive materials. Examples of suitable enzyme labels include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a chemiluminescent material includes luminol; examples of bioluminescent materials include luciferase, luciferin, and aequorin, and examples of suitable radioactive material include $^{125}$I, $^{131}$I, $^{35}$S, and $^3$H.

Methods of Therapy

Modulation of the complex formation between a Z-DNA binding ligand and Z-DNA according to the present invention, through the inhibition of at least one function characteristic of a Z-DNA binding ligand, provides an effective way of inhibiting or promoting Z-DNA binding mediated functions. As E3L is expressed in cells infected with a virus, E3L provides a target for selectively interfering with viral agent pathogenesis in a mammal, such as a human. Thus, agents which inhibit complex formation between Z-DNA and a Z-DNA binding ligand or Z-DNA binding function, including ligands, inhibitors, such as those identified as described herein, can be used as anti-infective agents to treat infectious diseases, for therapeutic purposes.

In one aspect, the present invention provides a method of inhibiting the pathogenicity of an infectious agent in an individual in need of such therapy, comprising administering an effective amount of a therapeutic agent which inhibits complex formation between a Z-DNA binding ligand and Z-DNA to an individual in need of such therapy. In one embodiment, a compound which inhibits one or more functions of a Z-DNA binding ligand is administered to inhibit (i.e., reduce or prevent) pathogenesis. As a result, one or more symptoms of infectious agent pathogenicity, for example, mortality, inflammation, fever, formation of lesions on the skin, emesis, gastrointestinal discomfort, diarrhea, rash, hemorrhaging, and weight loss can be inhibited according to the present method.

The terms "therapeutic" and "treatment" as used herein, refer to ameliorating symptoms associated with a disease, including preventing or delaying the onset of the disease symptoms, and/or lessening the severity or frequency of symptoms of the disease. The term "individual" is defined herein to include animals such as mammals, including, but not limited to, primates (e.g., humans), cows, sheep, goats, horses, dogs, cats, rabbits, guinea pigs, rats, mice or other bovine, ovine, equine, canine, feline, rodent or murine species. Diseases and conditions associated with infectious agent pathogenicity can be treated using the method. In a preferred embodiment, the disease or condition is one in which the actions a cell infected with an infectious agent comprising or having the ability to generate a Z-DNA binding ligand or variant thereof are to be inhibited for therapeutic (including prophylactic) purposes. In a particularly preferred embodiment, the disease or condition is a viral infection.

Diseases or conditions, including chronic diseases, of humans or other mammals or animals which can be treated with inhibitors of binding of a Z-DNA binding ligand or variant to Z-DNA include, but are not limited to:

bacterial diseases, for example, *staphylococcus* infections (caused, for example, by *Staphylococcus aureus, Staphylococcus epidermis*, or *Staphylococcus saprophyticus*), *streptococcus* infections (caused, for example, by *Streptococcus pyogenes, Streptococcus pneumoniae,* or *Streptococcus agalactiae*), enterococcus infections (caused, for example, by *Enterococcus faecalis*, or *Enterococcus faecium*), diphtheria (caused, for example, by *Corynebacterium diptheriae*), anthrax (caused, for example, by *Bacillus anthracis*), listeriosis (caused, for example, by *Listeria monocytogenes*), gangrene (caused, for example, by *Clostridium perfringens*), tetanus (caused, for example, by *Clostridium tetanus*), botulism (caused, for example, by *Clostridium botulinum*), toxic enterocolitis (caused, for example, by *Clostridium difficile*), bacterial meningitis (caused, for example, by *Neisseria meningitidis*), bacteremia (caused, for example, by *Neisseria gonorrhoeae*), *E. coli* infections, including urinary tract infections and intestinal infections, shigellosis (caused, for example, by *Shigella* species), salmonellosis (caused, for example, by *Salmonella* species), yersinia infections (caused, for example, by *Yersinia pestis, Yersinia pseudotuberculosis*, or *Yersinia enterocolitica*), cholera (caused, for example, by *Vibrio cholerae*), campylobacteriosis (caused, for example, by *Campylobacter jejuni* or *Campylobacter fetus*), gastritis (caused, for example, by *Helicobacter pylori*), pseudomonas infections (caused, for example, by *Pseudomonas aeruginosa* or *Pseudomonas mallei*), haemophilus influenzae type B (HIB) meningitis, HIB acute epiglottitis, or HIB cellulitis (caused, for example, by *Haemophilus influenzae*), pertussis (caused, for example, by *Bordetella pertussis*), mycoplasma pneumonia (caused, for example, by *Mycoplasma pneumoniae*), nongonococcal urethritis (caused, for example, by *Ureaplasma urealyticum*), legionellosis (caused, for example, by *Legionella pneumophila*), syphillis (caused, for example, by *Treponema pallidum*), leptospirosis (caused, for example, by *Leptospira interrogans*), Lyme borreliosis (caused, for example, by *Borrelia burgdorferi*), tuberculosis (caused, for example, by *Mycobacterium tuberculosis*), leprosy (caused, for example, by *Mycobacterium leprae*), actinomycosis (caused, for example, by *Actinomyces* species), nocardiosis (caused, for example, by *Nocardia* species), chlamydia (caused, for example, by *Chlamydia psittaci, Chlamydia trachomatis,* or *Chlamydia pneumoniae*), Rickettsial diseases, including spotted fever (caused, for example, by *Rickettsia ricketsii*) and Rickettsialpox (caused, for example, by *Rickettsia akari*), typhus (caused, for example, by *Rickettsia prowazekii*), brucellosis (caused, for example, by *Brucella abortus, Brucella melitensis,* or *Brucella suis*), and tularemia (caused, for example, by *Francisella tularensis*);

viral diseases or conditions caused by infection with any of the following viruses: Influenza Virus (Influenza), Parainfluenza, Respiratory Syncytial Virus (Respiratory Syncytial Virus Infection), Adenoviruses, Rhinoviruses, Coronaviruses, Reoviruses, Mumps Virus (Mumps), Measles Virus (Measles), Rubella Virus (Rubella Infection), Parvovirus B19, Poxviruses, including orthopox viruses such as Variola Virus (Smallpox), Vaccinia Virus, Cowpox Virus, Mousepox Virus, Monkeypox Virus, and Buffalopox Virus, and other pox viruses such as Molluscum Contagiosum Virus, Orf Virus, Pseudocowpox Virus, Enteroviruses, including Poliovirus (Polio), Coxsackievirus, Echovirus, Hepatitis Viruses, including Hepatitis A, Hepatitis B, Hepatitis C, Hepatitis D, and Hepatitis E, Herpesviruses, including Herpes Simplex Virus, Cytomegalovirus, Varicella-zoster Virus (Chickenpox), Herpes Zoster (Shingles), Epstein-Barr Virus (Infectious Mononucleosis), and Human Herpesvirus Type 6 (Roseola), Rotaviruses (intestinal disorders), Norwalk Viruses (intestinal disorders), Togaviruses, Flaviviruses, Bunyaviruses, Reoviruses, Arenaviruses, Arboviruses (Western Equine Encephalitis, Eastern Equine Encephalitis, St. Louis Encehphalitis, California Virus, Yellow Fever, Dengue, Japanese B Encephalitis, Powassan Virus, and Colorado Tic Fever), Filioviruses (Ebola Virus and Marburg Virus), Hantaviruses (Hantavirus Hemorrhagic Fever), Vesicular Stomatitis Viruses, Rabies Viruses (Rabies) Retroviruses, including HIV Viruses, and Papovaviruses, including Papillomaviruses, and Polyomaviruses;

fungal diseases, for example, dermatophytoses (caused, for example, by species or the genera *Microsporum, Trichophyton,* or *Epidermpphyton*), candidiasis (caused, for example, by *Candida albicans, Candida krusei, Candida parapsilosis, Candida tropicalis,* or *Candida guilliermondii*), aspergilliosis (caused, for example, by *Aspergillus* species), zygomycosis (caused, for example, by *Absidia, Phizopus,* and *Mucor zygomycetes*), blastomycosis (caused, for example, by *Blastomyces dermatitidis*), cryptococcosis (caused, for example, by *Cryptococcus neoformans*), histoplasmosis (caused, for example, by *Histoplasma capsulatum*), coccidioidomycosis (caused, for example, by *Coccidioides immitis*), sporotrichosis (caused, for example, by *Sporothrix schenckii*) and pneumocystosis (caused, for example, by *Pneumocystis carini*); and parasitic diseases, for example, helminthic diseases, such as enterobiasis (caused, for example, by *Enterobius vermicularis*), trichuriasis (caused, for example, by *Trichuris trichuria*), ascariasis (caused, for example, by *Ascaris lumbricoides*), hookworm disease (caused, for example, by *Necator americanus* and *Necator duodenale*), cryptosporidiosis (caused, for example, by *Cryptosporidium parvum*), amebiasis (caused, for example, by *Entamoeba histolytica*), amebic meningoencephalitis (caused, for example, by amebas of the *Naegleria* and *Ancanthamoeba* genera), toxoplasmosis (caused, for example, by *Toxplasma gondii*), malaria (caused, for example, by *Plasmodium vivax, Plasmodium ovale, Plasmodium malariae,* or *Plasmodium falciparum*), trichomoniasis (caused, for example, by *Trichomonas vaginalis*), giardiasis (caused, for example, by *Giardia lamblia*), leishmaniasis (caused, for example, by *Leishmania tropica, Leishmania mexicana, Leishmania braziliensis, Leishmania donovani*), African trypanosomiasis (caused, for example, by flies of the genus *Glossina*), and American trypanosomiasis (caused, for example, by *Trypanosoma cruzi*).

The present invention also feature a method of producing a vaccine composition, comprising reducing the pathogenicity of an infective agent which comprises a gene encoding a Z-DNA binding ligand, by producing a derivative of the infective agent which comprises a variant of the gene encoding a protein having reduced Z-DNA binding activity relative to that of said Z-DNA binding protein; and preparing a vaccine composition comprising said derivative. Such Z-DNA binding ligands that exhibit reduced Z-DNA binding capacity and/or reduced pathogenicity in vivo are described herein, and these ligands can be used in vaccine compositions. Such vaccines can be used therapeutically and/or for research purposes (e.g., to identify therapeutic agents that can reducing the pathogenicity of an infective agent).

Modes of Administration

According to the method, an (i.e., one or more) anti-infective or therapeutic agent can be administered to the host by an appropriate route, either alone or in combination with another drug. An effective amount of an anti-infective or therapeutic agent is administered. An effective amount is an amount sufficient to achieve the desired therapeutic or prophylactic effect, under the conditions of administration, such as an amount sufficient for inhibition of complex formation between a Z-DNA binding ligand or variant thereof and Z-DNA, thereby inhibiting infectious agent pathogenicity.

A variety of routes of administration are possible including, but not necessarily limited to oral, intranasal, intraocular, dietary, topical, parenteral (e.g., intravenous, intraarterial, intramuscular, intradermal, intraperitoneal, subcutaneous injection), and inhalation (e.g., intrabronchial, intranasal or oral inhalation, intranasal drops) routes of administration, depending on the agent and disease or condition to be treated.

Formulation of an anti-infective or therapeutic agent to be administered will vary according to the route of administration selected (e.g., solution, emulsion, capsule). An appropriate composition comprising the agent to be administered can be prepared in a physiologically or pharmaceutically acceptable vehicle or carrier. For solutions or emulsions, suitable carriers include, for example, aqueous or alcoholic/aqueous solutions, emulsions or suspensions, including saline and buffered media.

The precise dose to be employed in the formulation of an anti-infective or therapeutic agent for therapeutic use will depend on the route of administration, and the seriousness of the disease or disorder, and should be decided according to the judgment of a practitioner and each patient's circumstances. Effective doses may be extrapolated from dose-response curves derived from in vitro or animal model test systems.

Parenteral vehicles can include sodium chloride solution, Ringer's dextrose, dextrose and sodium chloride, lactated Ringer's or fixed oils, for instance. Intravenous vehicles can include various additives, preservatives, or fluid, nutrient or electrolyte replenishers and the like (See, generally, Remington's Pharmaceutical Sciences, 17th Edition, Mack Publishing Co., Pa., 1985). For inhalation, the agent can be solubilized and loaded into a suitable dispenser for administration (e.g., an atomizer, nebulizer or pressurized aerosol dispenser).

Furthermore, where the anti-infective agent is a protein or peptide, the agent can be administered via in vivo expression of the recombinant protein. In vivo expression can be accomplished via somatic cell expression according to suitable methods (see, e.g. U.S. Pat. No. 5,399,346; the teachings of which are incorporated herein by reference). In this embodiment, nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

Pharmaceutical Compositions

The present invention also pertains to pharmaceutical compositions comprising inhibitors of complex formation between a Z-DNA binding ligand or variant thereof and Z-DNA, identified as described herein. The inhibitor can be formulated with a physiologically or pharmaceutically acceptable carrier or excipient to prepare a pharmaceutical composition. The carrier and composition can be sterile. The formulation should suit the mode of administration.

Suitable physiologically and pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The pharmaceutical composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intraocular, intravenous, subcutaneous, topical, oral and intranasal. Other suitable methods of introduction can also include gene therapy, rechargeable or biodegradable devices, particle acceleration devises ("gene guns") and slow release polymeric devices. The pharmaceutical compositions of this invention can also be administered as part of a combinatorial therapy with other compounds.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active compound. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., that are, if desired, sterilized or mixed with auxiliary agents, e.g., preservatives, stabilizers, wetting agents, buffers or salts for influencing osmotic pressure, etc. The compound may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Agents or therapeutics described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, that notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the compounds can be separated, mixed together in any combination, present in a single vial or tablet. Compositions assembled in a blister pack or other dispensing means is preferred. For the purpose of this invention, unit dosage is intended to mean a dosage that is dependent on the individual pharmacodynamics of each compound and administered in FDA approved dosages in standard time courses.

Kits

The invention also features a kit for detecting and/or identifying an anti-infective agent comprising a Z-DNA binding ligand or variant thereof, a nucleic acid, and a Z-DNA formation buffer, which may be in solution or lyophillized form. The Z-DNA formation buffer may comprise any reagents which form a solution that promote formation and or stabilization of Z-DNA contained in the solution. Examples of Z-DNA formation buffer are known in the art, and include, for example, solutions that cause and/or maintain negative supercoiling of DNA, for example, 75 mM KCl, 3 mM DTT, 5% glycerol, 200 $\mu$g/ml $E.\ coli$ tRNA, 10 mM $MgCl_2$, and 10 mM Tris-Cl (pH 8.0).

The present invention also features a method of increasing the pathogenicity of an infective agent, comprising introducing into the agent a gene encoding a Z-DNA binding protein or Z-DNA binding variant thereof. In addition, the present invention features a method of increasing the pathogenicity of an infective agent which comprises a gene encoding a Z-DNA binding protein, the method comprising producing a derivative of the infective agent comprising an altered version of said gene which encodes a protein having enhanced Z-DNA activity binding relative to that of the Z-DNA binding protein. Such methods are useful for screening for therapeutic compounds that can be used to inhibit the pathogenicity of an infectious agent and/or compounds that can inhibit binding of a Z-DNA binding ligand to Z-DNA. If may be preferable to use such these method to generate infective agent with increased pathogenicity as opposed to using more dangerous viruses, for example, pox viruses.

While this invention has been particularly shown and described with references to preferred embodiments thereof, it will be understood by those skilled in the art that various changes in form and details may be made therein without departing from the scope of the invention encompassed by the appended claims.

Exemplification

The present invention will now be illustrated by the following Examples, which are not intended to be limiting in any way.

EXAMPLE 1

Z$\alpha$ can Substitute for the Function of the N-terminal Domain of the Vaccinia Virus E3L The pathogenicity of viruses stems from the fact that they block programmed cell death (apoptosis) of the host cell. The basis for this derives from experiments with vaccinia virus that is lethal to mice. The vaccinia virus genome encodes an E3L protein, which is essential for pathogenicity. The E3L protein contains two domains; one domain binds to double-stranded RNA without regard to sequence, and the other domain (amino-terminal domain) has similarities to the sequence of a protein domain Zα. Zα is a protein domain from the amino-terminal region of human double stranded RNA adenosine deaminase (hADAR1), which has been shown to bind specifically and selectively to left-handed Z-DNA. The three-dimensional crystal structure of Zα complexed to Z-DNA has been determined (Schwartz et al., Science, 284:1841–1845, 1999), and from this structure, residues that interact with Z-DNA have been identified.

E3L is similar in amino acid sequence to Zα of hADAR1. In this study, experiments were performed to determine if the pathogenicity of E3L was related to Z-DNA binding.

To determine whether the N-terminal domain of the vaccinia virus E3L has a function similar to that of Zα, the following Z-DNA binding domain-swapping study was carried out. The amino-terminal domain of the vaccinia E3L protein (GenBank Accession Number: S64006) containing 67 amino acids was removed, and substituted with the Zα domain (Z-DNA binding domain) from hADAR1 (residues 129 through 196 of hADAR1 of GenBank Accession Number: U18121). A vaccinia virus that contained a gene encoding this chimeric E3L protein with a Zα amino-terminal domain (from hADAR1) was made. Previously, it had been shown that both the amino-terminal domain and the carboxy-terminal double-stranded RNA binding domains of E3L were essential for pathogenicity. When the vaccinia virus encoding the chimeric E3L protein was used to infect mice, the virus was 100% lethal. This lethality occurred even though only 15 of the 67 amino acids in the chimeric E3L molecule were unchanged relative to the amino-terminal domain of the E3L protein (the other 52 amino acids of E3L were changed by the domain swap). These results indicated that only a small number of specific amino acid residues were required for the pathogenic activity of E3L.

Most of the 15 amino acids that were constant between the E3L amino-terminal domains of E3L and the Zα domain of hADAR1 are used in the specific interaction between Zα and left-handed Z-DNA (Schwartz et al., Science, supra). For example, amino acids lysine at position 169, lysine at position 170, asparagine at position 173, arginine at position 174, tyrosine at position 177, threonine at position 191, proline at position 192, proline at position 193, and tryptophan at position 195 of the Zα domain of hADAR1 have been shown to contact Z-DNA.

EXAMPLE 2

Identification of E3L Residues Responsible for Vaccinia Virus Pathogenicity

Materials and Methods

Primer Design and Construction of Vectors

Construction of pMPADARZα-E3L and pMPADARZβ-E3L

Nucleotides (nt) 61–261 of the vaccinia virus (VV) E3L gene (coding for amino acids 1–67) were replaced by either nucleotides 554–742 (Zα) or nucleotides 1025–1216 (Zβ) of the human ADAR gene, in pMPE3L (Kibler et al., J. Virol., 71:1992–2003, 1997). This was done using a two-step PCR based mutagenesis protocol. The first PCR reaction involved the construction of mega primers, which were subsequently used in a second PCR reaction to generate the recombinant plasmids.

For synthesis of the mega primers the following oligonucleotides, based on human ADAR (GenBank Accession Number U10439) or VV E3L (GenBank Accession Number S64006) cDNA sequences, were used for PCR amplification. Underlined regions denote sequences from VV E3L fused to sequences from human ADAR to generate ADAR Zα or Zβ-E3L mega primers.

Primers for ADARZa-E3L Mega Primer Synthesis:
5'-AAAATGTCTATCTACCAAGATCAGGAACAAAGG-3' (SEQ ID NO: 16)(GenBank Accession Number U10439, nt 554–580); and 5α-CCGGCTTATCCGCCTCCGTTGT-CATTTTCCACAAAGGGGGTGTTCCTGCCT CTTTC-3' (SEQ ID NO: 17)(GenBank Accession Number S64006, nt 262–286 (underlined); GenBank Accession Number U10439, nt 711–742).

Primers for ADARZp-E3L Mega Primer Synthesis:
5'-AAAATGTTGGAGTTTTTAGACATGGCCGAG-3' (SEQ ID NO: 18)(GenBank Accession Number U10439, nt 1025–1048); and 5'-<u>CCGGCTTATCCGCCTCCGTTGTCAT</u>ATGCCAT ATGGGAGGGGTTGTCCCTT G-3' (SEQ ID NO: 19) (GenBank Accession Number S64006, nt 262–286 (underlined); GenBank Accession Number U10439, nt 1190–1216).

PCR was performed to synthesize the mega primers from pGEXADAR using Taq polymerase enzyme (Promega, Madison, Wis.) according to the manufacturer's instructions. PCR amplifications were performed as follows: (94° C. for 1 minute), followed by 25 cycles of amplification (94° C. for 1 minute, 50° C. for 2 minutes, 72° C. for 3 minutes). Mega primers were purified using QIAquick PCR purification kit (Qiagen, Valencia, Calif.) according to the manufacturer's instructions.

Whole plasmid PCR based mutagenesis (Fisher and Pei, Biotechniques, 23:570–574, 1997) was used in the construction of recombinant plasmids pMPADARZa-E3L and pMPADARZβ-E3L. This technique was a modification of the original technique. Briefly, divergent primers were designed flanking the region to be mutated. One of the primers annealed to the template pMPE3L in the flanking region immediately upstream of the E3L gene. The second primer was the mega primer, which contained at its 5' end, either Zα (nt 554–742) or Zβ (nt 1025–1216) sequences from ADAR fused to sequences from E3L (nt 262–286). Both the primers were phosphorylated at their 5' ends using T4 polynucleotide kinase (Gibco BRL, Rockville, Md.) according to the manufacturer's instructions.

PCR was performed using 10–50 ng of pMPE3L template, 50 pmols of phosphorylated primers, 2.5 mM dNTPs, and PFU polymerase (Stratagene, LaJolla, Calif.). The following parameters were used for PCR amplifications: 94° C. for 4 minutes, followed by 16 cycles of (94° C. for 1 minute, 50 for 2 minutes, 72° C. for 15 minutes). The PCR products were purified using QIAquick PCR purification kit (Qiagen, Valencia, Calif.) according to the manufacturer's instructions.

Linear PCR products were ligated using T4 DNA Ligase (Gibco BRL, Rockville, Md.) according to the manufacturer's instruction. Following ligation, the template DNA was digested using DPNI restriction enzyme (Stratagene, La Jolla, Calif.) according to the manufacturer's instruction. The product was transformed into DH5α bacterial cells. Bacterial colonies that contained either the pMPADARZα-E3L or pMPADARβ-E3L were screened by PCR. The plasmids were sequenced to confirm the presence of the ADARZα-E3L or ADARZβ-E3L gene.

Construction of pMPDLM-1Zα-E3L

Nucleotides 61–261 of VV E3L gene (coding for amino acids 1–67) were replaced by nucleotides 116–316 (Zα) of the murine DLM-1 gene, in pMPE3L. This was done using a two-step protocol. In the first step, PCR was performed to amplify the $Z\alpha_{ADAR1}$ sequence with sites BamHI and AatII attached at its 5' and 3' ends respectively. In the second step, $Z\alpha_{DLM1}$ was cloned into pMPE3L by BamHI and AatII digestion of both $Z\alpha_{DLM1}$, and pMPE3L.

In order to amplify the $Z\alpha_{DLM1}$ sequence, the following oligonucleotides, based on murine DLM-1 (AF136520), or VV E3L (S64006) cDNA sequences or on the vector pMPE3LΔGPT (Kibler et al., supra), were used for PCR amplification. Underlined regions denote sequences from VV E3L (downstream primer) or pMPE3LΔGPT (upstream primer) fused to sequences from mouse DLM-1 gene, to generate DLM-1Zα.

Upstream Primer
5'-TCTAAAAAGGATCCCCCGGGCTGCCTGAAAA TGGCAGAAGCTCCTGTTGA C-3' (SEQ ID NO: 20) (pMPE3LΔGPT, nt 2207–2181 (numbering is as in the parental plasmid, pBluescript) (underlined); GenBank Accession Number AF136520, nt 116–136).

Downstream Primer
5'ATCTATTATGACGTCAGCCATAGCATCAGCATCC GGCTTATCCGCCTCCGTTGTCATGCTCCATGTT GCAGGCTCTG-3' (SEQ ID NO: 21)(GenBank Accession Number S64006, nt 1920–1976 (underlined); GenBank Accession Number AF136520, nt (297–316)).

PCR was performed to amplify $Z\alpha_{DLM1}$ from the DLM1 cDNA in pGEM-T (Fu et al. Gene, 240:157–163, 1999) using Platinum Pfx (Gibco BRL, Rockville, Md.) according to the manufacturer's instructions. PCR amplifications were performed as follows: (95° C. for 1 minute), followed by 35 cycles of amplification (95° C. for 1 minute, 50° C. for 1 minutes, 68° C. for 1 minute).

The PCR product and vector pMPE3LΔGPT were digested with BamHI, followed by purification using Micropure-EZ (Millipore, Bedford, Mass.) and Microcon (Millipore, Bedford, Mass.). The purified products were digested with AatII, followed by gel extraction (QIAEX II, Qiagen, Valencia, Calif.). The digested insert and vector were ligated using T4 DNA Ligase (Promega, Madison, Wis.) according to the manufacturer's instruction. Following ligation, the products were transformed into TOP10 E. coli (Invitrogen, Carlsbad, Calif.). Plasmid DNA was extracted and sequenced to screen for, and confirm the presence of pMPDLM-1Zα-E3L.

Generation of Point Mutations in pMPADARZα-E3L, pMPADARZβ-E3L and pMPE3L

Whole plasmid PCR based mutagenesis using overlapping primers (Makarova et al., Biotechniques, 29:970–972, 2000) was used to generate mutations in pMPADARZα-E3L, pMPADARZβ-E3L, and pMPE3L. Briefly, overlapping primers 40–45 bases in length were designed with 8–10 base overhang on their 5' ends. The codon of interest was mutated on both primers in the region of overlap, roughly in the middle of the primers.

PCR was performed using 100–300 ng template, 200 nM of each primer, 800 μM dNTPs and 1.25 units PFU polymerase (Stratagene, LaJolla, Calif.). The following parameters were used for PCR amplifications: 95° C. for 3 minutes, followed by 18 cycles of (95° C. for 15 seconds, 50° C. for 1 minute, 68° C. for 12 minutes). Controls without either the primers or polymerase were run to determine background levels of template.

Template DNA was digested using DPNI restriction enzyme (Stratagene, La Jolla, Calif.) according to the manufacturer's instruction. The product was transformed into DH5α bacterial cells. Plasmid DNA was extracted and sequenced to screen for, and confirm the presence of, point mutations in pMPADARZα-E3L and pMPADARZβ-E3L.

Cell Culture

BHK21 cells were cultured in MEM (Gibco BRL, Rockville, Md.) containing 10% fetal bovine serum (FBS), 50 μg/mL gentamycin, and 0.1 mM non-essential amino acid solution (MEM 5%, Gibco BRL, Rockville, Md.). Cells were incubated at 37° C. with 5% $CO_2$. RK13 cells were cultured in MEM (Gibco BRL, Rockville, Md.) containing 5% FBS, 50 μg/mL gentamycin, and 0.1 mM non-essential amino acid solution (MEM 5%, Gibco BRL, Rockville, Md.). Cells were incubated at 37° C. with 5% $CO_2$.

In Vivo Recombination

The WR strain of VV deleted of the E3L gene (VVΔE3L) was used as the parent virus for recombination. In VVΔE3L, the E3L gene has been replaced with the LacZ gene. In vivo recombination was performed as described previously (Kibler et al, supra), except that BHK cells were used instead of RK-13 cells, and cells were infected at a multiplicity of infection (MOI) of 0.05, instead of 10 p.f.u./cell. All viruses, except for $Z\alpha_{DLM1}$-E3L and all mutations in E3L, were obtained by transient dominant selection as previously described (Kibler et al., supra). For $Z\alpha_{DLM1}$-E3L, and all mutations in E3L recombinant viruses were obtained after selection for interferon resistance in RK-13 cells. Briefly, confluent monolayers of RK-13 cells were treated with 1000 U/ml of recombinant huIFNαA/D and infected with virus obtained from a standard infection/transfection reaction. Plaques that formed in interferon-treated cells will have taken up a functional E3L gene from the transfected plasmid. After multiple rounds of plaque purification, the plaques were amplified to make virus stocks.

Virus Amplification

BHK21 cells were used to amplify the recombinant virus. Cell culture media was removed from the monolayers and virus infections were performed in MEM (Gibco BRL, Rockville, Md.) containing 2% FBS, 50 μg/mL gentamycin, and 0.1 mM non-essential amino acid solution (MEM 5%, Gibco BRL, Rockville, Md.). Cells were infected with the virus in 200 μL volume, incubated at 37° C., 5% $CO_2$ for 1 hour, with rocking every 10 minutes. Following infection, the cell culture medium was replaced. At 100% cytopathicity, infected BHK21 cells were harvested and subjected to 3 rounds of freezing (−80° C.) and thawing (37° C.), followed by 30 second sonication to release the virus. Cell debris was pelletted by centrifugation at 700×g for 10 min at 4° C. The supernatant was transferred into a fresh tube and stored at −80° C. The virus in the supernatant was titered in RK13 cells.

Results

Figure 2A:
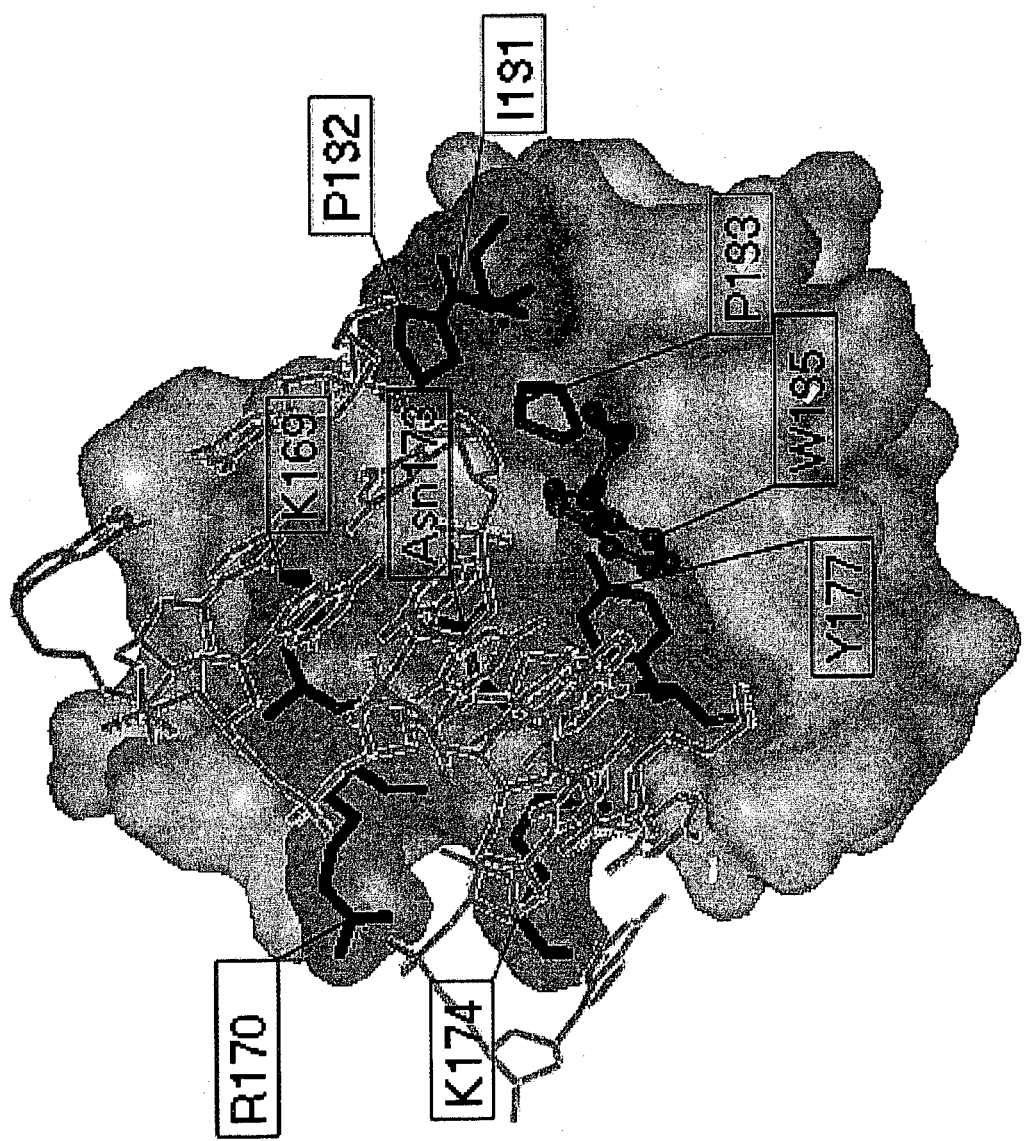
FIG. 2A is a schematic representation of a surface view of Variola E3L (dark gray) in contact with Z-DNA (light gray), with side chains of E3L represented in stick format (black), and Trp195 (which contacts Z-DNA indirectly) shown in ball and stick format.
Figure 2B:
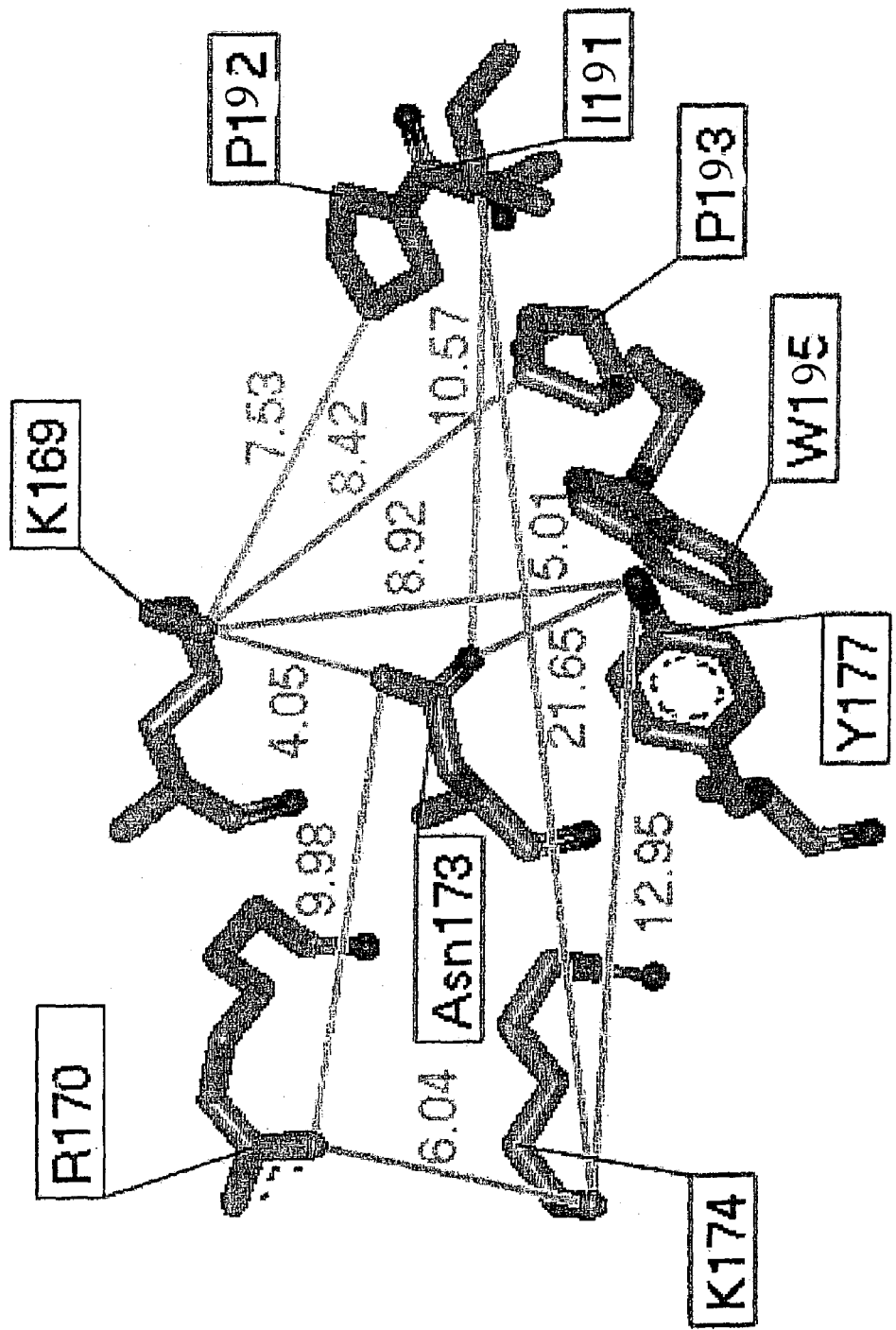
FIG. 2B is a schematic illustration of Variola or Vaccinia E3L showing residues in contact with Z-DNA, with side chains of E3L represented in stick format, and the distances between contacting residues (in Angstroms) shown, with emphasis on charged groups.

Based on the results of the above-described domain-swapping studies, experiments were carried out to determine if the amino acid residues of E3L, predicted to contact Z-DNA, based on conservation of amino acid residues between the two proteins were involved in viral pathogenicity. FIGS. 2A and 2B show the variola E3L residues (using the hADAR1 amino acid numbering system) predicted to bind to Z-DNA, based on structural studies of the homologous domain Zα of hADAR1, as described herein. For example, amino acids lysine at hADAR1 position 169 (corresponding to asparagine at position 40 of E3L), arginine at hADAR1 position 170 (corresponding to asparagine at position 41 of E3L), asparagine at hADAR1 position 173 (corresponding to asparagine at position 44 of E3L), lysine at hADAR1 position 174 (corresponding to asparagine at position 45 of E3L), tyrosine at hADAR1 position 177 (corresponding to asparagine at position 48 of E3L), isoleucine at hADAR1 position 191 (corresponding to asparagine at position 62 of E3L), proline at hADAR1 position 192 (corresponding to asparagine at position 63 of E3L), proline at hADAR1 position 193 (corresponding to asparagine at position 64 of E3L), and tryptophan at hADAR1 position 195 (corresponding to asparagine at position 66 of E3L) are predicted to be in contact with Z-DNA and mediate viral pathogenicity.

In addition, these results also indicate that a Z-DNA binding motif of K[K/R]XXN[R/K]XXY[X]$_{13}$[T/I]PPXW (SEQ ID NO:5), where X (Xaa) is any amino acid, is important for mediating viral pathogenicity. Polypeptides that are at least about 50%, 60%, 70%, 80%, 85%, 90%, or 95% identical to the amino sequence K[K/R]XXN[R/K]XXY[X]$_{13}$[T/I]PPXW (SEQ ID NO:5), where X (Xaa) is any amino acid, or polypeptides containing a sequence that is at least about 50%, 60%, 70%, 80%, 85%, 90%, or 95% identical to the amino sequence K[K/R]XXN[R/K]XXY[X]$_{13}$[T/I]PPXW (SEQ ID NO:5), where X (Xaa) is any amino acid, can be made and evaluated for inhibition of the formation of a complex between Z-DNA and a Z-DNA binding ligand or variant using the methods described herein.

To further investigate whether binding of E3L to Z-DNA mediates viral pathogenicity, experiments were carried out in which residues of vaccinia virus E3L predicted to bind to Z-DNA (as described above) were mutated. Mutating the Z-DNA binding residues of the Zα domain was known to diminish or abolish Z-DNA binding of hADAR1. Specifically, the following amino acids of the vaccinia E3L were mutated: asparagine at position 44 (corresponding to position 173 of Zα) was mutated to alanine, and tryptophan at position 66 (corresponding to position 195 of Zα) was mutated to leucine, and mutant viruses were prepared, as described by Brandt and Jacobs (J. Virol. 75:850–856, 2001; the teachings of which are incorporated by reference). In addition, a double mutant in which both asparagine at position 44 and tryptophan at position 66 were mutated was made. Each of these mutations in E3L resulted in a loss of pathogenicity when the vaccinia virus was administered to mice, compared to unmutated virus. The single mutations were just as effective at reducing pathogenicity as the double mutation. These results indicate that a crucial portion of the pathogenicity of vaccinia virus is related to the interaction of the amino-terminal Z-DNA binding domain to left-handed Z-DNA.

Figures 3A, 3B:
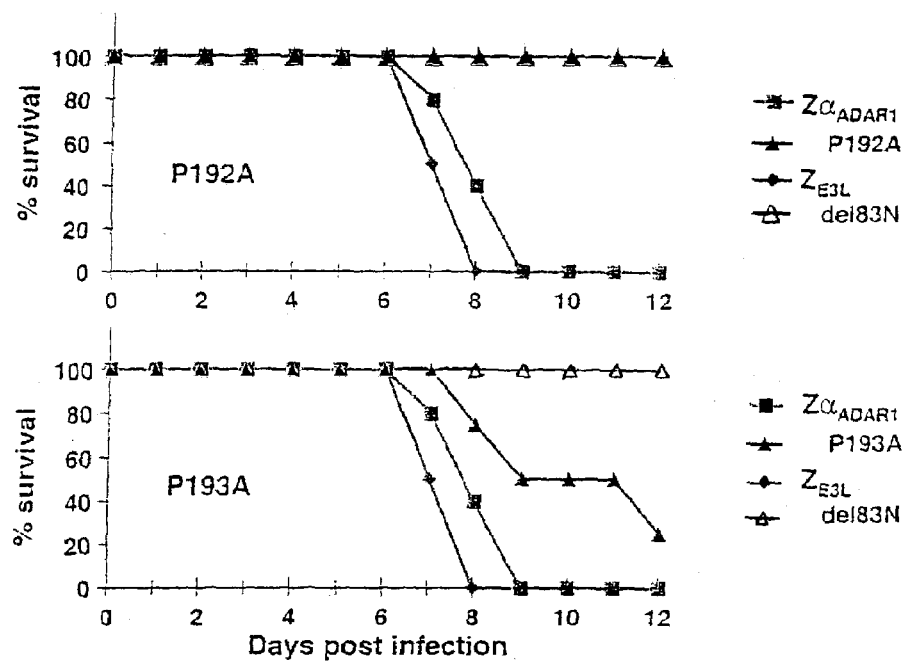
FIG. 3A is a graph of the lethality of vaccinia virus or variants in mice (percent survival) inoculated with wild type vaccinia virus ($Z_{E3L}$); vaccinia virus in which the 83 amino-terminal amino acids of the E3L protein have been deleted (del83N); vaccinia virus in which the Z-DNA binding domain $Z\alpha_{ADAR1}$ has been substituted for the N-terminal domain of E3L ($Z\alpha_{ADAR1}$); or vaccinia virus in which proline at amino acid position 192 in the $Z\alpha_{ADAR1}$ construct has been mutated to alanine (P192A); over time (days post infection).
FIG. 3B is a graph of the lethality of vaccinia virus or variants in mice (percent survival) inoculated with wild type vaccinia virus ($Z_{E3L}$); vaccinia virus in which the 83 amino-terminal amino acids of the E3L protein have been deleted (del83N); vaccinia virus in which the Z-DNA binding domain $Z\alpha_{ADAR1}$ has been substituted for the N-terminal domain of E3L ($Z\alpha_{ADAR1}$); or vaccinia virus in which proline at amino acid position 193 in the $Z\alpha_{ADAR1}$ construct has been mutated to alanine (P193A); over time (days post infection).

In a second domain swap study, 48 amino acids in the N-terminal domain of E3L of were changed while 15 amino acids were preserved. Upon infection with 100 plaque forming units (p.f.u.) (via intracranial innoculation) the virus with the chimeric E3L molecule was 100% pathogenic, as shown in FIGS. 3A and 3B (Zα$_{ADAR1}$), which are graphs of the lethality in mice (percent survival) inoculated with wild type vaccinia virus (Z$_{E3L}$); vaccinia virus in which the 83 amino-terminal amino acids of the E3L protein have been deleted (del83N); vaccinia virus in which the Z-DNA binding domain ZαADAR1 has been substituted for the N-terminal domain of E3L (Zα$_{ADAR1}$); or vaccinia virus in which proline at amino acid position 192 in the Zα$_{ADAR1}$ construct has been mutated to alanine (P192A) (FIG. 3A) or vaccinia virus in which proline at amino acid position 193 in the Zα$_{ADAR1}$ construct has been mutated to alanine (P193A) (FIG. 3B); over time (days post infection).

When mutations were made in some of the residues that were essential for Z-DNA binding, they either reduced or abolished pathogenicity of the virus. In previous experiments with ADAR1, it was shown that mutating proline 192 to alanine abolished Z-DNA binding as shown in a Southwestern assay (Schade et al., EMBO J., 18:470–479, 1999), and that mutating proline 193 to alanine resulted in weaker Z-DNA binding. Intracerebral inoculation with 100 plaque-forming units of wild type E3L virus led to the death of all mice in eight days (FIGS. 3A and 3B, Z$_{E3L}$). Similar results were seen when mice were inoculated with chimeric virus in which Zα of ADAR1 replaced the N-terminal domain of E3L, with all mice dead in nine days (FIGS. 3A and 3B, Zα$_{ADAR1}$). Inoculation of mice with a vaccinia virus in which the N-terminus of E3L was deleted up to position 83 (del83N) resulted in no lethality. Inoculation of mice with the Zα$_{ADAR1}$ chimeric virus in which proline at residue 192 was mutated to alanine construct likewise abolished all lethality (FIG. 3A, P192A). On the other hand inoculation of mice with Zα$_{ADAR1}$ in which proline at residue 193 was mutated to alanine led to decreased lethality (FIG. 3B, P193A). These results suggest that reduced Z-DNA binding gives rise to reduced lethality, and loss of Z-DNA binding gives rise to loss of lethality.

It has been shown that when a physiological solution of poly(dG-dC) or d(CG)$_6$ is assayed using a circular dichroism machine, it exists entirely as right-handed B-DNA. However, if the Zα of ADAR1 is titered into the solution, the DNA rapidly converts to Z-DNA with the protein bound to it (Herbert et al., Proc. Natl. Acad. Sci. USA, 94:8421–8426, 1997). The conversion is complete at a ratio of approximately one Zα$_{ADAR1}$ residue per four base pairs (Berger et al., Biochemistry, 37:13313–13321, 1998). Thus, the change in circular dichroism is a measure of the binding of Zα to Z-DNA.

Figures 4A, 4B:
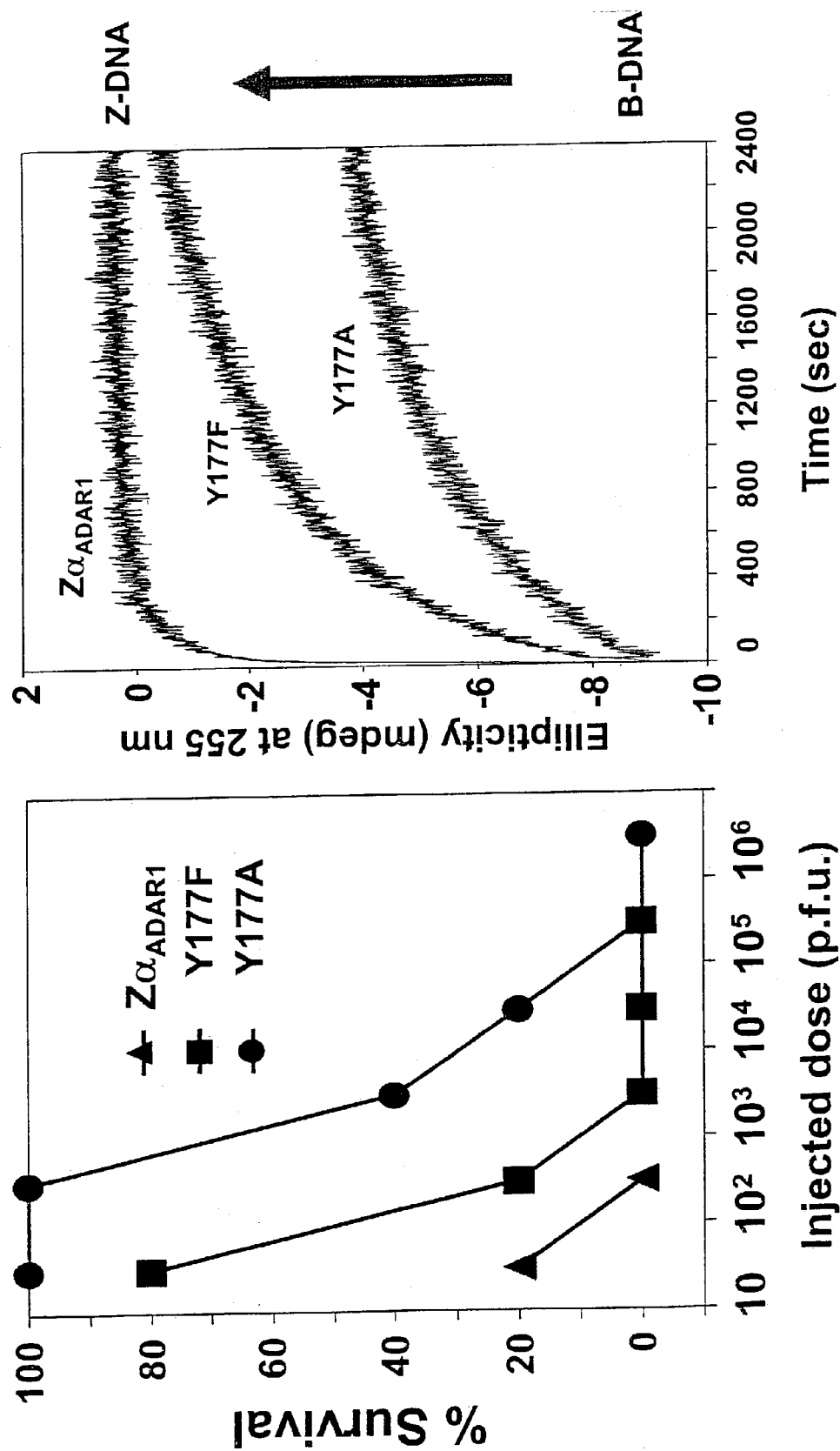
FIG. 4A is a graph of the lethality of vaccinia virus or variants in mice (percent survival) inoculated with vaccinia virus in which the Z-DNA binding domain $Z\alpha_{ADAR1}$ has been substituted for the N-terminal domain of E3L ($Z\alpha_{ADAR1}$); vaccinia virus in which tyrosine at amino acid position 177 in the $Z\alpha_{ADAR1}$ construct has been mutated to phenylalanine (Y177F); or vaccinia virus in which tyrosine at amino acid position 177 in the $Z\alpha_{ADAR1}$ construct has been mutated to alanine (Y177A); over time (days post infection). Mice were infected with vaccinia viruses containing $Z\alpha_{ADAR1}$-E3L chimeric genes, including the indicated mutations, via intra-cranial injection with the indicated number of plaque-forming units (p.f.u.) of vaccinia virus constructs in 10 µl. The mice were monitored for mortality for two weeks.
FIG. 4B is a graph of the binding activity, which is measured by the conversion of $d(CG)_6$ DNA from a B conformation to a Z conformation (Ellipticity (mdeg) at 255 nm) by $Z\alpha_{ADAR1}$ protein; $Z\alpha_{ADAR1}$ protein in which tyrosine at amino acid position 177 has been mutated to phenylalanine (Y177F); or $Z\alpha_{ADAR1}$ protein in which tyrosine at amino acid position 177 has been mutated to alanine (Y177A) over time (seconds) as assessed by circular dichroism. Conversion of DNA from the B conformation to the Z conformation occurs as the ellipticity becomes less negative and indicates binding of the protein to the Z-DNA. The ellipticity at 255 nanometers is monitored as a function of time, using 90 µM (base pair) of $d(CG)_6$ and 30 µM of protein.

Dose-response experiments with tyrosine ADAR1 177 (chimeric E3L protein in which Zα$_{ADAR1}$ is swapped for the amino-terminus of E3L, and in which a tyrosine residue is located at position 177 of the Zα$_{ADAR1}$ protein for mouse pathogenicity studies, and Zα$_{ADAR1}$ protein in which a tyrosine residue is located at position 177 for in vitro Z-DNA binding studies) and its mutants illustrate the correlation of Z-DNA binding with pathogenicity. In Zα$_{ADAR1}$, tyrosine 177 is involved in stabilizing a Van der Waals contact with the syn guanine of Z-DNA and also, through its hydroxyl group, stabilizes Z-DNA by binding to the phosphate group. Circular dichroism experiments are shown in FIG. 4B, which is a graph of the effects of adding Zα$_{ADAR1}$, tyrosine 177 proteins and mutants thereof (Y177F and Y177A) to an oligonucleotide with alternating CG base pairs. The rapid and complete conversion to Z-DNA was seen when the wild type Zα of ADAR1 (Zα$_{ADAR1}$) was added to d(CG)$_6$. However, the mutant of tyrosine 177 changed to phenylalanine (Y177F) produced a slower and less complete circular dichroism spectral change, and the change to alanine (Y177A) produced much less Z-DNA binding.

The dissociation constant ($K_d$) of the interaction of all 3 of the above constructs with Z-DNA was also measured using surface plasmon resonance (Herbert, 1997, supra). For this measurement, poly(dG-dC) was partially brominated to stabilize it in the Z-DNA conformation. The $K_d$ of Zα$_{ADAR1}$ protein for Z-DNA was determined to be 40 nM. The phenylated mutant of tyrosine 177 (Y177F) reduced the $K_d$ to 350 nM, and the alanine mutant of tyrosine (Y177A) reduced the $K_d$ further to 700 nM. It should be noted that circular dichroism assays and $K_d$ measurements measure different things; $K_d$ measurements reflect the affinity of the Z-DNA binding protein for pre-formed Z-DNA, while the circular dichroism assay measurements involve a conversion of right-handed B-DNA into left-handed Z-DNA followed by binding. Thus, these assay should not necessarily be compared to each other quantitatively.

These results were mirrored in the survival of mice following intra-cerebral injection of viruses made with these chimeric proteins, shown in FIG. 4A, which is a graph of the lethality in mice (percent survival) inoculated with wild type vaccinia virus (WT($Z_{E3L}$)); vaccinia virus in which the Z-DNA binding domain $Z\alpha_{ADAR1}$ has been substituted for the N-terminal domain of E3L ($Z\alpha_{ADAR1}$); vaccinia virus in which the Z-DNA binding domain $Z\alpha_{ADAR1}$ has been substituted for the N-terminal domain of E3L and in which tyrosine at amino acid position 177 in the $Z\alpha_{ADAR1}$ domain has been mutated to phenylalanine (Y177F); or vaccinia virus in which the Z-DNA binding domain $Z\alpha_{ADAR1}$ has been substituted for the N-terminal domain of E3L and in which tyrosine at amino acid position 177 in the $Z\alpha_{ADAR1}$ construct has been mutated to alanine (Y177A); over time (days post infection). At a dose of ten plaque-forming units (p.f.u.), the wild type E3L and the chimera in which Zα of ADAR1 was substituted for the amino-terminal of E3L yielded a survival of 20–40% by day 9. In mice inoculated with the mutant Y177F survival was 80%, while mice inoculated with the mutant Y177A had complete survival. Infection of mice with chimeras in which tyrosine 177 was mutated to phenylalanine (Y177F) killed 80% of the mice at a dose of $10^2$ p.f.u., indicating that this virus is approximately 10 times less pathogenic than unmutated virus containing $Z\alpha_{ADAR1}$. The mutant Y177A required much higher doses in order to produce complete lethality. As the injected dose was increased to $10^4$ p.f.u., survival of mice inoculated the mutant Y177A decreased to a level similar to that of the mice inoculated with wild type and the $Z\alpha_{ADAR1}$ chimera at $10^2$ plaque-forming units and above. Thus, the chimeric virus with a Y177A mutation is approximately 1000 times less pathogenic than virus containing unmutated $Z\alpha_{ADAR1}$ chimeric E3L. These studies show that there is a parallel between the amount of Z-DNA binding and the pathogenicity of wild type E3L virus and its chimeric viruses.

Figure 5B:
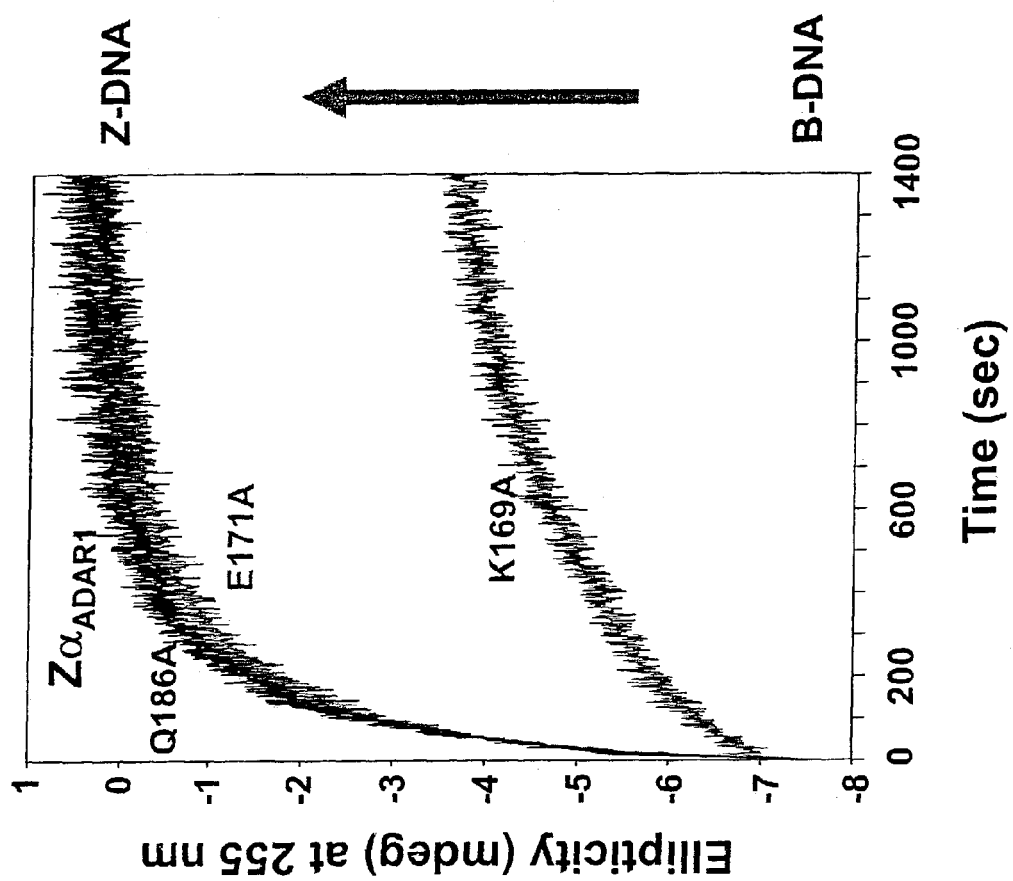
FIG. 5B is a graph of the binding activity, which is measured by the conversion of DNA from a B conformation to a Z conformation (Ellipticity (mdeg) at 255 nm) of $Z\alpha_{ADAR1}$, $Z\alpha_{ADAR1}$ in which glutamine at amino acid position 186 has been mutated to alanine (Q186A); $Z\alpha_{ADAR1}$ in which glutamic acid at amino acid position 171 has been mutated to alanine (E171A); or $Z\alpha_{ADAR1}$ in which lysine at amino acid position 169 has been mutated to alanine (K169A) over time (seconds) as assessed by circular dichroism. Conversion of DNA from the B conformation to the Z conformation occurs as the ellipticity becomes less negative, and indicates binding of the protein to the Z-DNA.

One consideration for viral pathogenicity may be the distinction between amino acid side chains that interact with Z-DNA and those that do not. The following studies were carried out to explore this distinction. In the structure of $Z\alpha_{ADAR1}$, lysine 169 (K169) forms a hydrogen bond with a phosphate group and, in addition, hydrogen bonds to a water molecule which bonds to the next phosphate group. Lysine 170 (K170) also interacts with Z-DNA, however, the next residue on the recognition helix, glutamic acid 171 (E171) does not interact with Z-DNA. In addition, glutamine 186 (N186) also does not interact with Z-DNA. Lysine 169, glutamic acid 171, and glutamine 186 of ZαADAR1 were each individually mutated to alanine and assessed for Z-DNA binding by measuring circular dichroism. FIG. 5B is a graph of the binding activity (measured by the conversion of DNA from a B conformation to a Z conformation) of $Z\alpha_{ADAR1}$ ($Z\alpha_{ADAR1}$); $Z\alpha_{ADAR1}$ in which glutamine at amino acid position 186 has been mutated to alanine (Q186A); $Z\alpha_{ADAR1}$ in which glutamic acid at amino acid position 171 has been mutated to alanine (E171A); $Z\alpha_{ADAR1}$ in which lysine at amino acid position 169 has been mutated to alanine (K169A); and E3L (WT ($ZE_3L$)) over time (seconds). The conversion of B-DNA to Z-DNA in the sample containing the K169A mutant was only partial and was slow, while the rates of conversion of both the E171A and Q186A mutant $Z\alpha_{ADAR1}$ proteins were comparable to the rate observed with the unmutated $Z\alpha_{ADAR1}$ protein.

Figure 5A:
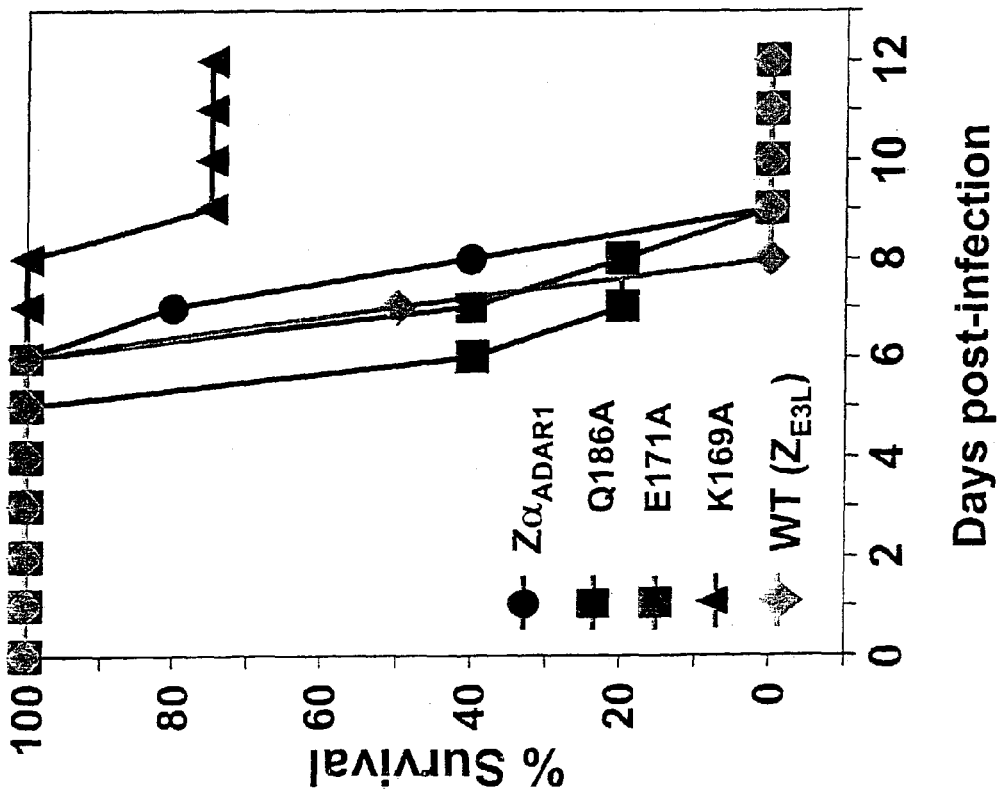
FIG. 5A is a graph of the lethality of vaccinia virus or variants in mice (percent survival) inoculated with wild type vaccinia virus ($WT(Z_{E3L})$); vaccinia virus in which the Z-DNA binding domain ZαADAR1 has been substituted for the N-terminal domain of E3L ($Z\alpha_{ADAR1}$); vaccinia virus in which glutamine at amino acid position 186 in the $Z\alpha_{ADAR1}$ construct has been mutated to alanine (Q186A); vaccinia virus in which glutamic acid at amino acid position 171 in the $Z\alpha_{ADAR1}$ construct has been mutated to alanine (E171A); or vaccinia virus in which lysine at amino acid position 169 in the $Z\alpha_{ADAR1}$ construct has been mutated to alanine (K169A) over time (days post infection). Mice were infected with the indicated virus via intra-cranial injection with the 100 plaque-forming units (p.f.u.) of vaccinia virus constructs in 10 µl. The mice were monitored for mortality for 12 days.

The effect of vaccinia virus containing these mutants on lethality in mice inoculated with the viruses was also examined. FIG. 5A is a graph of the lethality in mice (percent survival) inoculated with wild type vaccinia virus (WT ($Z_{E3L}$)); vaccinia virus in which the Z-DNA binding domain $Z\alpha_{ADAR1}$ was substituted for the N-terminal domain of E3L ($Z\alpha_{ADAR1}$); vaccinia virus in which the Z-DNA binding domain $Z\alpha_{ADAR1}$ was substituted for the N-terminal domain of E3L and in which glutamine at amino acid position 186 of the $Z\alpha_{ADAR1}$ construct was mutated to alanine (Q186A); vaccinia virus in which the Z-DNA binding domain $Z\alpha_{ADAR1}$ has been substituted for the N-terminal domain of E3L and in which glutamic acid at amino acid position 171 of the $Z\alpha_{ADAR1}$ construct has been mutated to alanine (E171A); or vaccinia virus in which the Z-DNA binding domain $Z\alpha_{ADAR1}$ has been substituted for the N-terminal domain of E3L and in which lysine at amino acid position 169 of the $Z\alpha_{ADAR1}$ construct has been mutated to alanine (K169A) over time (days post infection). As shown in FIG. 5A, there was a distinct loss of pathogenicity in mice inoculated with the virus containing the K169A mutant. After intracerebral inoculation of 100 p.f.u., 75% of the animals survived the length of the 12 day experiment. However, mice inoculated with the wild-type virus, the $Z\alpha_{ADAR1}$ chimeric virus, the Q186A mutant chimeric virus, and the E171A mutant chimeric virus were all dead by 8 or 9 days post inoculation.

A test was then carried out involving a residue that is near the Z-DNA binding site, but does not actually interact with Z-DNA. Thus, glutamine 186 in the $Z\alpha_{ADAR1}$ construct was mutated to alanine (Q186A). This glutamine is located on the β2 strand of the β sheet, so it is near the Z-DNA binding region but is not actually engaged. As shown in FIG. 5B, the Q186A mutation in ZαADAR1 rapidly converted B-DNA to Z-DNA. When this mutant was inoculated into mice in the form of a chimeric vaccinia virus, as shown in FIG. 5A, the mutant was as pathogenic as the wild-type (WT ($Z_{E3L}$) virus and the Zα ADAR ($Z\alpha_{ADAR1}$) substituted chimeric viruses, with all animals dead by 9 days. These experiments indicate that mutations that weaken Z-DNA binding also weaken pathogenicity, but those that do not influence Z-DNA binding do not influence pathogenicity.

Figure 6B:
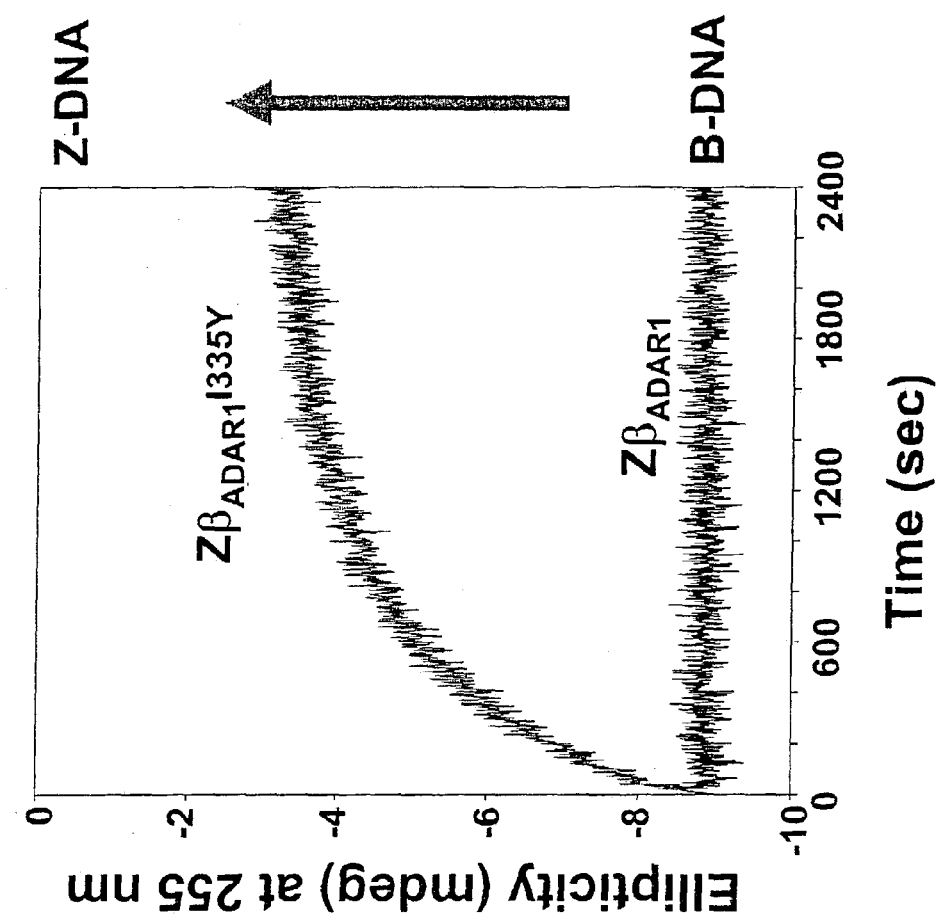
FIG. 6B is a graph of the binding activity, which is measured by the conversion of DNA from a B conformation to a Z conformation (Ellipticity (mdeg) at 255 nm) of vaccinia virus E3L in which the amino-terminal domain of E3L has been replaced with the Zβ domain of ADAR1 (ZβADAR1); or vaccinia virus E3L in which the amino-terminal domain of E3L has been replaced with the Zβ domain of ADAR1 and in which the isoleucine in a position that is analogous to position 177 in Zα has been changed to tyrosine ((Zβ$_{ADAR1}$I335Y)) over time (seconds) as assessed by circular dichroism. Conversion of DNA from the B conformation to the Z conformation occurs as the ellipticity becomes less negative, and indicates binding of the protein to the Z-DNA.
Figure 6A:
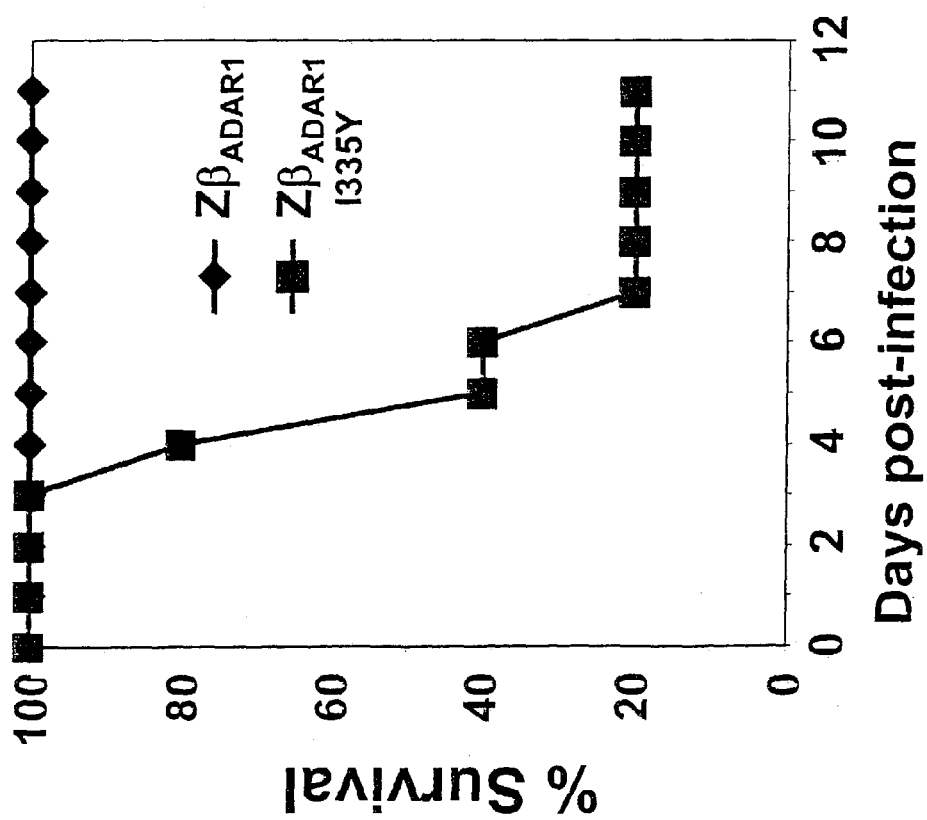
FIG. 6A is a graph of the lethality of vaccinia virus and variants in mice (percent survival) inoculated with vaccinia virus in which the amino-terminal domain of E3L has been replaced with the Zβ domain of ADAR1 (Zβ$_{ADAR1}$); or vaccinia virus in which the amino-terminal domain of E3L has been replaced with the Zβ domain of ADAR1 and in which the isoleucine in a position that is analogous to position 177 in Zα has been changed to tyrosine (Zβ$_{ADAR1}$I335Y) at various doses of viral inoculation (p.f.u.). Mice were infected intra-cranially with $10^6$ p.f.u. of either a ZβADAR1-E3L chimeric virus, or the chimeric virus with an I335Y mutation and survival was monitored over time.

Another type of experiment was undertaken in which a protein that does not bind Z-DNA was mutated so that it then could bind Z-DNA. The Zβ protein domain of ADAR1 has many sequence similarities to the Zα of ADAR1, but it does not bind to Z-DNA. This is shown in FIG. 6B where the circular dichroism of d(CG)$_6$ in the presence of Zβ remained constant over time. Zβ has an isoleucine residue, instead of a tyrosine residue, at the position analogous to Y177 in Zα (Zβ$_{ADAR1}$I335). When a mutant Zβ polypeptide was made in which the isoleucine was changed to tyrosine (Zβ$_{ADAR1}$I335Y), it then bonded to Z-DNA as assayed by a circular dichroism assay in which d(CG)$_6$ partially changed to the Z conformation in the presence of Zβ$_{ADAR1}$I335Y (FIG. 6B). Associated with this, at $10^6$ plaque-forming units, a modified E3L chimeric virus in which the N-terminus of the E3L protein was substituted with Zβ$_{ADAR1}$I335Y was 80% lethal, while a modified E3L chimeric virus in which the N-terminus of the E3L protein was substituted with Zβ$_{ADAR1}$I335 was non-lethal (FIG. 6A). In these studies, conversion of a non-Z-DNA binding protein to a weak Z-DNA binding protein was associated with the onset of lethality.

Figure 7:
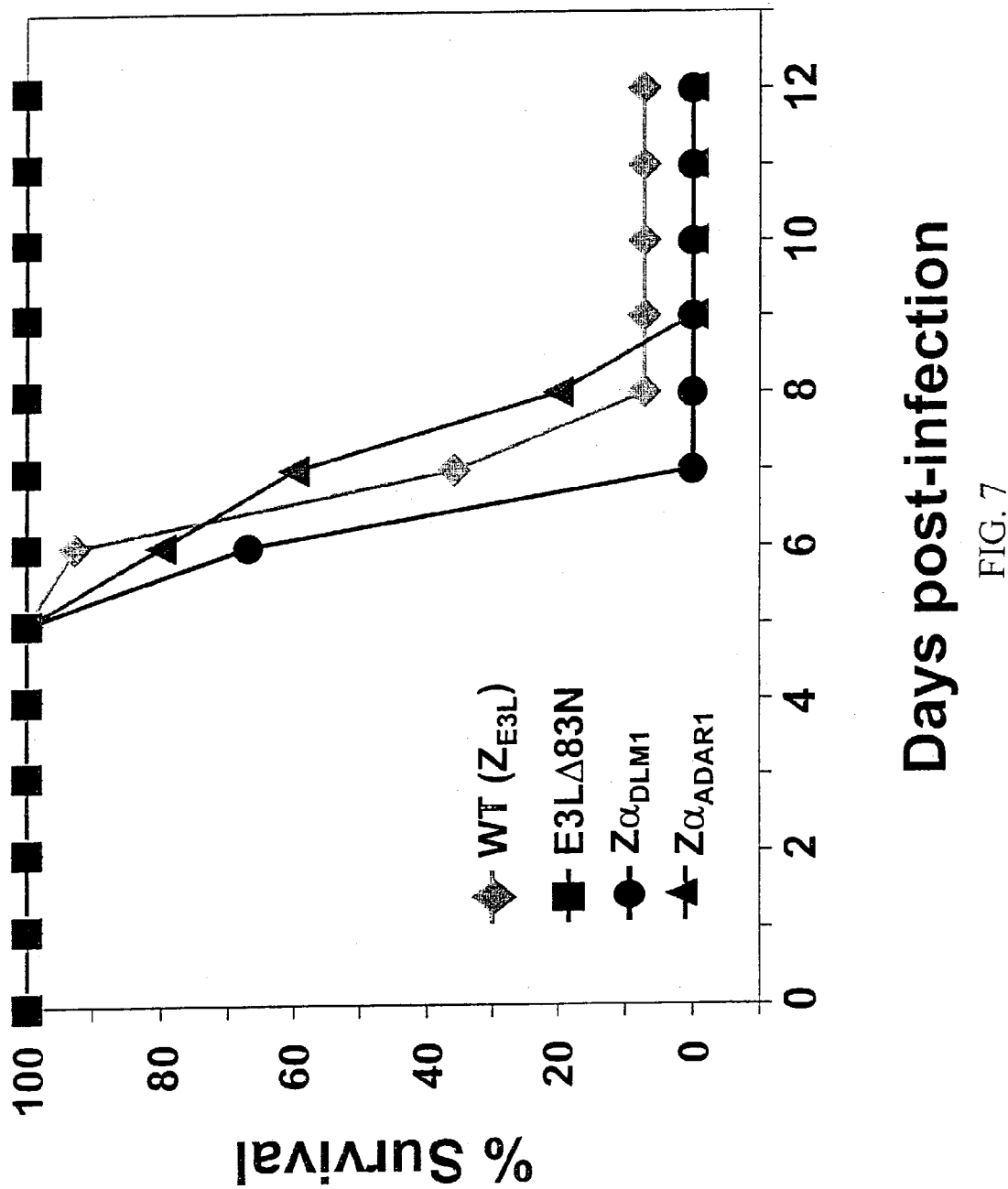
FIG. 7 is a graph of the lethality of vaccinia virus or variants in mice (percent survival) inoculated with wild type vaccinia virus (WT(Z$_{E3L}$))); vaccinia virus in which the 83 amino-terminal amino acids of the E3L protein have been deleted (E3LΔ 83N); vaccinia virus in which the human Z-DNA binding domain Zα$_{ADAR}$ has been substituted for the N-terminal domain of E3L (Zα$_{ADAR1}$); or vaccinia virus in which the murine Z-DNA binding domain of the DLM protein has been substituted for the N-terminal domain of E3L (Zα$_{DLM1}$) over time (days post infection). Groups of 4 to 6 C57BL/6 mice (4–6 weeks old) were infected intra-cranially with the indicated number of plaque-forming units (p.f.u.) of vaccinia virus constructs in 10 µl. One hundred plaque-forming units were used in this experiment, and the mice were monitored for mortality for 2 weeks. Data for wild type vaccinia virus is a composite of 4 different experiments, each with 4 mice. Percent survival is plotted against days post-infection.

In addition, a domain swap study in which 67 amino acids from the murine Z-DNA binding domain (Zα) of the protein DLM-1 was substituted for 67 amino acids at the N-terminus of E3L was also performed. The domain swap resulted in only 12 residues in the domain remaining unchanged. Inoculation of mice with chimeric DLM-1-E3L virus produced a fully pathogenic phenotype. As shown in FIG. 7, inoculation of mice with vaccinia virus containing an E3L protein in which the amino-terminus was substituted with the Zα domain of murine DLM ($Z\alpha_{DLM1}$) resulted in a lethality rate similar to the rates of wild-type vaccinia (WT ($Z_{E3L}$)), and vaccinia virus containing an E3L protein in which the amino-terminus was substituted with the Z alpha domain of human ADAR1 ($Z\alpha_{ADAR1}$).

In comparing the domain swaps of human $Z\alpha_{ADAR}$ or murine $Z\alpha_{DLM}$ in vaccinia E3L, approximately 50 amino acids are changed in each of the two constructs. These 50 amino acids are not involved in Z-DNA binding or in the hydrophobic core. What is important for pathogenicity appears to be the common Z-DNA binding residues listed in FIG. 8A, which is an amino acid alignment of human Zα of ADAR1 (SEQ ID NO: 6), human Zα of DLM (SEQ ID NO: 7), E3L of vaccinia virus (SEQ ID NO: 8), E3L of variola virus (SEQ ID NO: 9), E3L of Orf virus (SEQ ID NO: 10), E3L of Lumpyskin virus (SEQ ID NO: 11), E3L of Swinepox virus (SEQ ID NO: 12), E3L of Yaba-like disease virus (SEQ ID NO: 13), E3L of Cowpox virus (SEQ ID NO: 14), and human Zβ (SEQ ID NO: 15), as well as the hydrophobic residues that maintain the fold.

Figure 9A:
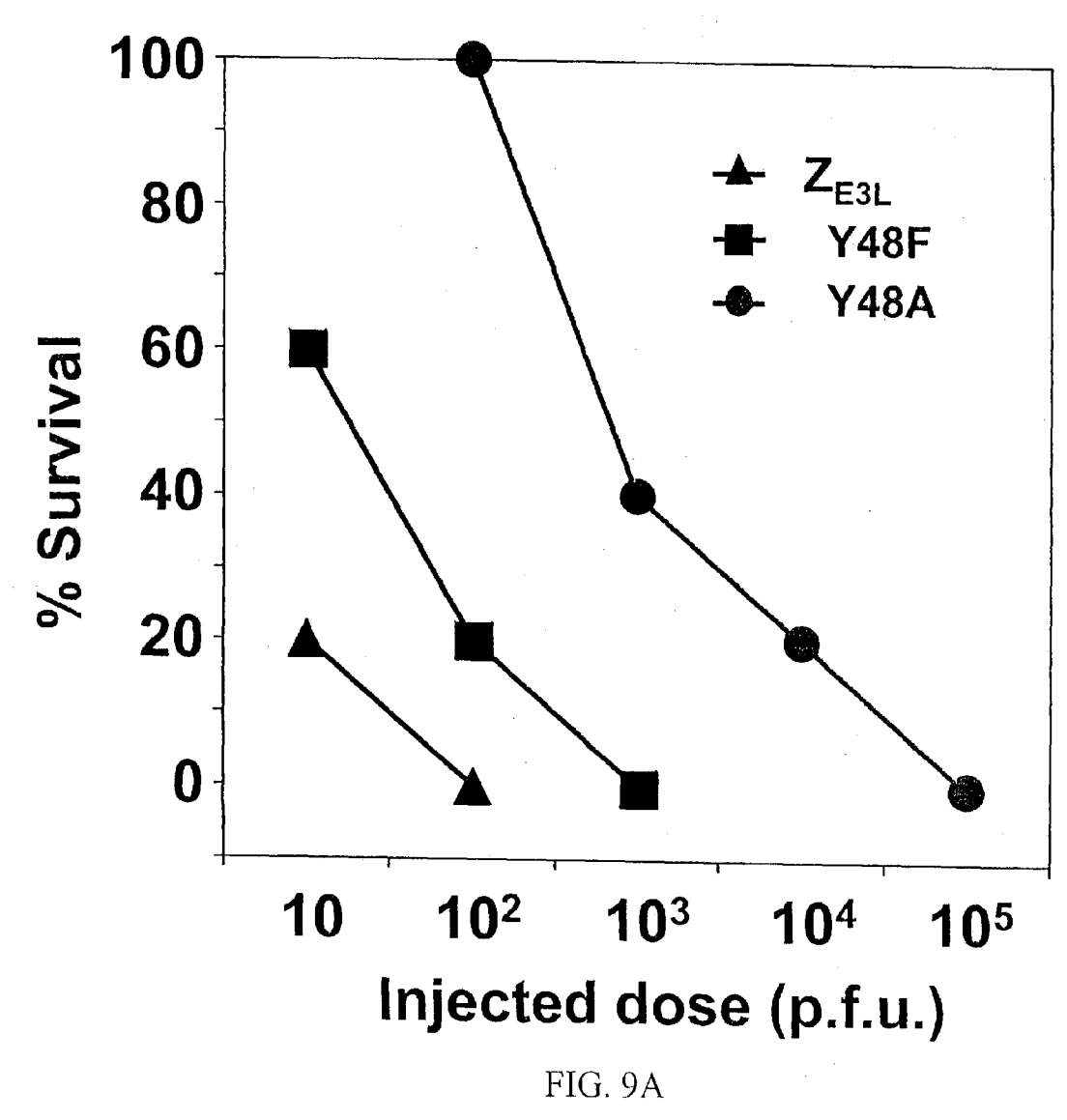

Experiments were next carried out to compare the in vivo effects of mutations in $Z\alpha_{ADAR1}$-E3L chimeric viruses and the analogous positions of wild-type vaccinia virus E3L ($Z_{E3L}$). The first set of experiments were carried out to monitor the effects of mutating tyrosine 48 (Y48) of E3L, which is analogous to tyrosine 177 (Y177) of $Z\alpha_{ADAR1}$. The dose response experiments mutating chimeric $Z\alpha_{ADAR1}$-E3L, at tyrosine 177 to phenylalanine and then alanine can be compared to similar data on mutations in the wild-type $Z_{E3L}$ at tyrosine 48 (FIG. 9A). Vaccinia virus containing a Y48F mutation was approximately 1 log less pathogenic than wild type virus, and virus containing a Y48A mutation was approximately 3 logs less pathogenic, similar to results obtained with tyrosine 177 mutations in virus containing the chimeric $Z\alpha_{ADAR}$-E3L. Thus, the biological effects in vivo are similar for tyrosine mutants in $Z\alpha_{ADAR1}$-E3L and the wild-type E3L with $Z_{E3L}$.

Figure 9C:
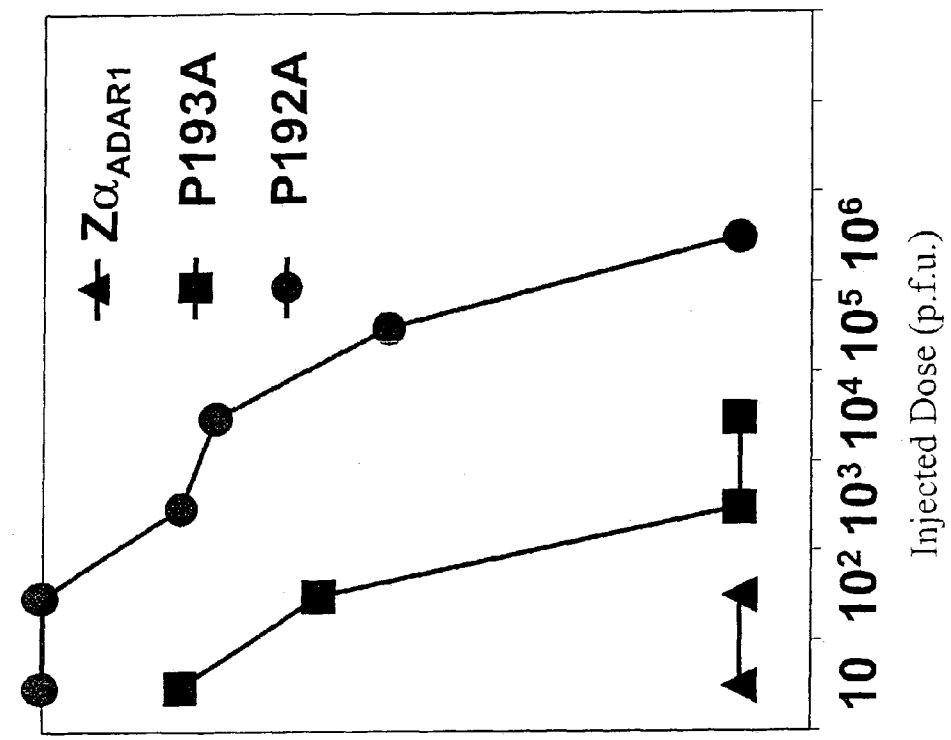
FIG. 9C is a graph of the lethality of vaccinia virus or variants in mice (percent survival) inoculated with vaccinia virus in which the human Z-DNA binding domain Zα$_{ADAR}$ containing P193A or P192A mutations has been substituted for the N-terminal domain of E3L (P193A or P192A) or with vaccinia virus in which the human Z-DNA binding domain Zα$_{ADAR}$ has been substituted for the N-terminal domain of E3L (Zα$_{ADAR1}$). Mice were infected intra-cranially with the indicated doses of chimeric virus (Zα$_{ADAR1}$), or chimeric virus containing P192A or P193A mutations.
Figure 9B:
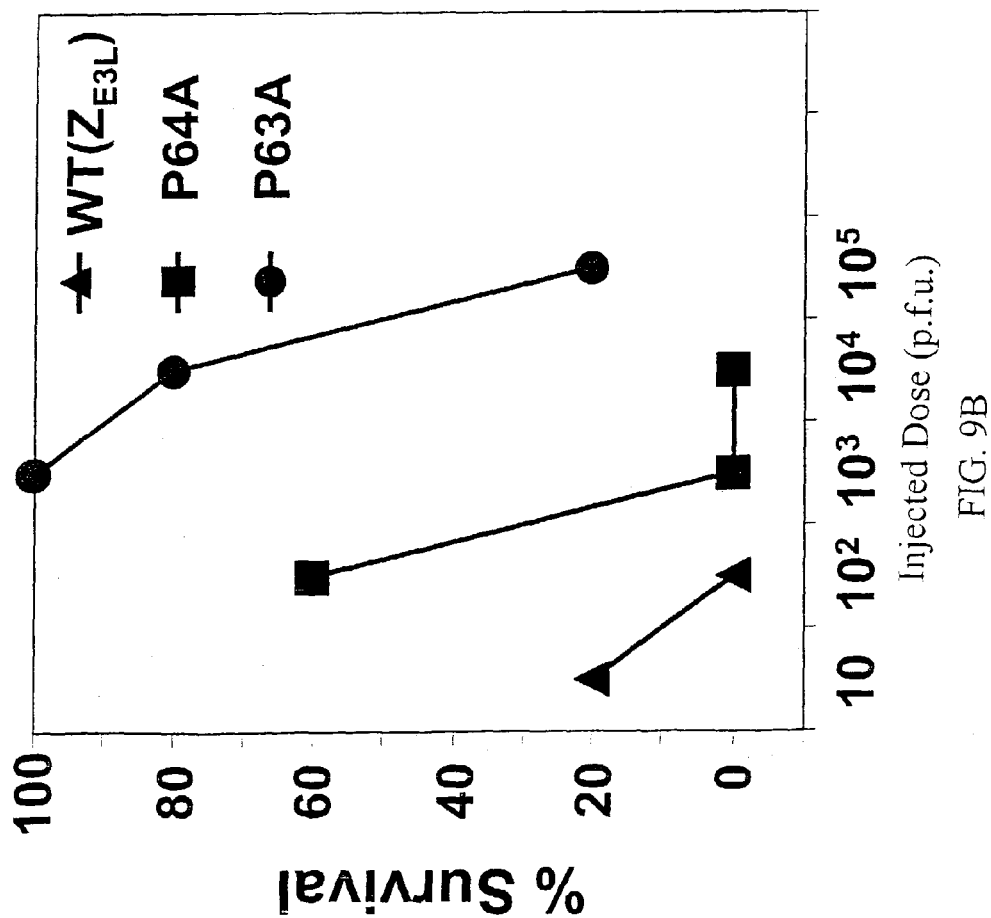
FIG. 9B is a graph of the lethality of vaccinia virus or variants in mice (percent survival) inoculated with vaccinia virus in which the human Z-DNA binding domain Zα$_{ADAR}$ containing P63A or P64A mutations has been substituted for the N-terminal domain of E3L (P64A or P63A) or with wild type E3L virus. Mice were infected intra-cranially with the indicated doses of wild type vaccinia virus (WT(ZE3L)), or with chimeric virus containing P63A or P64A mutations and assessed for survival.

Additional experiments were carried out to examine the effect of mutations in the N-terminal domain of vaccinia virus E3L and to compare these mutations with mutations in the chimeric virus in which human $Z\alpha_{ADAR}$ was substituted for the E3L N-terminal domain. Both of these molecules have two proline residues in the β3 strand. In E3L, the mutations P63A and P64A were made, and their pathogenicity measured after intracranial inoculation of the viruses. The results are similar to those shown in FIGS. 3A and 3B. Mutation P63A resulted in a complete loss of pathogenicity analogous to what was found with the mutation P192A in the ADAR1 chimeric virus (FIGS. 9B and 9C). On the other hand, the E3L mutation P64A resulted in diminished pathogenicity but not its abolition, in parallel with what is seen for the P193A mutated chimeric virus (FIGS. 9B and 9C).

Two other types of comparative mutations were also carried out. Asparagine N173 in $Z\alpha_{ADAR}$ is involved in several hydrogen bonding interactions with Z-DNA. When N173 was mutated to adenine in $Z\alpha_{ADAR}$-E3L chimeric virus, there was a significant loss of pathogenicity when inoculated into mice. Likewise, when the mutation N44A was made in the E3L virus, there was an even greater loss of pathogenicity. These functional results reinforce the interpretation that the N-terminal domain of vaccinia virus E3L is folded in a manner similar to that seen with human $Z\alpha_{ADAR}$. Selected mutations in the E3L virus affect Z-DNA binding and give rise to loss of pathogenicity comparable to what is seen in with the $Z\alpha_{ADAR}$ chimeric E3L virus.

The above additional experiments strengthen the interpretation that binding of vaccinia virus E3L to Z-DNA is an essential feature of the pathogenic mechanism in viral infection. In view of the results described herein and the near identity of the E3L N-terminal domains of variola virus and vaccinia virus shown in FIG. 8A a small molecule that inhibits the binding of variola E3L to Z-DNA is likely to interfere with viral pathogenesis.

Although the role of E3L in the nucleus is not known, once in the nucleus, the E3L molecule may bind to the Z-DNA segments that form near the transcription start site of an actively transcribing gene. The C-terminal domain may then bind a transient hairpin or double-stranded segment formed in the pre-mRNA of that gene. The binding of both the mRNA and the DNA is likely to inhibit the transcription of the gene. There may thus be an impairment of the ability of the cell to respond to infection by upregulating the interferon-inducible genes.

Thus, agents that inhibit the interaction or complex formation between a Z-DNA binding ligand or variant and Z-DNA are useful in inhibiting the pathogenic effects resulting from binding of a Z-DNA binding ligand or variant to Z-DNA. Such an inhibitor can be used to treat patients that have been infected with an infectious agent, for example, a virus.

EXAMPLE 3

Detection of Z-DNA Binding Proteins Using a Yeast One-Hybrid System

The yeast one-hybrid system has been used as a tool for identifying proteins that bind to specific DNA sequences (Allen et al., Trends Biochem. Sci., 20:511–6, 1995; Liu et al., Methods, 5:125–37, 1993). The upstream activating sequence (UAS) of a reporter gene is replaced by a bait sequence, and DNA binding proteins are then expressed in yeast cells as fusion proteins with a transcriptional activation domain. Thus, transcription is activated when the DNA binding protein fused to the activation domain interacts with the bait DNA sequence. This system has been expanded to include DNA conformational specificity with Z-DNA formation. This assay allows for the identification and characterization of Z-DNA specific binding proteins in vivo and for the study of the influence of Z-DNA formation on transcriptional activity.

As described herein, Z-DNA is a left-handed form of the double helix, as revealed in a single-crystal X-ray analysis of duplex d(CGCGCG) (Wang et al., Nature, 282:680–686, 1979). The Watson-Crick base pairs in Z-DNA have "flipped over" relative to their orientation in B-DNA, resulting in the guanine residues adopting the syn conformation, while the cytosine residues remain in the anti conformation. Since purines adopt the syn conformation more readily than pyrimidines, Z-DNA is favored in sequences with alternations of purines and pyrimidines. The most favored sequence consists of (dC-dG)$_n$ although many other sequences can also adopt the Z conformation (Rich et al., Annu. Rev. Biochem., 53:791–846, 1984).

Z-DNA is a higher energy conformation than right-handed B-DNA, and it was realized that conversions of this type could occur in vivo when it was discovered that Z-DNA is stabilized by negative supercoiling (Peck et al., Proc. Natl. Acad. Sci. USA, 79:4560–4564, 1982). Formation of Z-DNA removes negative supercoiling, and the energy of supercoiling stabilizes the Z conformation. It has been shown that the movement of RNA polymerase generates negative torsional strain behind it (Liu and Wang, Proc. Natl. Acad. Sci. USA, 84:7024–7027, 1987) and that Z-DNA sequences near the promoter region are maintained in the left-handed conformation in mammalian nuclei as long as the gene is actively transcribed (Wittig et al., EMBO J., 11:4653–4663, 1992). Furthermore, sequences that form Z-DNA readily occur with great frequency near the transcription start site (Schroth et al., J. Biol. Chem., 267: 11846–11855, 1992). The yeast one-hybrid system is organized so the influence on transcription of Z-DNA formation near the promoter can be measured. Z-DNA can also be stabilized by specific Z-DNA binding proteins, and several have been included in the studies described herein. As described herein, a protein domain hZα$_{ADAR}$ from the editing enzyme double-stranded RNA adenosine deaminase (ADAR1) has been identified and found to bind to Z-DNA. If hZα$_{ADAR}$ is added to DNA with a Z-DNA forming sequence in its center, it will bind to the sequence, even when it is surrounded by B-DNA (Kim et al., J. Biol. Chem., 275: 26828–26833, 2000). The murine tumor-related protein DLM is also known to bind Z-DNA through a Zα domain, showing that there is a family of such Z-DNA binding proteins. Another member of this family is the N-terminal domain of the vaccinia virus E3L (vZ$_{E3L}$), as described herein. hZα$_{ADAR}$ and mZα$_{DLM}$ are known to bind Z-DNA tightly and specifically, but vZ$_{E3L}$ is much less active in vitro. However, when used in the conformationally specific yeast one-hybrid system described herein in vivo, all three of these proteins bind to Z-DNA. By studying these Z-DNA binding proteins plus a number of engineered variants, it can be demonstrated that these proteins are involved in enhancing transcription.

Material and Methods

Yeast Strain and Construction of Reporter Plasmids

Yeast strain YM4271 was purchased from Clontech (Palo Alto, Calif.) (Wilson et al., Science, 252:1296–1300, 1991) and used for all yeast experiments described herein. Vector constructs were modified from the vectors used in the MATCHMAKER yeast hybrid system (Clontech, Palo Alto, Calif.). Reporter vectors were constructed using the pLacZi vector as a template and expression vectors were constructed using either pACT2 or pGAD-GH (Clontech, Palo Alto, Calif.).

Target sequences were inserted into the reporter vectors using duplex DNA oligomers. Oligonucleotides sequences were 5'-CCGAATTCGTCGGT(CG)$_n$ACCGACCTC-GAGTCTAG AGC-3' (SEQ ID NOs:22–26) and 5'-GCTCTAGACTCGAGGTCGGT(CG)$_n$ACCGAC-GAATTCGG-3' (SEQ ID NOs: 27–31), where n is 0 for the control, or n=4, 5, 9 or 12. Each pair of oligonucleotides was annealed to form duplex DNA and it was then digested with appropriate restriction enzymes, EcoRI and XhoI for pLacZi-based vectors. DNAs were purified and ligated to reporter vector DNAs digested with comparable pairs of restriction enzymes.

The LacZ gene reporter vectors, named pLacZcOp-Control or pLacZcOp-(dC-dG)$_n$ (where n is 4, 5, 9 and 12) have a centromere element for self-propagation in yeast. It was made by inserting a PCR-amplified CEN6/ARSH4 containing a DNA fragment from pRS313 between the URA3 gene and the Amp$^r$ gene of the pLacZi vector. Finally, each target sequence (Control, or (dC-dG)$_n$) was inserted into EcoRI and XhoI sites upstream of the LacZ reporter gene. The resulting pLacZcOp vectors with their target sequence inserts were named pLacZcOp-Control and pLacZcOp-(dC-dG)$_n$. The inserted target sequences were confirmed by dideoxy sequencing.

To construct the pLacZcSm vector, an entire URA3 transcription unit including promoter and terminator was PCR-amplified from pLacZcOp with primers 5'-CGGAAT-TCAGCACGCCATAGTGACTGG-3' (SEQ ID NO: 32) and 5'-GACTAGCTAGCTCAAGCTTTTCA ATTCATCATTT-3' (SEQ ID NO: 33). The amplified DNA was then cloned into pLacZcOp to replace the existing URA3 gene. The resulting plasmid, pLacZcSm, had the same orientation of transcription in both the URA3 gene and the LacZ gene. The target sequences were then introduced into pLacZcSm with the fragments which were derived from pLacZcOp-Control or (dC-dG)$_n$.

Construction of Yeast Expression Vectors for Z-DNA Binding Proteins with or without Activation Domain (AD) Fusion Gene fragments of Zα motif proteins were prepared from their pET28a (Novagen, Madison, Wis.) bacterial expression vector constructs. The fragments used were hZα$_{ADAR}$(aa 133–209) and hZab$_{ADAR}$(aa 133–368) from human ADAR1 (GenBank Accession Number: U18121) as described by Schwartz et al. (J. Biol. Chem., 274:2899–28906, 1999). The engineered Zα motif, hZaa$_{ADAR}$, and the mutant, hZa'b$_{ADAR}$ (I172F and N173A in hZab$_{ADAR}$), were as described previously (Kim et al., J. Biol. Chem., 275:26828–26833, 2000, and Kim et al., J. Biol. Chem., 274:19081–19086, 1999). mZ$_{DLM}$ (aa 8–70) was from mouse DLM-1 (GenBank Accession Number: AF136520) described previously by Schwartz et al. (Nat. Struct. Biol., 8:761–765, 2001). In addition, the following constructs were made for this study: hZβ$_{ADAR}$ (aa 294–368) and the mutant, hZα$_{N173A}$(N1$^{73}$A in hZαADAR) were from human ADAR1, and vZ$_{E3L}$(aa 1–78) was from vaccinia virus E3L (GenBank Accession Number: S64006). NcoI and XhoI digested fragments were inserted into pACT2 at NcoI and XhoI sites. The resulting vectors produced fusion proteins with the Gal4 activation domain (AD) at the N-terminus in yeast. The fusion proteins are able to enter the nucleus because the N-terminal SV40 T antigen nuclear localization signal (NLS) was located at the N-terminus of the AD.

To construct a vector producing proteins without an AD in yeast, the Gal4 activation domain was deleted by KpnI digestion from pGAD-GH (Clontech, Palo Alto, Calif.). However, the resulting vector still contained the NLS for entering the nucleus. By inserting a linker containing NcoI and XhoI sites at the KpnI site, the vector named pGNA was created for cloning the desired protein genes in yeast.

Yeast One-Hybrid Analysis with Quantitative and Qualitative β-Galactosidase Activity Assay Yeast strain YM 4271 was transformed with the LacZ reporter vectors (either pLacZcOp or pLacZcSm) using the lithium acetate polyethylene glycol method described elsewhere (Gietz et al., Yeast, 11:355–360, 1995). The o-nitrophenyl-β-D-galactose (ONPG) assay was used for a quantitative assay of β-galactosidase activity according to the manufacturer's instructions (Clontech, Palo Alto, Calif.). Mean and standard deviations were calculated from triplicates in Miller's β-galactosidase units in which 1 unit hydrolyzes 1 μmol of o-nitrophenyl-β-D-galactose (ONPG) per minute per cell.

For a colorimetric assay of β-galactosidase using plates with X-gal, freshly transformed yeast cells on selection plates were picked and streaked onto new plates containing 80 μg/ml X-gal and a selection medium lacking uracil and leucine. After incubating at 30° C., a blue color developed if β-galactosidase was produced from the LacZ reporter gene. pGNA-based vector transformed cells took longer (2–3 days) to develop color than the pACT2-based vector cells (1–2 days).

B-Z Midpoint Assay

Poly (dG-dC) (Amersham Pharmacia Biotech, Piscataway, N.J.) was purchased, re-hydrated with tris buffer (10 mM Tris-Cl, pH 7.4, and 50 mM NaCl) and stored at −20° C. prior to use. Poly (dG-dC) can be driven to the Z-conformation as monitored by circular dichroism (CD) with a variety of salts including NaCl (Pohl and Jovin, J. Mol. Biol., 67: 375–396, 1972) and cobalt hexaamine (Co $(NH_3)_6^{3+}$) (Behe and Felsenfeld, Proc. Natl. Acad. Sci. USA, 78:1619–23, 1981). NaCl requires a high concentration (above 2 M) to convert a significant portion to Z-DNA in solution. Therefore, a high concentration of NaCl (2.5 M) was used to generate the midpoint of B-Z equilibrium and it has been used to test for conformational binding specificities of intercalating small molecules (Qu et al., Proc. Natl. Acad. Sci. USA, 97:12032–12037, 2000). However, this solution was not suitable for testing the DNA binding of proteins. Since cobalt hexaamine is more portent in stabilizing Z-DNA at very low concentration, it is more suitable for this purpose. Thus, cobalt hexaamine was used to create a B-Z equilibrium mixture in poly (dG-dC). In brief, 40 μg/ml concentration of DNA was incubated with 70–80 μM cobalt hexaamine (Sigma, St. Louis, Mo.) overnight at 25° C. About a 1:1 ratio in the B-Z equilibrium measured by the CD spectrum was desirable for a sensitive assay. Since it was very sensitive to small changes in salt concentration, multiple samples with different concentrations of cobalt hexaamine were usually prepared and a sample with the desired B-Z equilibrium was then used for the assay. CD spectra were taken at 25° C. using an AVIV model 202 CD instrument. Measurements were carried out using 40 μg/ml or 60 μM (base pair) of DNA at 25° C. in a 2 mm quartz cell. Spectra for wavelength scanning were recorded at a 1 nm interval averaged over 3 seconds. Sixty 1M of protein were then added to the sample from a concentrated stock solution. The maximum volume of protein added to the sample did not exceed 5% of the total volume. For kinetic measurements, CD signal changes at 292 nm were recorded at 1-second intervals.

Results

Figure 10A:
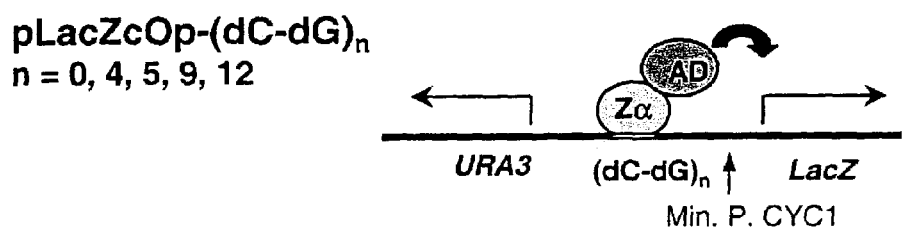
FIG. 10A is a schematic representation of a reporter vector used to carry out the yeast one-hybrid assay described herein. For reporter vector construction, bait sequences of various repeats of (dC-dG) were inserted between the reporter gene (LacZ) and the URA3 gene. The orientation of the selection marker gene, URA3, created favorable (opposite or Op) conditions for Z-DNA formation. In the pLac-ZcOp vector, the orientation of URA3 transcription was opposite to that of the LacZ reporter gene. As shown diagrammatically with pLacZcOp, transcription of the LacZ reporter gene was activated when h Zα$_{ADAR1}$ carrying an activation domain (AD) bound to Z-DNA. The Zα-AD hybrid fusion was expressed from an independent vector, pACT2-Zα.
Figure 10B:
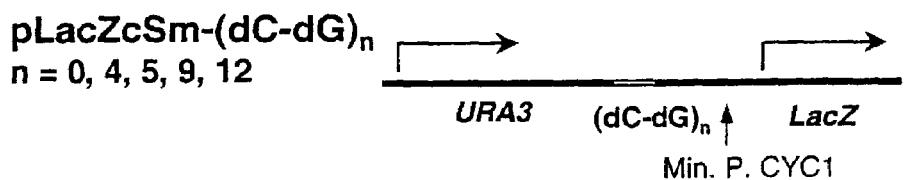
FIG. 10B is a schematic representation of a reporter vector used to carry out the yeast one-hybrid assay described herein. For reporter vector construction, bait sequences of various repeats of (dC-dG) were inserted between the reporter gene (LacZ) and the URA3 gene. The orientations of the selection marker gene, URA3, created unfavorable (same or Sm) conditions for Z-DNA formation. Transcriptions from both URA3 and LacZ had the same orientation in the pLacZcSm vector. The Zα-AD hybrid fusion was expressed from an independent vector, pACT2-Zα.

Reporter Vector Constructs Designed to Include Z-DNA Stabilized by Negative Supercoiling In order to modify the yeast one-hybrid system to study Z-DNA formation and the role of its binding proteins, reporter vectors were constructed containing alternating dC-dG stretches (FIGS. 10A and 10B). Alternating dC-dG is the sequence with the highest propensity to form Z-DNA, and even short repeats are stable in the Z-conformation in a supercoiled plasmid (Kim et al. J. Biol. Chem., 271:9340–9346, 1996). It has been shown that transcription of RNA from a DNA template produces negative supercoiling behind the moving RNA polymerase (Liu and Wang, supra). Negative supercoiling stabilizes Z-DNA in appropriate sequences (Peck et al., supra), therefore (dC-dG) segments upstream of an active promoter are converted to the Z-conformation. This mechanism was utilized by placing the (dC-dG) sequence between the reporter gene LacZ gene with an upstream CYC1 minimal promoter and a constitutively expressed URA3 gene with the opposite orientation of its promoter (FIG. 10A, pLacZcOp-(dC-dG)$_n$ (Op)). The steady transcription of URA3 thus results in conversion of (dC-dG)$_n$ to Z-DNA. As shown diagrammatically in FIG. 10A, binding of the Zα domain of human ADAR1 (hZα$_{ADAR}$) or other Z-DNA binding proteins fused to the activation domain (AD) should result in the activation of transcription of LacZ. Production of β-galactosidase, the LacZ gene product, can be quantitated by the ONPG assay. The sensitivity of this system is likely to be increased because expression of the LacZ gene will also increase the negative superhelicity of the region between URA3 and LacZ, thereby enhancing Z-DNA formation.

An additional plasmid, pLacZcSm-(dC-dG)$_n$ (Sm), shown in FIG. 10B, was constructed as a control to assess the Z-DNA specificity of binding. Positive supercoiling generated from transcription of the URA3 gene by RNA polymerase produces an unfavorable environment for Z-DNA formation at the (dC-dG)$_n$ sequence. Proteins specific for the B-conformation of (dC-dG)$_n$ sequence will bind Sm as well as or better than Op, depending on whether Z-DNA formation is inhibitory to their sequence specific binding. In contrast, Z-DNA binding proteins will bind preferentially in the Op orientation, with binding to Sm dependent upon the ability of the Z-DNA binding protein to independently stabilize Z-DNA.

Figure 11A:
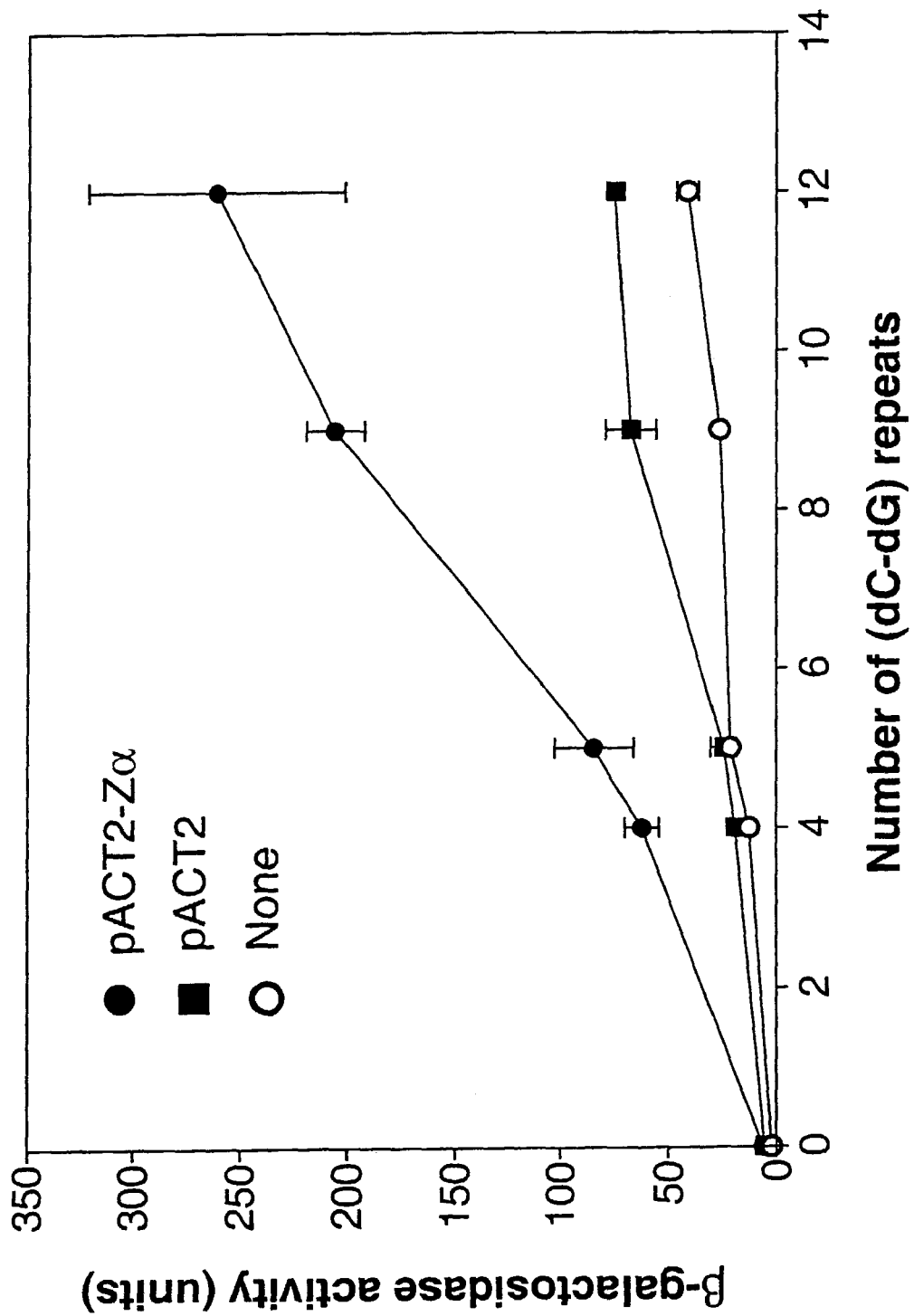
FIG. 11A is a graph showing activation of transcription, assessed by βgalactosidase activity as a function of the number of (dC-dG) repeats used in the yeast one-hybrid assay described herein, using pLacZcOp transfected with pACT2 or pACT2-Zα expression vectors encoding a Zα-AD hybrid fusion protein containing hZα$_{ADAR}$, or a control (none) containing no Zα protein. The Zα-AD fusion protein activated transcription of the LacZ reporter gene by binding to upstream Z-DNA forming bait sequences. pLac-ZcOp vectors were transfected into yeast either without (none) or with pACT2 or the pACT2-Zα expression vectors containing hZα$_{ADAR1}$.
Figure 11B:
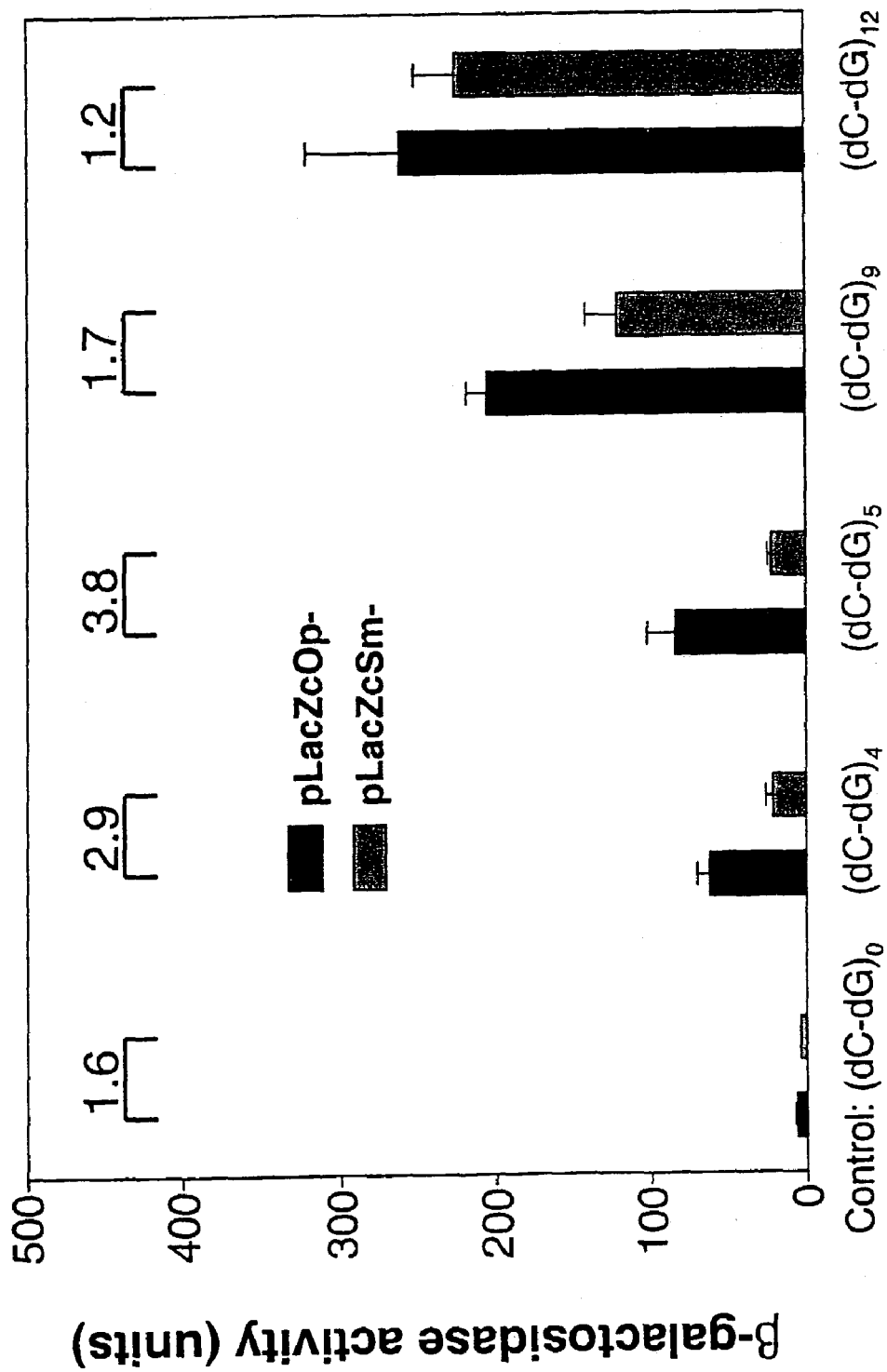
FIG. 11B is a histogram showing a comparison of activation of the LacZ gene by the Zα-AD fusion protein in different reporter vectors, pLacZcOp and pLacZcSm using various lengths of (dC-dG) repeats in the yeast one-hybrid assay described herein. The numbers above the bars represent the fold increase of the enzyme activity in pLacZcOp compared to pLacZcSm.

The length of the alternating dC-dG sequence can affect the results of these experiments. There are optimal sizes for both Z-DNA formation and protein binding. The Op plasmids were transfected into yeast (a) alone, or (b) with a plasmid expressing only an activation domain (pACT2), or (c) with a plasmid expressing the activation domain attached to hZα$_{ADAR}$. FIG. 11A shows that the amount of β-galactosidase activity increased approximately linearly with increasing number of dC-dG repeats in the presence of Zα attached to an activation domain. In the absence of hZα$_{ADAR}$, either with or without pACT2, there was only minimal enzyme activity if the number of repeats was less than five. At higher repeat numbers there was a slight increase in activity, even in the absence of an activation domain. This suggests that formation of Z-DNA near a promoter may itself act as an enhancer. This observation is investigated further and discussed later.

β-galactosidase was induced in the presence of hZα$_{ADAR}$ in the Sm plasmid as well as Op (FIG. 11B). This induction in Sm is likely to reflect the fact that the high affinity hZα$_{ADAR}$ is sufficient to stabilize the Z-conformation in dC-dG repeats even within a B-DNA environment (Kim et al., J. Biol. Chem., 275: 26828–26833, 2000). Although induction was roughly comparable at high repeat number, there was a significant difference at shorter lengths. Op showed dramatic induction in (dC-dG)$_4$ containing plasmids, while Sm had only modest enzyme activity below (dC-dG)$_9$. The plasmids containing (dC-dG)$_4$ and (dC-dG)$_5$ contained only a single hZα$_{ADAR}$ binding site per strand, based on the crystal structure of hZα$_{ADAR}$:DNA (Schwartz et al., Science, 284:1841–1845, 1999). This may not be enough to stabilize Z-DNA in the absence of supercoiling. The longer repeats contain multiple binding sites, which can act together to stabilize Z-DNA even in the absence of supercoiling. The same phenomenon was demonstrated in vitro by enhancement of the cleavage by a Z-DNA specific nuclease in a sequence containing multiple Zβ binding sites, in the presence of excess $hZ\alpha_{ADAR}$ (Kim et al., J. Biol. Chem., 275: 26828–26833, 2000).

$hZ\beta_{ADAR}$ Does Not Bind Z-DNA

Although $hZ\alpha_{ADAR}$ is a stable protein domain by itself, partial proteolysis of the N-terminus of human ADAR1 shows that it is included in a larger domain, called $hZab_{ADAR}$ (Schwartz et al., 1999a). This domain consists of $hZ\alpha_{ADAR}$, as well as a second region, $hZ\beta_{ADAR}$, closely related by sequence. In addition, there is an intervening linker, which is tandemly duplicated in humans. The in vitro binding of Z-DNA by $hZab_{ADAR}$ resembles but is not identical to that of $hZ\alpha_{ADAR}$ (Schwartz et al., J. Biol. Chem., 274:2899–2906, 1999). Although $hZ\beta_{ADAR}$ is very similar in sequence to $hZ\alpha_{ADAR}$, it has not been possible to show binding of Z-DNA by $hZ\beta_{ADAR}$ in vitro.

A number of constructs have been designed to examine the binding of $hZab_{ADAR}$ to DNA, and the roles of the two related sub-domains. In $hZa'b_{ADAR}$, a double mutation in $hZab_{ADAR}$ (I172F and N173A) (Kim et al., 2000) virtually abolishes its ability to bind Z-DNA. Thus, $hZa'b_{ADAR}$ does not bind Z-DNA detectably in vitro (Kim et al., J. Biol. Chem., 275: 26828–26833, 2000). $hZaa_{ADAR}$ is a construct that contains a second $hZ\alpha_{ADAR}$ motif replacing $hZ\beta_{ADAR}$ in $hZab_{ADAR}$ (Kim et al., J. Biol. Chem., 274: 19081–19086, 1999). $hZaa_{ADAR}$ binds Z-DNA with a higher affinity than either $hZ\alpha_{ADAR}$ or $hZab_{ADAR}$.

Figure 12:
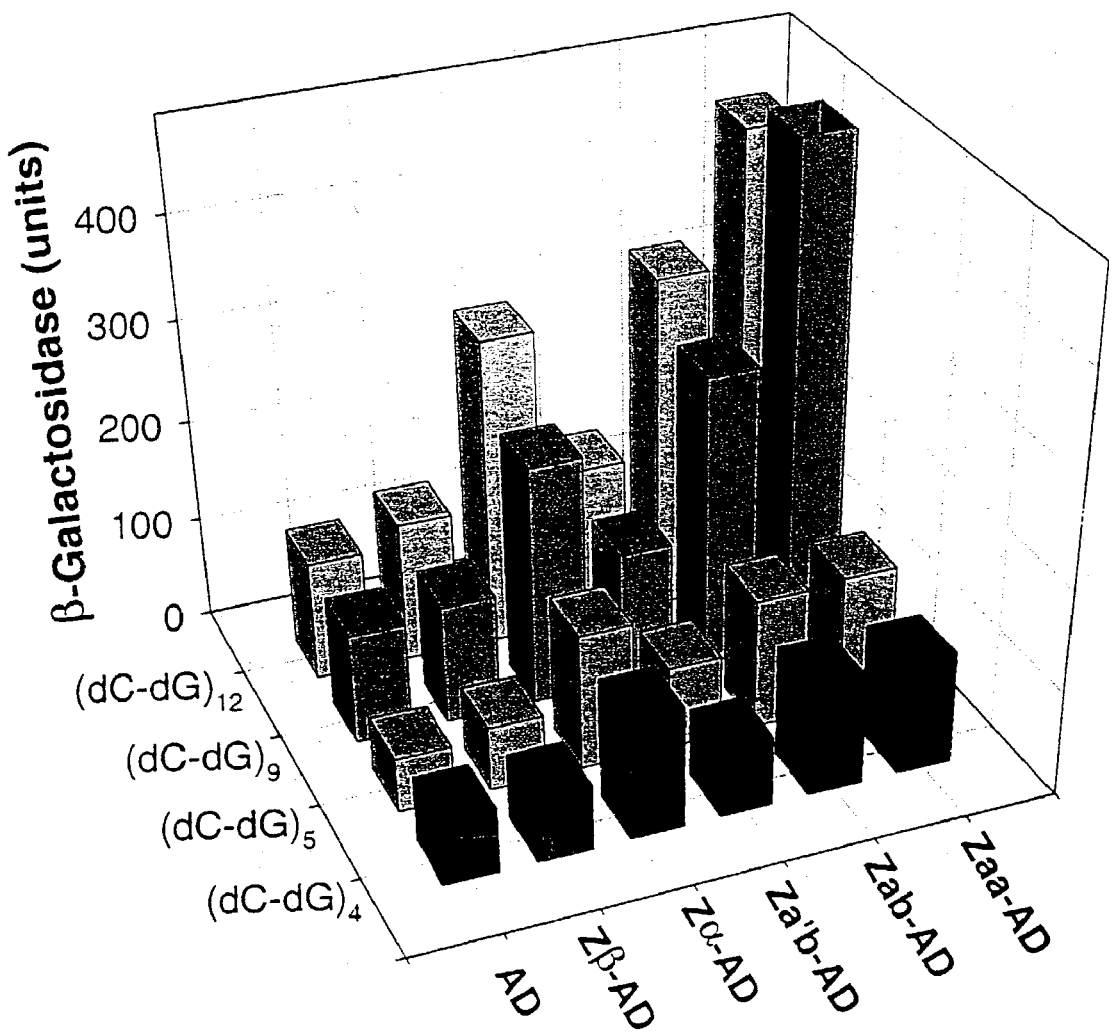
FIG. 12 is a histogram of the Z-DNA binding activities of Zα, Zβ, Za'b, Zab and Zaa using LacZ reporter gene activation and various lengths of (dC-dG) repeats. Zα, Zβ and Zab all came from human ADAR1. In Zaa, the Zβ domain of Zab was removed and Zα replaced it. Za'b had mutations in Zα of Zab. Vectors containing an activation domain fused to nothing (pACT2) or to various human Zα, Zβ or Zab constructs from human ADAR1 (pACT2-Zβ, -Zα, -Zab, -Za'b and -Zaa) were co-transfected into yeast with pLacZcOp-(dCdG)$_n$ (where n=4, 5, 9, and 12). β-galactosidase activities were determined by a quantitative o-nitrophenyl-β-D-galactose (ONPG) assay.

Examination of in vivo binding of Z-DNA by these various peptides agreed well with in vitro results (FIG. 12). FIG. 12 shows activation of the LacZ gene by various peptides in the presence of varying lengths of alternating (dC-dG). $hZ\beta_{ADAR}$ and $hZa'b_{ADAR}$ showed no significant increase of activation above the pACT2 control, while $hZ\alpha_{ADAR}$, $hZab_{ADAR}$ and $hZaa_{ADAR}$ all produced activation of the LacZ gene. When the reporter construct contained only four or five repeats of (dC-dG), all three of these proteins behaved identically. With longer repeats, $hZab_{ADAR}$ activated LacZ in a manner similar to $hZ\alpha_{ADAR}$, while $hZaa_{ADAR}$ was dramatically better. In $hZaa_{ADAR}$, it is likely that the two copies of $hZ\alpha_{ADAR}$ act cooperatively when positioned next to each other resulting in higher level of activation.

When reporter vectors Op and Sm containing four repeats of dC-dG were compared on X-gal plates, it was clear that the presence of a Z-DNA binding domain, either $hZ\alpha_{ADAR}$ or $hZaa_{ADAR}$, with divergent promoters (Op) produced the most β-galactosidase activity. Even in the absence of stabilizing negative superhelicity (Sm), $hZ\alpha_{ADAR}$ and $hZab_{ADAR}$ had some stimulatory effect, as was previously shown in FIG. 11B. The presence of $hZ\beta_{ADAR}$ had no effect, indicating that $hZ\beta_{ADAR}$ does not bind to the promoter region. The level of β-galactosidase activity in the presence of $hZ\beta_{ADAR}$ was the same as the activation domain alone. This indicates that $hZ\beta_{ADAR}$ does not bind Z-DNA in vivo, in agreement with in vitro results.

$mZ\alpha_{DLM}$ and $vZ_{E3L}$ Bind Z-DNA in Vivo

Figure 13:
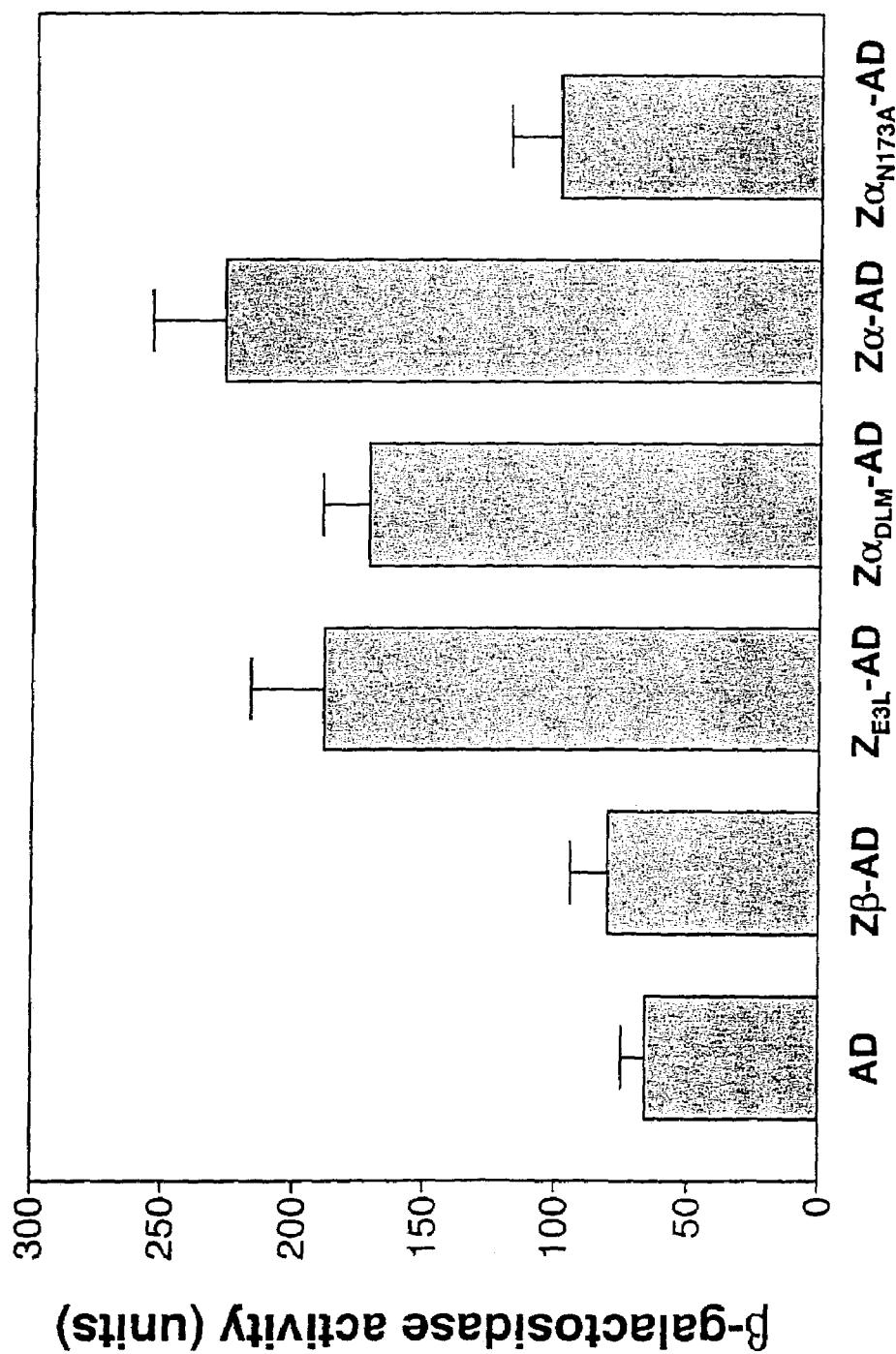
FIG. 13 is a histogram showing Z-DNA specific binding of Zβ or Zα homologues in vivo, as assessed by measuring β-galactosidase reporter activity in yeast containing various vectors containing an activation domain fused to human Zβ or Zα constructs from human ADAR1. Vectors coding for Zα or its homologues in the pACT2 vector were transfected into yeast cells carrying a reporter vector, placZcOp-(dC-dG)$_9$. All constructs were fused to an activation domain except pACT2 which had only an activation domain. The β-galctosidase activity was determined quantitatively by o-nitrophenyl-β-D-galactose (ONPG) assay. Z$_{E3L}$ and Zα$_{DLM}$ were N-terminal Zα homologous domains from vaccinia virus E3L protein and mouse DLM-1, respectively. Zα$_{N173A}$ was a mutant with significantly reduced Z-DNA binding activity because of the change in the conserved Asn173 to Ala of hZα$_{ADAR}$.

Sequences with significant similarity to $hZ\alpha_{ADAR}$ have been found in a number of vertebrate proteins (Herbert et al., Proc. Natl. Acad. Sci. USA, 94:8421–842 6, 1997; Schwartz et al., Nat. Struct. Biol., 8:761–65, 2001). Two of these, $mZ\alpha_{DLM}$ and $vZ_{E3L}$ have been studied for Z-DNA binding in vitro. $mZ\alpha_{DLM}$ is located at the N-terminus of murine DLM-1, which was first identified as a tumor related interferon inducible protein (Fu et al., Gene, 240:157–163, 1999). DLM-1 has two motifs, Zα and Zβ, similar to ADAR1 (Schwartz et al., 2001, supra). $mZ\alpha_{DLM}$ binds Z-DNA tightly and specifically in vitro. Its crystal structure with Z-DNA has been solved and it is very similar to the $hZ\alpha_{ADAR}$-Z-DNA complex (Schwartz et al., 2001, supra). $Z_{E3L}$ is located at the N-terminus of the EL3 protein from vaccinia virus and it is far less effective in binding Z-DNA in vitro. However, when these peptides are examined in the yeast one-hybrid assay, both are effective in Z-DNA binding (FIG. 13). $vZ_{E3L}$ and $mZ\alpha_{DLM}$ behaved in vivo almost identically to $hZ\alpha_{ADAR}$ in both quantitative (FIG. 13) and qualitative assays. This was in contrast to in vitro studies in which $hZ\alpha_{ADAR}$ and $mZ\alpha_{DLM}$ bound Z-DNA with the same affinity (Schwartz et al., 2001, supra), while vZE3L bound poorly. It is possible that the different results in vivo and in vitro reflect a difference in the local environment of binding or the presence of the other proteins, which may alter the stability or folding of these domains.

In an engineered variant, $hZ\alpha_{N173A}$ was made with a mutation (N173A) that eliminated one direct and two water-mediated contacts between $hZ\alpha_{ADAR}$ and Z-DNA (Schwartz et al., J. Biol. Chem., 274:2899–2906, 1999). This mutation ($hZ\alpha_{N173A}$) suppressed Z-DNA binding in vitro (Schade et al., EMBO J., 18:470–479, 1999) and in vivo, as shown in FIG. 13. With the exception of vZE3L, the results shown in both the quantitative assay (FIG. 13) and on X-gal plates confirm that the Z-DNA binding activities in vivo are parallel to those demonstrated in vitro.

EXAMPLE 4

Figure 14A:
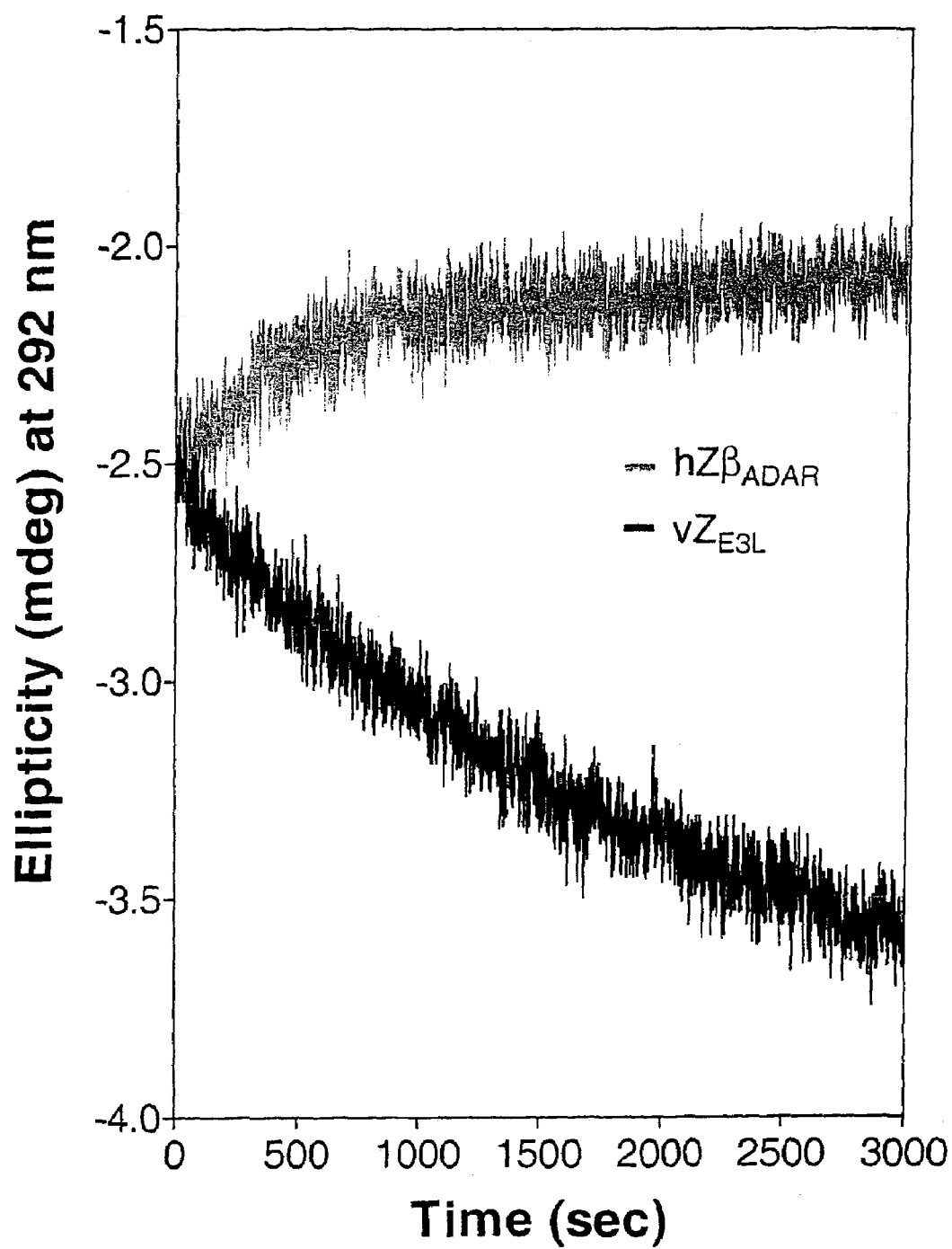
FIG. 14A is a graph showing the results of a sensitive circular dichroism (CD) assay for Z-DNA binding specificity using the B-Z equilibrium at midpoint, as described herein. The CD midpoint of the B-Z equilibrium of poly (dC-dG) was achieved by adding cobalt hexaamine. If a protein bound specifically to the Z-conformation of DNA rather than the B-conformation, the equilibrium between B- and Z-conformations changed toward Z-DNA. Likewise, a B-conformation specific binding protein changed toward B-DNA. Sixty μM of protein was added into 60 μM (base pair) of poly (dC-dG) DNA at the midpoint of the B-Z equilibrium. The shift of B-Z equilibrium was monitored with CD at 292 nm for 3000 seconds. vZ$_{E3L}$ (dark line) showed an apparent Z-DNA specificity by changing the CD signal to the Z-conformation, while hZβ$_{ADAR}$ (light line) was the opposite.
Figure 14B:
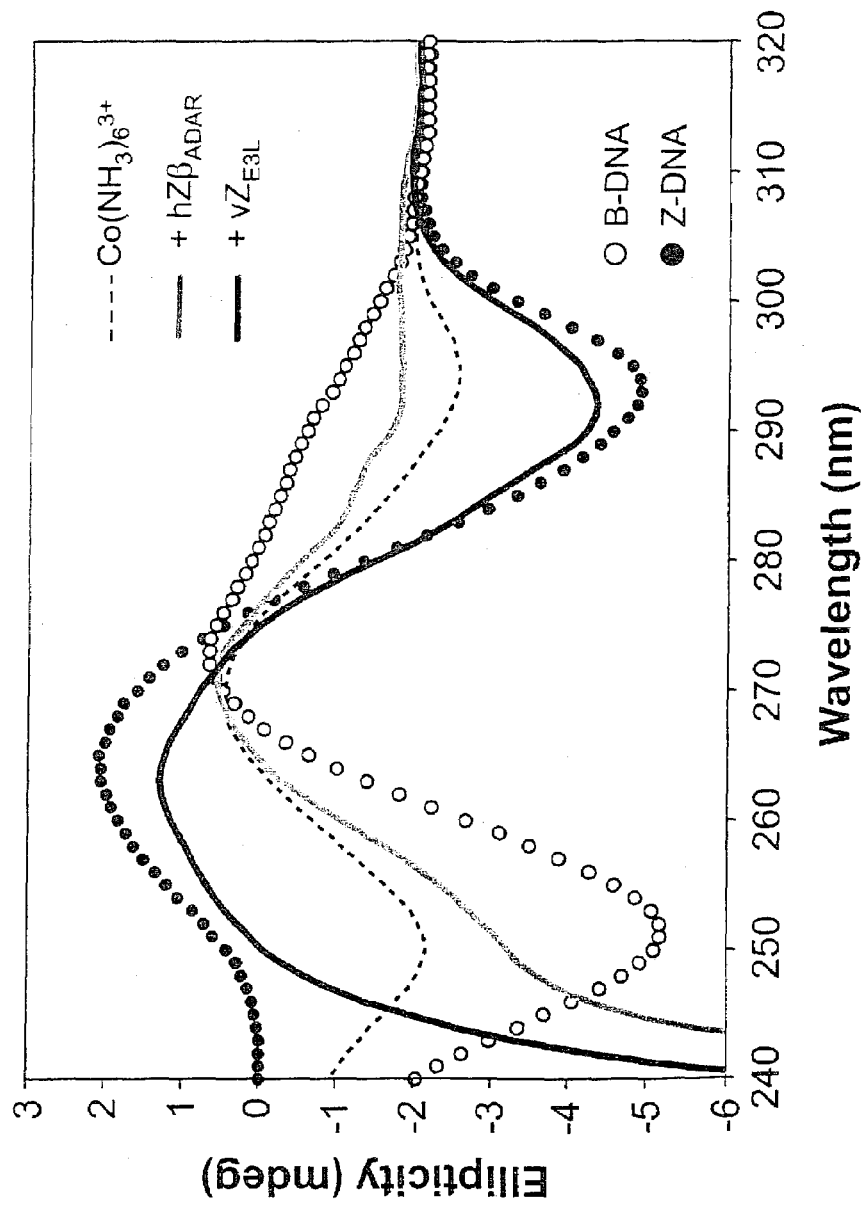
FIG. 14B shows CD spectra between 240 nm and 320 nm that were taken at 20 hours after proteins were added in the assays described in FIG. 14A. The B-Z midpoint spectrum (----) was achieved by adding cobalt hexamine around 75 μM. Characteristics of the conformational specificity of cZ$_{E3L}$ (dark line) and hZ(3ADAR (light line) are shown.

Detection of $vZ_{E3L}$ Binding to Z-DNA in Vitro in an Equilibrium Mid-Point Assay The initial in vitro evidence that $vZ_{E3L}$ was a Z-DNA binding protein has been weak. By sequence, it is very similar to $hZ\alpha_{ADAR}$ and $mZ\alpha_{DLM}$. However, unlike $hZ\alpha_{ADAR}$ and $mZ\alpha_{DLM}$, $vZ_{E3L}$ does not convert the CD spectrum of $(dC-dG)_6$ from the B-form to the Z-form, and in a gel mobility shift it produces weak binding and a smear. Similarly, $hZ\beta_{ADAR}$ does not change the CD spectrum by shifting $(dC-dG)_6$ from the B- to Z-conformation and it does not show Z-DNA binding activity in the gel-mobility shift assay. However, the strong evidence for Z-DNA binding activity of $vZ_{E3L}$ in vivo provided by the yeast one-hybrid assay described herein prompted the development of a new and more sensitive in vitro assay for Z-DNA binding. In this assay, cobalt hexaamine (Behe and Felsenfeld, Proc. Natl. Acad. Sci. USA, 78:1619–1623, 1981) is added to $(dC-dG)_6$ to a concentration at which the DNA is a mixture of the B-form and Z-form in approximately a 1:1 ratio as assessed by circular dichroism (CD). Addition of protein can (a) have no effect or (b) drive the equilibrium toward the B-conformation, or (c) toward the Z-conformation. If a protein binds to Z-DNA preferentially, then the overall equilibrium of DNA in solution is driven toward Z-DNA, because Z-DNA is then stabilized by both the protein and cobalt hexamine. For a B-DNA binding protein, the equilibrium is driven in the opposite direction. FIG. 14 shows examples of each of these effects. In corroboration of the in vivo results, $vZ_{E3L}$ drives the equilibrium toward the Z-conformation. As discussed above, $hZ\beta_{ADAR}$ is not a Z-DNA binding protein in vivo. It does not shift the B-Z equilibrium in a traditional CD assay, nor does it show Z-DNA binding activity in the gel-mobility shift assay. In the equilibrium midpoint assay, however, $hZ\beta_{ADAR}$ drives the equilibrium towards the B conformation, suggesting that it is not a Z-DNA binding protein but rather a weak B-DNA binding protein. Along with hZβ$_{ADAR}$ and vZ$_{E3L}$, several well-known B-DNA binding proteins were tested including human histone 1 (hHl) and human Pbx homeodomain. The results showed that they are B-DNA binding proteins in this assay as expected. A chimeric protein containing part of hHl (the N-terminal half before helix3) and part of hZα$_{ADAR}$ (the C-terminal half from the recognition helix3) showed no shift in the spectrum toward either a Z- or B-conformation, which is in agreement with the fact that it shows no Z-DNA binding in a CD experiment. There is thus full agreement between the in vivo and these in vitro results. Together these methods provide assays for the study of conformation-specific binding.

Z-DNA Formation Stabilized by Zα Near a Promoter Region Acts as an Enhancer Element Liu et al. (Cell, 106:309–318, 2001) has suggested that Z-DNA, occurring near a promoter, might have a regulatory effect on that promoter. Furthermore, Z-DNA forming sequences are common near transcription start sites (Schroth et al., J. Biol. Chem., 267:11846–11855, 1992). The results described above suggest that the system described here can be modified to detect this effect. hZα$_{ADAR}$ has been utilized as a tool to stimulate the formation of Z-DNA in vivo. hZα$_{ADAR}$ without an activation domain was expressed in yeast cells containing Op or Sm reporter constructs, as described herein. In the absence of an activation domain, hZα$_{ADAR}$ cannot activate β-galactosidase expression by interacting with the promoter, unless the presence of Z-DNA itself has an effect upon transcription of a nearby promoter. Comparison of results from different reporter constructs expressing either hZα$_{ADAR}$ or hZaa$_{ADAR}$ showed that increasing Z-DNA formation was proportional to reporter gene expression (FIG. 15). In the absence of hZα$_{ADAR}$ expression, longer repeats of (dC-dG) yielded slightly greater β-galactosidase expression, as described herein. However, this increased level of transcription with longer repeats of (dC-dG) was greatly amplified by the expression of hZα$_{ADAR}$, which is known to facilitate Z-DNA formation (FIG. 15). This effect was even more dramatic in an unfavorable environment for Z-DNA formation, as assessed by transforming yeast cells with recombinant pGNA, pGNA-Zβ, pGNA-Zα, and pGNA-Zaa and pLacZcOp-(dC-dG)$_n$ or pLacZcSm-(dC-dG)$_n$ when n=5, and plating the cells onto selective medium containing X-gal, a β-galactosidase substrate. With (dC-dG)$_5$, activation of the LacZ reporter gene was shown only if Z-DNA formation was induced by hZα$_{ADAR}$ or hZaa$_{ADAR}$ in the Op template. However, when this experiment ws repeated with a longer stretch of (dC-dG), (dC-dG)$_9$ provided more binding sites for hZα$_{ADAR}$ so that Z-DNA was readily formed even when positive supercoiling was produced from the URA3 promoter in the Sm plasmid. Thus, induction of Z-DNA by hZα$_{ADAR}$ is responsible for activation of reporter gene transcription. Similar effects were seen for hZab$_{ADAR}$.

EXAMPLE 5

Figure 8A:
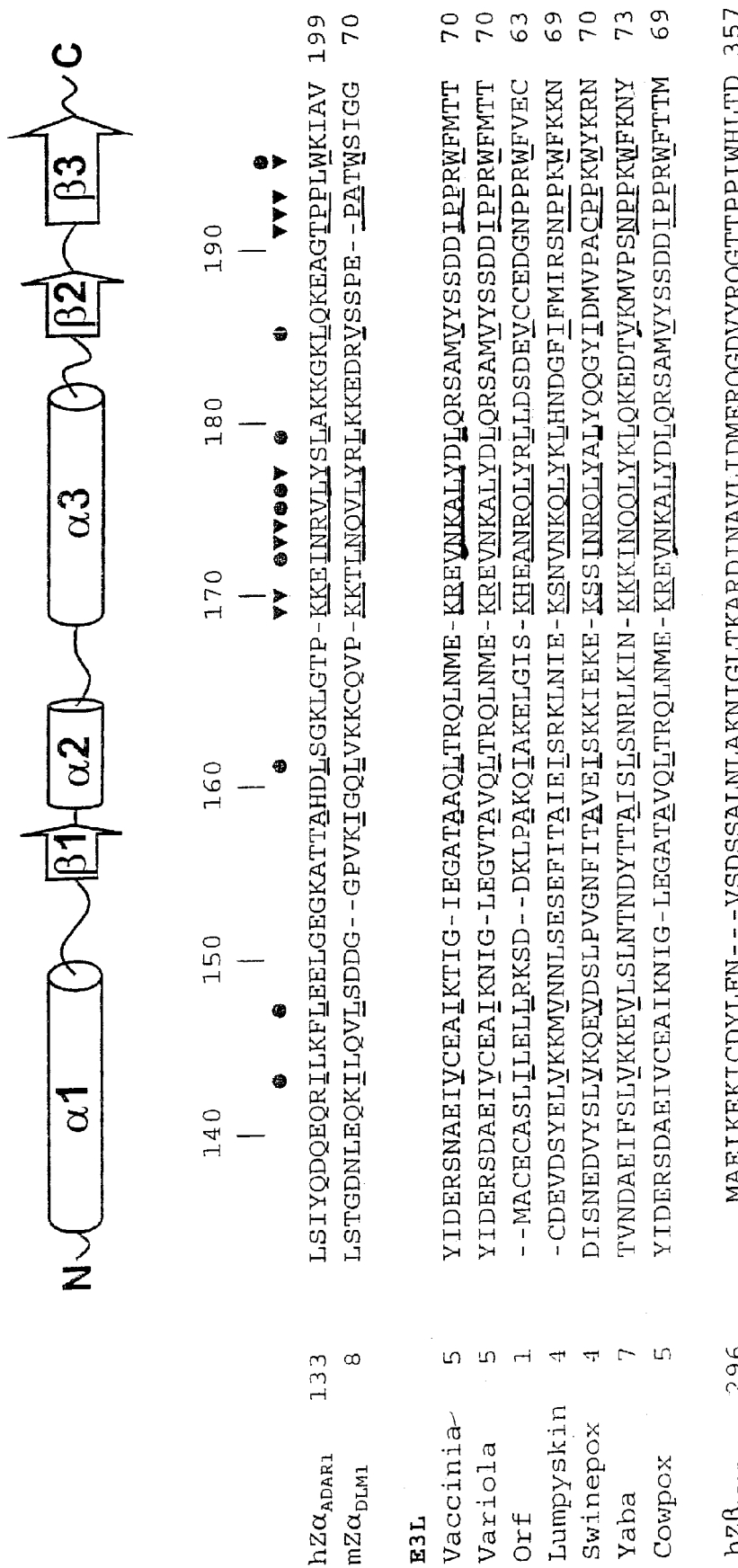
FIG. 8A is an amino acid sequence alignment of portions of human Zα of ADAR1 (SEQ ID NO: 6), murine Zα of DLM (SEQ ID NO: 7), E3L of vaccinia virus (SEQ ID NO: 8), E3L of variola virus (SEQ ID NO: 9), E3L of Orf virus (SEQ ID NO: 10), E3L of Lumpyskin virus (SEQ ID NO: 11), E3L of Swinepox virus (SEQ ID NO: 12), E3L of Yaba-like disease virus (SEQ ID NO: 13), E3L of Cowpox virus (SEQ ID NO: 14), and human Zβ of ADAR1 (SEQ ID NO:15). The numbers at either end of the sequences represent the numbering of amino acid residues in their respective proteins. Amino acid residues having the hydrophobic core are indicated by triangles, and the residues that contact nucleic acids (Z-DNA) are indicated by circles. Underlined residues indicate residues important for the protein fold and for Z-DNA recognition. The secondary structure diagram at the top of the sequences (with the numbering of human Zα of ADAR1) indicates the predicted secondary structure of these proteins. The GenBank Accession Numbers for the various sequences are as follows: double-stranded RNA adenosine deaminase [*Homo sapiens*] AAB06697. 1; tumor stroma and activated macrophage protein DLM-1 [*Mus musculus*] NP 067369; and the E3L proteins [Vaccinia virus] AAA02759; [Variola virus] NP 042088; [Orf virus] AAC08018; [lumpy skin disease virus] AAK84995; [Swinepox] NP570192; [Yaba-like disease virus] NP 073419; and [Cowpox virus] CAC42100.

Treatment of Other Diseases Using Inhibitors of Complex Formation Between a Z-DNA Binding Ligand or Variant Thereof and Z-DNA The variola virus, which is the agent that causes smallpox, has an E3L protein that has high amino acid sequence identity with E3L of vaccinia virus, differing from vaccinia E3L by a limited number of amino acids in the amino-terminal domain (Z-DNA binding domain), for example about 3 to 5 amino acids, depending on which strains are used in the comparison, none of which are implicated in Z-DNA binding. In particular, the amino acid residues in the amino-terminal domain of vaccinia virus E3L that contact Z-DNA (Z-DNA binding domain) are identical to those of the closely related variola virus E3L. For example, the Z-DNA binding domain of the variola virus, shares all 9 amino acid residues known to be important for Z-DNA binding in vaccinia. In addition, Orf virus (FIG. 1C), Ectromelia virus (GenBank Accession Number: AJ312294.1), mousepox virus, Yaba-like disease virus (FIG. 1D), cowpox virus (GenBank Accession Number: AJ312293.1), myxoma virus (GenBank Accession Number: NC00132), lumpy skin disease virus (GenBank Accession Number: NC003027.1), monkeypox virus (GenBank Accession Number: AF380138.1) and rabbit fibroma virus (GenBank Accession Number: NC001266) also contain E3L or E3L-like proteins with high amino acid sequence identity to vaccinia E3L, including high sequence identity to the Z-DNA binding domain. An amino acid sequence alignment of human Zα of ADAR1, human Zα of DLM, E3L of vaccinia virus, E3L of variola virus, E3L of Orf virus, and E3L of yaba-like disease virus are shown in FIG. 8A. These amino acid sequence have hydrophobic residues (indicated by triangles in FIG. 8A) necessary to stabilize the winged helix conformation of the protein, as well as the specific residues found to be important for Z-DNA recognition (indicated by circles in FIG. 8A). In addition, as shown, in FIG. 8A, the E3L sequences of vaccinia virus and variola virus are highly homologous, with the few amino acid residues that are different between the two proteins being removed from the Z-DNA binding site.

Figure 8B:
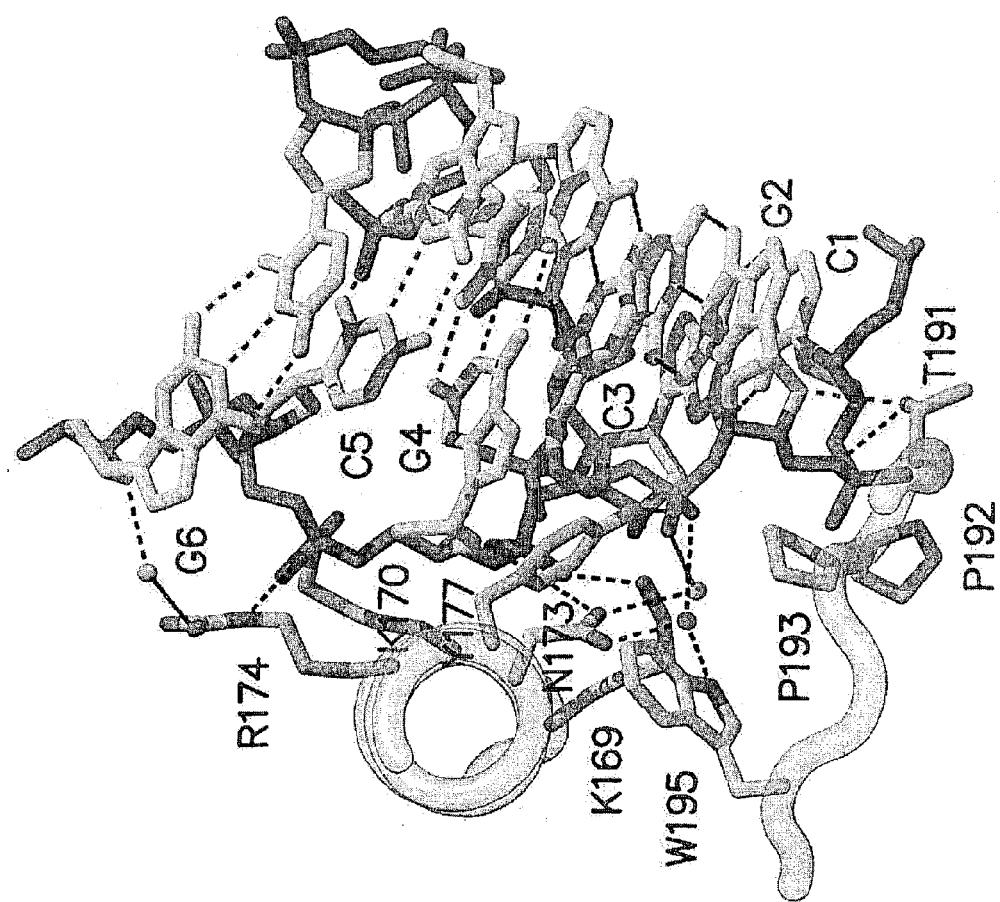
FIG. 8B is a schematic representation of a co-crystal structure of the Zα subunit of ADAR1 bound to Z-DNA. The view is down the recognition helix of the protein (at left), and a number of amino acids are shown that interact with left-handed Z-DNA stabilized by electrostatic and van der Waals interactions. There is an edge-to-face van der Waals interaction between Guanine 4 and Tyrosine 177. Note the van der Waals interactions between prolines 192, 193 and the Z-DNA backbone.

These amino acid-Z-DNA interaction are also shown in FIG. 8B. FIG. 8B is a schematic representation of a co-crystal structure pf the Zα subunit of ADAR1 bound to Z-DNA. This view of the molecule is shown looking down on the recognition helix, which is on the left. A co-crystal structure pf the Zα subunit of DLM bound to Z-DNA has also been solved and region of DLM that interact with Z-DNA have been identified.

EXAMPLE 6

Identification of Inhibitors of Formation of a Complex Between a Z-DNA Binding Ligand or Variant Thereof and Z-DNA Recent X-ray diffraction studies of the binding of Z-DNA to either Zα (from the editing enzyme ADAR1) or DLM, both bound to Z-DNA illustrate the similarity of the two structures to each other (Schwartz et al., Science, supra; and Schwartz et al., Nature Structural Biology, 8:761–765, 2001). A comparison of sequences of E3L molecules from poxviruses shows that this is in the same family of proteins. These proteins all have two constant features that are essential for their structure and activity. The folding motif is a helix-turn-helix with a β-sheet wing attached. The folding of the helix-turn-helix domain is maintained by a core of hydrophobic amino acids that hold the molecule in its folded conformation through their interactions. These residues are homologous in all members of this class of Z-DNA binding proteins and provide the overall form of the molecule.

A second class of residues on the surface of the molecule is essential for recognizing and binding Z-DNA. These residues are usually identical, but in some cases they are similar residues. ("Similar" residues can, for example, involve a lysine residue substituting for an arginine residue or vice versa. Both of these residues are positively charged with somewhat similar side chains.) To make a model of the E3L molecules for vaccinia (or variola, or other E3L), the amino acids in E3L were substituted for the analogous residues in Zα of ADAR1. The identical residues were maintained as identical, and the similar residues were put in the same conformation. The final conformation was obtained by carrying out well known techniques of energy minimization which allow for small movements of the side chains to minimize van der Waals contacts with neighboring side chains, and in that way, obtain the lowest energy conformation of the molecule. The changes in the configuration of the molecule are not very great when comparing E3L with Zα.

FIG. 2A shows a van der Waals surface of the molecule which shows the outline of all the residues and superimposed on it is a ball-and-stick diagram of Z-DNA as it appears in the crystal structure of the complexes. Those residues that are involved in Z-DNA recognition are outlined in black with stick diagrams illustrating the conformation of the relevant side chains. It can be seen that the dark gray area associated with Z-DNA binding residues form one large block with another, narrower block extending from it with a sliver of light gray between the two blocks. This is a segment of the molecule that is depressed beneath the surface, so that the dark gray residues are at the upper level where they can bind to Z-DNA, whereas, the residues in light gray in this center region are further away from the surface, making a slight crevice.

A solution NMR study was carried out of the structure of Zα of ADAR1 in solution in the absence of Z-DNA (Schade et al., Proc. Natl. Acad. Sci. USA, 96:12465–12470, 1999). What was of particular interest in that study was to determine the conformations of the side chains that are involved in Z-DNA recognition. What was discovered is that the side chains are pre-positioned for recognition of Z-DNA in the same conformation in solution as they are in the crystal structure of the complex. The only exception to this observation is the tyrosine residue (Y177) that shows some wobbling rotation of the ring. However, the fact that most of the residues are pre-positioned suggests that a good estimate can be made of the binding surface to which an inhibitor, such as a small molecule, can attach in order to inhibit the activity of the E3L molecule. This is shown in FIG. 2B, in which the side chains of the recognition residues are found together, drawn in a stick format. The binding sites, a number of distances in angstroms, are illustrated for electronegative atoms. It can be seen that the total distance is an area of over 200 square Å that can be used as a target for an inhibitor, such as a small molecule, to bind to the site. For example, this structure can be used to carry out high-throughput screening to look for a small molecule that would inhibit the binding of E3L to Z-DNA.

In view of the results described herein and the amino acid sequence similarity between E3L N-terminal domains of the orthopox viruses, and in particular the near identity of the vaccinia and variola E3L molecules, it is possible to develop an anti-infective agent (e.g., a small molecule) that will prevent the E3L molecule from binding to Z-DNA. Binding of the agent to the Z-DNA binding site of E3L would interfere with E3L binding to Z-DNA, and thus diminish or abolish pathogenicity of the virus. Such an inhibitor can be tested directly in mice in the case of vaccinia. These inhibitors can also be tested in a primate model of variola infection (Enserink and Stone, Science 295:2001–2005, 2002). Methods for identifying inhibitors of Z-DNA binding are described in greater detail herein.

Finding an agent (e.g., a small molecule) that can bind to the orthopox virus E3L molecules is a process of drug discovery, and can be thought of as occurring in several stages:

1. Identification, through computations or high-throughput screening of an agent (e.g., small molecule lead compounds), that binds to Z-DNA binding ligands or variants thereof, such as the N-terminal domain of E3L or Zα of ADAR1;
2. Optionally confirming that the binding is to the Z-DNA binding site of the Z-DNA binding molecule; and
3. Optionally, optimizing one or more lead compounds to enhance affinity of small molecule binding.

Animal tests to assess the activity of the small molecule in blocking the pathogenic effect of the orthopox virus can be performed.

Any suitable assay, including those described herein can be used to identify an agent or lead compound that binds to a Z-DNA binding ligand or variant thereof. In one embodiment, a suitable high-throughput screening assay can then be used to search through one or more libraries of compounds.

One approach for obtaining small molecule binding properties is, if the Z-DNA binding ligand, for example, an E3L or a protein with sequence similarity to E3L, for example, ADAR1, is fluorescently labeled, then a fluorescent signal can be used to indicate binding to Z-DNA, and the disruption of that signal by a small molecule can be used to isolate specific inhibitors. An example of such an assay, suitable for high-throughput screening to find lead compounds according to the above method is as follows. Poly(dG-dC) is tethered to the bottom of a 96-well titer plate. A molecule such as Zα (ADAR1) is modified so that a fluorescent tag is added to it. Adding the fluorescent labeled Zα to the solution of poly(dG-dC) results in binding to the tethered DNA so it will not be removed by subsequent washing. The presence of the bound protein can be detected by fluorescence, and the presence of a test agent that prevents the binding is indicated by the loss of fluorescence.

Another method for high-throughput screening of inhibitors involves "in silico" screening using a computer program that contains in its memory 1–2 million small molecules and carries out an operation in which the small molecules are docked to the binding site and moved around in order to look for energy minimization, using any suitable computer program, for example, CNS (Crystallographic NMR System). The binding energy is then calculated successively for the library of molecules, and from this, candidate molecules can be identified. These molecules and structural variants can be screened (e.g., by high-throughput screening).

Methods for "in silico" screening, include de novo rational drug design, ligand optimization, pharmacophor technology, and ligand/small molecule docking methods are known in the art and are described, for example, in U.S. Pat. Nos. 5,854,992 and 5,712,171, and in U.S. Patent Publication No. 2002/0055536 A1, the entire teachings of which are incorporated herein by reference.

The most promising candidates from the "in silico" screening can be chemically synthesized so their ability to block Z-DNA binding can be measured experimentally.

Once a lead compound is identified, it is useful to confirm where and how the compound binds to the Z-DNA binding site. This can be carried out in a number of ways, the simplest being to measure the circular dichroism of $d(CG)_n$ on the addition of Zα, as described herein. If the compound inhibits conversion to Z-DNA, then it is likely that the binding is at or near the Z-DNA binding site of protein. Optionally, promising compounds can be studied further by co-crystallization with the Zα domain to determine the detailed position of the small molecule binding site. Since the structure of the Zα domain is known, the crystal structure can be solved quite readily.

Optimization of the binding in order to lower the dissociation constant ($K_d$) can be performed. This process involves organic chemistry in which a variety of derivatives of the initial lead compound can be made.

In addition to the derivatization of a lead compound by adding groups in different positions, knowledge of the three-dimensional structure of the compound to the domain may make it possible to use rational drug design as a guide in the addition of residues in positions likely to enhance binding.

Animal testing to assess toxicity and dose response of the binding compound (e.g., to prevent lethality of the pox virus given to mice) can be performed. Assays such as those described herein, or other methods for assessing toxicity can be used to determine the toxicity of the compound.

A number of proteins can be used in the search for inhibitors that bind to the Z-DNA binding surface of the proteins. These proteins include, for example, Z-DNA binding domains of ADAR1, DLM1 and E3L of vaccinia. Although these proteins largely differ in their amino acid sequences, they have a commonality of amino acid residues found in the Z-DNA binding site. Thus, inhibitors that bind to these three subunits can be assayed. The Z-DNA binding surface of the proteins is similar in all three molecules, while the other surfaces are different. In addition to these molecules which have been studied, other E3L N-terminal domains from the ORF virus as well as the YABA virus (FIG. 8A) can be used. Both of these molecules have been synthesized in the laboratory using the DNA that codes for them.

EXAMPLE 7

Treatment of Mice Infected with Virus

In one example, mice, (e.g., C57BL/6 breeders) are infected with vaccinia virus, as described by Brandt and Jacobs (supra; the teachings of which are incorporated by reference) and candidate inhibitors of the formation of a complex between a Z-DNA binding ligand and Z-DNA tested for their ability to inhibit or decrease pathogenicity as follows. The mice are first administered an anesthetic, for example, 1 μl/gram of body weight of a cocktail containing xylazine (7.5 mg/ml), acepromazine maleate (2.5 mg/ml), and ketamine (37.5 mg/kg) intramuscularly. Following anesthesia, virus is administered intranasally in 10 μl doses sufficient to cause mortality (for example, $10^3$, $10^4$, $10^5$, $10^6$, or $10^7$ p.f.u., depending on the desired duration of the experiment), using for example, a micropipet loaded with a gel loading tip. The mice are observed daily for signs of illness, including ruffled fur and lack of activity, and for mortality. In addition, weight loss can be used to measure pathogenesis, as loss of weight directly correlates with fever in poxvirus infections in animals (Bloom et al., J. Virol., 65:1530–1542, 1991; the teachings of which are incorporated by reference). Alternatively, the virus can be administered to an anesthetized mouse via intracranial injection, using, for example, 10 μl of virus and a 27-gauge hypodermic needle and a 1 ml syringe.

The inhibitor is administered to the mouse either prior to, concurrent with, or after viral infection. Administration can be by any appropriate route. Preferably, the mode of administration provides for systemic delivery. Possible controls for such studies include a set of mice that are infected with the virus, but do not receive the inhibitor, and mice that are infected with the virus, and are administered the inhibitor vehicle only.

A compound that decreases the pathogenicity (for example, mortality, weight loss, coat roughness) of the mice infected with virus is an inhibitor of binding of a Z-DNA binding ligand to Z-DNA. Such an inhibitor can be used to treat an individual infected with the virus.

One method for decreasing the pathogenicity of vaccinia virus was performed as follows. A composition of liposomes containing poly(dG-dC) (2 mM (base pair)), brominated such that it forms chemically stabilized Z-DNA was made, according to methods known in the art. Generally approximately 50% of the poly(dG-dC) remains in the DNA-liposomes composition. One group of five mice were intracranially inoculated with vaccinia virus alone, a second group of five mice were inoculated with vaccinia virus plus 10 μL of the the Z-DNA-liposomes composition, while a third group of mice were inoculated with vaccinia virus plus 10 μL of the Z-DNA-liposomes composition diluted 10-fold. The mice that received the virus alone died in approximately 1 week, while the mice that were administered virus plus Z-DNA contained in liposomes lived for at least two weeks, when the study was concluded.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of detecting and/or identifying an inhibitor of binding of a Z-DNA binding ligand to Z-DNA, comprising the steps of:
   a) combining an agent to be tested, Z-DNA, and a composition comprising a Z-DNA binding ligand, under conditions suitable for binding of said Z-DNA binding ligand to said Z-DNA; and
   b) detecting the formation of a complex between said Z-DNA binding ligand and said Z-DNA, wherein inhibition of formation of said complex by said agent relative to a suitable control is indicative that the agent is an inhibitor,
   wherein said Z-DNA binding ligand is a fusion protein comprising a Z-DNA binding ligand and a detectable label, and wherein formation of said complex is detected by detecting said detectable label.

2. The method of claim 1, wherein said Z-DNA binding ligand is a fusion protein comprising a Z-DNA binding ligand selected from the group consisting of E3L, ADAR1 and DLM-1.

3. The method of claim 1, wherein said fusion protein comprises a Z-DNA binding ligand and a green fluorescent protein.

4. The method of claim 1, wherein said fusion protein comprises a Z-DNA binding ligand and a glutathione S-transferase protein.

5. The method of claim 1, wherein said detectable label is selected from the group consisting of an epitope tag, an affinity label, an enzyme, and a fluorescent moiety.

6. The method of claim 1, wherein said method is a competition assay in which binding is determined in the presence of one or more Z-DNA binding ligand.

7. The method of claim 1, wherein the agent to be tested is selected from the group consisting of small organic molecules, peptides, proteins and peptidomimetics.

8. The method of claim 1, wherein the agent to be tested is an antibody or antigen-binding fragment thereof.

9. The method of claim 8, wherein said antibody or antigen-binding fragment binds to said ligand.

10. The method of claim 8, wherein said antibody or antigen-binding fragment binds to Z-DNA.

11. The method of claim 1, wherein said Z-DNA consists essentially of an oligonucleotide.

12. The method of claim 1, wherein said Z-DNA consists essentially of a plasmid.

13. A method of detecting and/or identifying an anti-infective agent, comprising the steps of:
   a) combining an agent to be tested, Z-DNA and a composition comprising a Z-DNA binding ligand under conditions suitable for binding of said Z-DNA binding ligand to said Z-DNA;
   b) detecting the formation of a complex between said Z-DNA binding ligand and said Z-DNA, wherein inhibition of formation of said complex by said agent relative to a suitable control is indicative that the agent is an anti-infective agent; and c) assessing the anti-infective activity of said agent in a suitable assay.

14. A method of detecting and/or identifying an anti-infective agent, comprising the steps of:

a) contacting a cell comprising a Z-DNA binding ligand and Z-DNA with an agent to be tested, under conditions suitable for binding of said Z-DNA binding ligand to said Z-DNA; and b) detecting the formation of a complex between said Z-DNA binding ligand and said Z-DNA, wherein inhibition of formation of said complex by said agent relative to a suitable control is indicative that the agent is an anti-infective agent; and c) assessing the anti-infective activity of said agent in a suitable assay.

15. The method of claim 14, wherein binding of said Z-DNA binding ligand to Z-DNA can mediate cellular signaling and/or a cellular response, and said binding is detected by detecting a signaling activity or cellular response in response to said binding.

16. The method of claim 14, wherein the assay of step c) is an assay for anti-viral activity.

17. A method of detecting and/or identifying an inhibitor of binding of a Z-DNA binding ligand to Z-DNA, comprising the steps of:

a) combining an agent to be tested, a composition comprising a Z-DNA binding ligand and Z-DNA, under conditions suitable for binding of said Z-DNA binding ligand to said Z-DNA; and b) detecting the formation of a complex between said Z-DNA binding ligand and said Z-DNA, wherein inhibition of formation of said complex by said agent relative to a suitable control is indicative that the agent is an inhibitor, wherein said Z-DNA binding ligand is selected from the group consisting of E3L, ADAR1, DLM-1, and a fusion protein comprising any one of the foregoing.

18. The method of claim 17, wherein said Z-DNA binding ligand is a fusion protein comprising E3L, ADAR1 or DLM-1.

19. The method of claim 18, wherein said fusion protein comprises a green fluorescent protein or a glutathione S-transferase protein.

20. The method of claim 17, wherein said Z-DNA binding ligand is labeled with a detectable label.

21. The method of claim 20, wherein said detectable label is selected from the group consisting of a radioisotope, an epitope tag, an affinity label, an enzyme, a fluorescent moiety and a chemiluminescent group.

22. The method of claim 17, wherein said Z-DNA consists essentially of an oligonucleotide.

23. The method of claim 17, wherein said Z-DNA consists essentially of a plasmid.

24. The method of claim 13, wherein said Z-DNA binding ligand is selected from the group consisting of E3L, ADAR1, DLM-1, and a fusion protein comprising any one of the foregoing.

25. The method of claim 13, wherein said Z-DNA binding ligand is a fusion protein comprising a Z-DNA binding ligand and a detectable label, and wherein formation of said complex is detected by detecting said detectable label.

26. The method of claim 25, wherein said detectable label is a green fluorescent protein or a glutathione S-transferase protein.

27. The method of claim 13, wherein said Z-DNA binding ligand is labeled with a detectable label.

28. The method of claim 27, wherein said detectable label is selected from the group consisting of a radioisotope, an epitope tag, an affinity label, an enzyme, a fluorescent moiety and a chemiluminescent group.

29. The method of claim 13, wherein said method is a competition assay in which binding is determined in the presence of more than one Z-DNA binding ligand.

30. The method of claim 13, wherein the agent to be tested is selected from the group consisting of small organic molecules, peptides, proteins and peptidomimetics.

31. The method of claim 13, wherein the agent to be tested is an antibody or antigen-binding fragment thereof.

32. The method of claim 13, wherein said Z-DNA consists essentially of an oligonucleotide.

33. The method of claim 13, wherein said Z-DNA consists essentially of a plasmid.

34. A method of detecting and/or identifying an anti-viral agent, comprising the steps of:

a) combining an agent to be tested, Z-DNA and a composition comprising a Z-DNA binding ligand, under conditions suitable for binding of said Z-DNA binding ligand to said Z-DNA;

b) detecting the formation of a complex between said Z-DNA binding ligand and said Z-DNA, wherein inhibition of formation of said complex by said agent relative to a suitable control is indicative that the agent is an anti-viral agent; and c) assessing the anti-viral activity of said agent in a suitable assay.

35. The method of claim 34, wherein said Z-DNA binding ligand is selected from the group consisting of E3L, ADAR1, DLM-1, and a fusion protein comprising any one of the foregoing.

36. The method of claim 34, wherein said Z-DNA binding ligand is a fusion protein comprising a Z-DNA binding ligand and a detectable label, and wherein formation of said complex is detected by detecting said detectable label.

37. The method of claim 36, wherein said detectable label is a green fluorescent protein or a glutathione S-transferase protein.

38. The method of claim 34, wherein said Z-DNA binding ligand is labeled with a detectable label.

39. The method of claim 38, wherein said detectable label is selected from the group consisting of a radioisotope, an epitope tag, an affinity label, an enzyme, a fluorescent moiety and a chemiluminescent group.

40. The method of claim 34, wherein said method is a competition assay in which binding is determined in the presence of more than one Z-DNA binding ligand.

41. The method of claim 34, wherein the agent to be tested is selected from the group consisting of small organic molecules, peptides, proteins and peptidomimetics.

42. The method of claim 34, wherein the agent to be tested is an antibody or antigen-binding fragment thereof.

43. The method of claim 42, wherein said antibody or antigen-binding fragment binds to said ligand.

44. The method of claim 42, wherein said antibody or antigen-binding fragment binds to Z-DNA.

45. The method of claim 34, wherein said Z-DNA consists essentially of an oligonucleotide.

46. The method of claim 34, wherein said Z-DNA consists essentially of a plasmid.

47. The method of claim 34, wherein step a) is performed by contacting a cell comprising a Z-DNA binding ligand and Z-DNA with the agent to be tested.

48. A method of detecting and/or identifying an anti-poxvirus agent, comprising the steps of:

a) combining an agent to be tested, Z-DNA and a composition comprising a protein, said protein comprising a poxvirus E3L or a Z-DNA binding domain thereof, under conditions suitable for binding of said poxvirus E3L or a Z-DNA binding domain thereof to said Z-DNA; and b) detecting the formation of a complex between said poxvirus E3L or a Z-DNA binding domain thereof and said Z-DNA, wherein inhibition of formation of said complex by said agent relative to a suitable control is indicative that the agent is an anti-poxvirus agent.

49. The method of claim 48, wherein said poxvirus E3L is a vaccinia virus E3L or a variola virus E3L.

50. The method of claim 48, further comprising the step of assessing the anti-viral activity of the agent against poxvirus in a suitable assay.

51. The method of claim 48, wherein step a) is performed by contacting a cell comprising a protein, said protein comprising a poxvirus E3L or a Z-DNA binding domain thereof and Z-DNA with the agent to be tested.

* * * * *

UNITED STATES PATENT AND TRADEMARK OFFICE
CERTIFICATE OF CORRECTION

PATENT NO. : 7,001,718 B2
APPLICATION NO. : 10/321785
DATED : February 21, 2006
INVENTOR(S) : Bertram L. Jacobs and Alexander Rich It is certified that error appears in the above-identified patent and that said Letters Patent is hereby corrected as shown below:

In Claim 6, column 66, line 43, delete "one or more Z-DNA binding ligand" and insert --more than one Z-DNA binding ligand--.

Signed and Sealed this

Fourth Day of July, 2006

JON W. DUDAS
*Director of the United States Patent and Trademark Office*

SEQUENCE LISTING

<160> NUMBER OF SEQ ID NOS: 33

<210> SEQ ID NO 1
<211> LENGTH: 190
<212> TYPE: PRT
<213> ORGANISM: Unknown
<220> FEATURE:
<223> OTHER INFORMATION: Vaccinia virus

<400> SEQUENCE: 1

Met Ser Lys Ile Tyr Ile Asp Glu Arg Ser Asn Ala Glu Ile Val Cys
 1               5                  10                  15

```
Glu Ala Ile Lys Thr Ile Gly Ile Glu Gly Ala Thr Ala Ala Gln Leu
            20                  25                  30

Thr Arg Gln Leu Asn Met Glu Lys Arg Glu Val Asn Lys Ala Leu Tyr
        35                  40                  45

Asp Leu Gln Arg Ser Ala Met Val Tyr Ser Ser Asp Ile Pro Pro
    50                  55                  60

Arg Trp Phe Met Thr Thr Glu Ala Asp Glu Ala Asp Ala Asp Ala Met
65                  70                  75                  80

Ser Asp Val Ile Ile Asp Asp Val Ser Arg Glu Lys Ser Met Arg Glu
                85                  90                  95

Asp His Lys Ser Phe Asp Asp Val Ile Pro Ala Lys Lys Ile Ile Asp
            100                 105                 110

Trp Lys Gly Ala Asn Pro Val Thr Val Ile Asn Glu Tyr Cys Gln Ile
            115                 120                 125

Thr Arg Arg Asp Trp Ser Phe Arg Ile Glu Ser Val Gly Pro Ser Asn
    130                 135                 140

Ser Pro Thr Phe Tyr Ala Cys Val Asp Ile Asp Gly Arg Val Phe Asp
145                 150                 155                 160

Lys Ala Asp Gly Lys Ser Lys Arg Asp Ala Lys Asn Ala Ala Lys
                165                 170                 175

Leu Ala Val Asp Lys Leu Leu Gly Tyr Val Ile Ile Arg Phe
            180                 185                 190

<210> SEQ ID NO 2
<211> LENGTH: 190
<212> TYPE: PRT
<213> ORGANISM: Unknown
<220> FEATURE:
<223> OTHER INFORMATION: Variola virus

<400> SEQUENCE: 2

Met Ser Lys Ile Tyr Ile Asp Glu Arg Ser Asp Ala Glu Ile Val Cys
1               5                   10                  15

Glu Ala Ile Lys Asn Ile Gly Leu Glu Gly Val Thr Ala Val Gln Leu
            20                  25                  30

Thr Arg Gln Leu Asn Met Glu Lys Arg Glu Val Asn Lys Ala Leu Tyr
        35                  40                  45

Asp Leu Gln Arg Ser Ala Met Val Tyr Ser Ser Asp Ile Pro Pro
    50                  55                  60

Arg Trp Phe Met Thr Thr Glu Ala Asp Lys Pro Asp Ala Met Thr Met
65                  70                  75                  80

Ala Asp Val Ile Ile Asp Asp Val Ser Arg Glu Lys Ser Met Arg Glu
                85                  90                  95

Asp His Lys Ser Phe Asp Asp Val Ile Pro Ala Lys Lys Ile Ile Asp
            100                 105                 110

Trp Lys Asn Ala Asn Pro Val Thr Ile Ile Asn Glu Tyr Cys Gln Ile
            115                 120                 125

Thr Lys Arg Asp Trp Ser Phe Arg Ile Glu Ser Val Gly Pro Ser Asn
    130                 135                 140

Ser Pro Thr Phe Tyr Ala Cys Val Asp Ile Asp Gly Arg Val Phe Asp
145                 150                 155                 160

Lys Ala Asp Gly Lys Ser Lys Arg Asp Ala Lys Asn Ala Ala Lys
                165                 170                 175

Leu Ala Val Asp Lys Leu Leu Gly Tyr Val Ile Ile Arg Phe
            180                 185                 190
```

```
<210> SEQ ID NO 3
<211> LENGTH: 183
<212> TYPE: PRT
<213> ORGANISM: Unknown
<220> FEATURE:
<223> OTHER INFORMATION: Orf virus

<400> SEQUENCE: 3
```

Met Ala Cys Glu Cys Ala Ser Leu Ile Leu Glu Leu Leu Arg Lys Ser
1               5                   10                  15

Asp Asp Lys Leu Pro Ala Lys Gln Ile Ala Lys Glu Leu Gly Ile Ser
            20                  25                  30

Lys His Glu Ala Asn Arg Gln Leu Tyr Arg Leu Leu Asp Ser Asp Glu
        35                  40                  45

Val Cys Cys Glu Asp Gly Asn Pro Pro Arg Trp Phe Val Glu Cys Ala
    50                  55                  60

Pro Ser Ala Pro Thr Glu Asp Glu Asn Ser Asp Thr Glu Pro Met
65                  70                  75                  80

Glu Thr Glu Ala Gly Cys Asp Thr Leu Phe Gly Gly Asp Ile Asp Ile
                85                  90                  95

Met Thr Gln Ser Ala Val Ile Arg Leu Lys Ser Leu Asn Pro Val Ser
            100                 105                 110

Ala Val Asn Glu Phe Cys Met Met Thr Arg Arg Ser Leu Glu Phe Cys
        115                 120                 125

Glu Thr Arg Ser Gly Gly Glu Asp His Cys Pro Arg Phe Thr Cys Thr
    130                 135                 140

Ile Thr Ile Ser Gly Lys Val Val Ala Ala Asp Gly Ala Ser Lys
145                 150                 155                 160

Lys Leu Ala Arg His Thr Ala Cys Ser Ser Ala Leu Thr Ile Leu Ile
                165                 170                 175

Asn Asn Cys Gly Ile Ser Phe
            180

```
<210> SEQ ID NO 4
<211> LENGTH: 185
<212> TYPE: PRT
<213> ORGANISM: Unknown
<220> FEATURE:
<223> OTHER INFORMATION: Yaba-like disease virus

<400> SEQUENCE: 4
```

Met Asp Leu Leu Ser Cys Thr Val Asn Asp Ala Glu Ile Phe Ser Leu
1               5                   10                  15

Val Lys Lys Glu Val Leu Ser Leu Asn Thr Asn Asp Tyr Thr Thr Ala
            20                  25                  30

Ile Ser Leu Ser Asn Arg Leu Lys Ile Asn Lys Lys Ile Asn Gln
        35                  40                  45

Gln Leu Tyr Lys Leu Gln Lys Glu Asp Thr Val Lys Met Val Pro Ser
    50                  55                  60

Asn Pro Pro Lys Trp Phe Lys Asn Tyr Asn Cys Asp Asn Gly Glu Lys
65                  70                  75                  80

His Asp Ser Lys Leu Glu Gln Lys Asn His Ile Pro Asn His Ile Phe
                85                  90                  95

Ser Asp Thr Val Pro Tyr Lys Lys Ile Ile Asn Trp Lys Asp Lys Asn
            100                 105                 110

Pro Cys Ile Val Leu Asn Glu Tyr Cys Gln Phe Thr Cys Arg Asp Trp

-continued

```
                115                 120                 125
Ser Ile Asp Ile Thr Thr Ser Gly Lys Ser His Cys Pro Met Phe Thr
            130                 135                 140

Ala Thr Val Ile Ile Ser Gly Ile Lys Phe Lys Pro Ala Ile Gly Asn
145                 150                 155                 160

Thr Lys Arg Glu Ala Lys Tyr Asn Ala Ser Lys Ile Thr Met Asp Glu
                165                 170                 175

Ile Leu Asp Ser Val Ile Ile Lys Phe
            180                 185

<210> SEQ ID NO 5
<211> LENGTH: 27
<212> TYPE: PRT
<213> ORGANISM: Artificial Sequence
<220> FEATURE:
<223> OTHER INFORMATION: Consensus Z-DNA binding amino acid sequence
<220> FEATURE:
<221> NAME/KEY: VARIANT
<222> LOCATION: 2
<223> OTHER INFORMATION: Xaa = Lys or Arg
<220> FEATURE:
<221> NAME/KEY: VARIANT
<222> LOCATION: 3, 4, 7, 8, 10-22, 26
<223> OTHER INFORMATION: Xaa = Any Amino Acid
<220> FEATURE:
<221> NAME/KEY: VARIANT
<222> LOCATION: 6
<223> OTHER INFORMATION: Xaa = Arg or Lys
<220> FEATURE:
<221> NAME/KEY: VARIANT
<222> LOCATION: 23
<223> OTHER INFORMATION: Xaa = Thr or Ile

<400> SEQUENCE: 5

Lys Xaa Xaa Xaa Asn Xaa Xaa Xaa Tyr Xaa Xaa Xaa Xaa Xaa Xaa Xaa
1               5                   10                  15

Xaa Xaa Xaa Xaa Xaa Xaa Xaa Pro Pro Xaa Trp
            20                  25

<210> SEQ ID NO 6
<211> LENGTH: 67
<212> TYPE: PRT
<213> ORGANISM: Homo Sapiens

<400> SEQUENCE: 6

Leu Ser Ile Tyr Gln Asp Gln Glu Gln Arg Ile Leu Lys Phe Leu Glu
1               5                   10                  15

Glu Leu Gly Glu Gly Lys Ala Thr Thr Ala His Asp Leu Ser Gly Lys
            20                  25                  30

Leu Gly Thr Pro Lys Lys Glu Ile Asn Arg Val Leu Tyr Ser Leu Ala
        35                  40                  45

Lys Lys Gly Lys Leu Gln Lys Glu Ala Gly Thr Pro Pro Leu Trp Lys
    50                  55                  60

Ile Ala Val
65

<210> SEQ ID NO 7
<211> LENGTH: 63
<212> TYPE: PRT
<213> ORGANISM: Mus Musculus

<400> SEQUENCE: 7

Leu Ser Thr Gly Asp Asn Leu Glu Gln Lys Ile Leu Gln Val Leu Ser
1               5                   10                  15
```

-continued

Asp Asp Gly Gly Pro Val Lys Ile Gly Gln Leu Val Lys Lys Cys Gln
            20                  25                  30

Val Pro Lys Lys Thr Leu Asn Gln Val Leu Tyr Arg Leu Lys Lys Glu
            35                  40                  45

Asp Arg Val Ser Ser Pro Glu Pro Ala Thr Trp Ser Ile Gly Gly
    50                  55                  60

<210> SEQ ID NO 8
<211> LENGTH: 66
<212> TYPE: PRT
<213> ORGANISM: Unknown
<220> FEATURE:
<223> OTHER INFORMATION: Vaccinia Virus

<400> SEQUENCE: 8

Tyr Ile Asp Glu Arg Ser Asn Ala Glu Ile Val Cys Glu Ala Ile Lys
 1               5                  10                  15

Thr Ile Gly Ile Glu Gly Ala Thr Ala Ala Gln Leu Thr Arg Gln Leu
            20                  25                  30

Asn Met Glu Lys Arg Glu Val Asn Lys Ala Leu Tyr Asp Leu Gln Arg
            35                  40                  45

Ser Ala Met Val Tyr Ser Ser Asp Ile Pro Pro Arg Trp Phe Met
    50                  55                  60

Thr Thr
65

<210> SEQ ID NO 9
<211> LENGTH: 66
<212> TYPE: PRT
<213> ORGANISM: Unknown
<220> FEATURE:
<223> OTHER INFORMATION: Variola virus

<400> SEQUENCE: 9

Tyr Ile Asp Glu Arg Ser Asp Ala Glu Ile Val Cys Glu Ala Ile Lys
 1               5                  10                  15

Asn Ile Gly Leu Glu Gly Val Thr Ala Val Gln Leu Thr Arg Gln Leu
            20                  25                  30

Asn Met Glu Lys Arg Glu Val Asn Lys Ala Leu Tyr Asp Leu Gln Arg
            35                  40                  45

Ser Ala Met Val Tyr Ser Ser Asp Ile Pro Pro Arg Trp Phe Met
    50                  55                  60

Thr Thr
65

<210> SEQ ID NO 10
<211> LENGTH: 63
<212> TYPE: PRT
<213> ORGANISM: Unknown
<220> FEATURE:
<223> OTHER INFORMATION: Orf virus

<400> SEQUENCE: 10

Met Ala Cys Glu Cys Ala Ser Leu Ile Leu Glu Leu Leu Arg Lys Ser
 1               5                  10                  15

Asp Asp Lys Leu Pro Ala Lys Gln Ile Ala Lys Glu Leu Gly Ile Ser
            20                  25                  30

Lys His Glu Ala Asn Arg Gln Leu Tyr Arg Leu Leu Asp Ser Asp Glu
            35                  40                  45

```
Val Cys Cys Glu Asp Gly Asn Pro Pro Arg Trp Phe Val Glu Cys
    50                  55                  60
```

<210> SEQ ID NO 11
<211> LENGTH: 66
<212> TYPE: PRT
<213> ORGANISM: Unknown
<220> FEATURE:
<223> OTHER INFORMATION: Lumpyskin virus

<400> SEQUENCE: 11

```
Cys Asp Glu Val Asp Ser Tyr Glu Leu Val Lys Lys Met Val Asn Asn
1               5                   10                  15

Leu Ser Glu Ser Glu Phe Ile Thr Ala Ile Glu Ile Ser Arg Lys Leu
            20                  25                  30

Asn Ile Glu Lys Ser Asn Val Asn Lys Gln Leu Tyr Lys Leu His Asn
        35                  40                  45

Asp Gly Phe Ile Phe Met Ile Arg Ser Asn Pro Pro Lys Trp Phe Lys
    50                  55                  60

Lys Asn
65
```

<210> SEQ ID NO 12
<211> LENGTH: 67
<212> TYPE: PRT
<213> ORGANISM: Unknown
<220> FEATURE:
<223> OTHER INFORMATION: Swinepox virus

<400> SEQUENCE: 12

```
Asp Ile Ser Asn Glu Asp Val Tyr Ser Leu Val Lys Gln Glu Val Asp
1               5                   10                  15

Ser Leu Pro Val Gly Asn Phe Ile Thr Ala Val Glu Ile Ser Lys Lys
            20                  25                  30

Ile Glu Lys Glu Lys Ser Ser Ile Asn Arg Gln Leu Tyr Ala Leu Tyr
        35                  40                  45

Gln Gln Gly Tyr Ile Asp Met Val Pro Ala Cys Pro Pro Lys Trp Tyr
    50                  55                  60

Lys Arg Asn
65
```

<210> SEQ ID NO 13
<211> LENGTH: 67
<212> TYPE: PRT
<213> ORGANISM: Unknown
<220> FEATURE:
<223> OTHER INFORMATION: Yaba virus

<400> SEQUENCE: 13

```
Thr Val Asn Asp Ala Glu Ile Phe Ser Leu Val Lys Lys Glu Val Leu
1               5                   10                  15

Ser Leu Asn Thr Asn Asp Tyr Thr Thr Ala Ile Ser Leu Ser Asn Arg
            20                  25                  30

Leu Lys Ile Asn Lys Lys Ile Asn Gln Gln Leu Tyr Lys Leu Gln
        35                  40                  45

Lys Glu Asp Thr Val Lys Met Val Pro Ser Asn Pro Pro Lys Trp Phe
    50                  55                  60

Lys Asn Tyr
65
```

```
<210> SEQ ID NO 14
<211> LENGTH: 66
<212> TYPE: PRT
<213> ORGANISM: Unknown
<220> FEATURE:
<223> OTHER INFORMATION: Cowpox virus

<400> SEQUENCE: 14

Tyr Ile Asp Glu Arg Ser Asp Ala Glu Ile Val Cys Glu Ala Ile Lys
 1               5

```
<400> SEQUENCE: 18
aaaatgttgg agtttttaga catggccgag                                    30

<210> SEQ ID NO 19
<211> LENGTH: 52
<212> TYPE: DNA
<213> ORGANISM: Artificial Sequence
<220> FEATURE:
<223> OTHER INFORMATION: Primer used to amplify mega primer to construct
      DNA plasmid

<400> SEQUENCE: 19
ccggcttatc cgcctccgtt gtcatatgcc atatgggagg ggttgtccct tg           52

<210> SEQ ID NO 20
<211> LENGTH: 51
<212> TYPE: DNA
<213> ORGANISM: Artificial Sequence
<220> FEATURE:
<223> OTHER INFORMATION: Primer used to amplify Z-DLM nucleic acid
      molecule

<400> SEQUENCE: 20
tctaaaaagg atcccccggg ctgcctgaaa atggcagaag ctcctgttga c            51

<210> SEQ ID NO 21
<211> LENGTH: 77
<212> TYPE: DNA
<213> ORGANISM: Artificial Sequence
<220> FEATURE:
<223> OTHER INFORMATION: Primer used to amplify Z-DLM nucleic acid
      molecule

<400> SEQUENCE: 21
atctattatg acgtcagcca tagcatcagc atccggctta tccgcctccg ttgtcatgct   60
ccatgttgca ggctctg                                                  77

<210> SEQ ID NO 22
<211> LENGTH: 34
<212> TYPE: DNA
<213> ORGANISM: Artificial Sequence
<220> FEATURE:
<223> OTHER INFORMATION: Oligonucleotide used to generate a gene
      reporter vector

<400> SEQUENCE: 22
ccgaattcgt cggtaccgac ctcgagtcta gagc                               34

<210> SEQ ID NO 23
<211> LENGTH: 42
<212> TYPE: DNA
<213> ORGANISM: Artificial Sequence
<220> FEATURE:
<223> OTHER INFORMATION: Oligonucleotide used to generate a gene
      reporter vector

<400> SEQUENCE: 23
ccgaattcgt cggtcgcgcg cgaccgacct cgagtctaga gc                      42

<210> SEQ ID NO 24
<211> LENGTH: 44
<212> TYPE: DNA
<213> ORGANISM: Artificial Sequence
<220> FEATURE:
<223> OTHER INFORMATION: Oligonucleotide used to generate a gene
      reporter vector
```

```
<400> SEQUENCE: 24
ccgaattcgt cggtcgcgcg cgcgaccgac ctcgagtcta gagc            44

<210> SEQ ID NO 25
<211> LENGTH: 52
<212> TYPE: DNA
<213> ORGANISM: Artificial Sequence
<220> FEATURE:
<223> OTHER INFORMATION: Oligonucleotide used to generate a gene
      reporter vector

<400> SEQUENCE: 25
ccgaattcgt cggtcgcgcg cgcgcgcgcg cgaccgacct cgagtctaga gc    52

<210> SEQ ID NO 26
<211> LENGTH: 58
<212> TYPE: DNA
<213> ORGANISM: Artificial Sequence
<220> FEATURE:
<223> OTHER INFORMATION: Oligonucleotide used to generate a gene
      reporter vector

<400> SEQUENCE: 26
ccgaattcgt cggtcgcgcg cgcgcgcgcg cgcgcgcgac cgacctcgag tctagagc    58

<210> SEQ ID NO 27
<211> LENGTH: 34
<212> TYPE: DNA
<213> ORGANISM: Artificial Sequence
<220> FEATURE:
<223> OTHER INFORMATION: Oligonucleotide used to generate a gene
      reporter vector

<400> SEQUENCE: 27
gctctagact cgaggtcggt accgacgaat tcgg            34

<210> SEQ ID NO 28
<211> LENGTH: 42
<212> TYPE: DNA
<213> ORGANISM: Artificial Sequence
<220> FEATURE:
<223> OTHER INFORMATION: Oligonucleotide used to generate a gene
      reporter vector

<400> SEQUENCE: 28
gctctagact cgaggtcggt cgcgcgcgac cgacgaattc gg            42

<210> SEQ ID NO 29
<211> LENGTH: 44
<212> TYPE: DNA
<213> ORGANISM: Artificial Sequence
<220> FEATURE:
<223> OTHER INFORMATION: Oligonucleotide used to generate a gene
      reporter vector

<400> SEQUENCE: 29
gctctagact cgaggtcggt cgcgcgcgcg accgacgaat tcgg            44

<210> SEQ ID NO 30
<211> LENGTH: 52
<212> TYPE: DNA
<213> ORGANISM: Artificial Sequence
<220> FEATURE:
<223> OTHER INFORMATION: Oligonucleotide used to generate a gene
      reporter vector
```

-continued

```
<400> SEQUENCE: 30
gctctagact cgaggtcggt cgcgcgcgcg cgcgcgcgac cgacgaattc gg          52

<210> SEQ ID NO 31
<211> LENGTH: 58
<212> TYPE: DNA
<213> ORGANISM: Artificial Sequence
<220> FEATURE:
<223> OTHER INFORMATION: Oligonucleotide used to generate a gene
      reporter vector

<400> SEQUENCE: 31
gctctagact cgaggtcggt cgcgcgcgcg cgcgcgcgcg cgcgaccgac gaattcgg    58

<210> SEQ ID NO 32
<211> LENGTH: 27
<212> TYPE: DNA
<213> ORGANISM: Artificial Sequence
<220> FEATURE:
<223> OTHER INFORMATION: Primer used to amplify URA3 transcription unit

<400> SEQUENCE: 32
cggaattcag cacgccatag tgactgg                                     27

<210> SEQ ID NO 33
<211> LENGTH: 34
<212> TYPE: DNA
<213> ORGANISM: Artificial Sequence
<220> FEATURE:
<223> OTHER INFORMATION: Primer used to amplify URA3 transcription unit

<400> SEQUENCE: 33
gactagctag ctcaagcttt tcaattcatc attt                             34
```